(12) United States Patent
Zerangue et al.

(10) Patent No.: US 7,592,369 B2
(45) Date of Patent: *Sep. 22, 2009

(54) ACYLOXYALKYL CARBAMATE PRODRUGS OF TRANEXAMIC ACID, METHODS OF SYNTHESIS AND USE

(75) Inventors: Noa Zerangue, Portola Valley, CA (US); Bernd Jandeleit, Menlo Park, CA (US); Yunxiao Li, Sunnyvale, CA (US); Mark A. Gallop, Santa Clara, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/871,906

(22) Filed: Oct. 12, 2007

(65) Prior Publication Data

US 2008/0153898 A1 Jun. 26, 2008

Related U.S. Application Data

(63) Continuation of application No. 11/455,855, filed on Jun. 20, 2006, now Pat. No. 7,351,740.

(60) Provisional application No. 60/692,625, filed on Jun. 20, 2005.

(51) Int. Cl.
*A61K 31/235* (2006.01)

(52) U.S. Cl. .................................................. 514/533

(58) Field of Classification Search ..................... None
See application file for complete search history.

(56) References Cited

U.S. PATENT DOCUMENTS

| | | | |
|---|---|---|---|
| 2,996,431 A | 8/1961 | Barry | |
| 3,139,383 A | 6/1964 | Neville, Jr. | |
| 3,402,240 A | 9/1968 | Cain et al. | |
| 3,499,925 A | 3/1970 | Naito et al. | |
| 3,811,444 A | 5/1974 | Heller et al. | |
| 3,845,770 A | 11/1974 | Theeuwes et al. | |
| 3,916,899 A | 11/1975 | Theeuwes et al. | |
| 3,962,414 A | 6/1976 | Michaels | |
| 3,992,518 A | 11/1976 | Chien et al. | |
| 4,036,829 A | 7/1977 | Ferres et al. | |
| 4,048,222 A | 9/1977 | Saito et al. | |
| 4,055,580 A | 10/1977 | Bertelli | |
| 4,063,064 A | 12/1977 | Saunders et al. | |
| 4,066,747 A | 1/1978 | Capozza | |
| 4,070,347 A | 1/1978 | Schmitt | |
| 4,071,553 A | 1/1978 | Takahashi et al. | |
| 4,079,038 A | 3/1978 | Choi et al. | |
| 4,083,949 A | 4/1978 | Benedikt | |
| 4,088,864 A | 5/1978 | Theeuwes et al. | |
| 4,093,709 A | 6/1978 | Choi et al. | |
| 4,200,098 A | 4/1980 | Ayer et al. | |
| 4,285,987 A | 8/1981 | Ayer et al. | |
| 4,290,905 A | 9/1981 | Kanbe | |
| 4,421,736 A | 12/1983 | Walters | |
| 4,426,391 A | 1/1984 | Alexander et al. | |
| 4,434,153 A | 2/1984 | Urquhart et al. | |
| 4,483,867 A | 11/1984 | Svahn et al. | |
| 4,721,613 A | 1/1988 | Urquhart et al. | |
| 4,752,470 A | 6/1988 | Mehta | |
| 4,760,057 A | 7/1988 | Alexander | |
| 4,816,263 A | 3/1989 | Ayer et al. | |
| 4,820,523 A | 4/1989 | Shtohryn et al. | |
| 4,851,426 A | 7/1989 | Ladkani et al. | |
| 4,853,229 A | 8/1989 | Theeuwes | |
| 4,916,230 A | 4/1990 | Alexander | |
| 5,229,135 A | 7/1993 | Philippon et al. | |
| 5,401,868 A | 3/1995 | Lund | |
| 5,466,811 A | 11/1995 | Alexander | |
| 5,658,578 A | 8/1997 | Ogawa et al. | |
| 5,684,018 A | 11/1997 | Alexander | |
| 5,690,914 A | 11/1997 | Suetsugu et al. | |
| 5,698,155 A | 12/1997 | Grosswald et al. | |
| 6,171,615 B1 | 1/2001 | Roussin et al. | |
| 6,316,660 B1 | 11/2001 | Sato et al. | |
| 6,375,987 B1 | 4/2002 | Farah et al. | |
| 6,379,700 B2 | 4/2002 | Joachim et al. | |

(Continued)

FOREIGN PATENT DOCUMENTS

| | | |
|---|---|---|
| EP | 0079872 A1 | 5/1983 |
| EP | 0 079 872 B1 | 3/1985 |
| EP | 0167451 A2 | 1/1986 |
| EP | 0 416 689 B1 | 11/1995 |
| JP | 07-165555 A | 6/1995 |
| WO | WO 94/15904 A1 | 7/1994 |
| WO | WO 01/05813 A1 | 1/2001 |
| WO | WO 2005/066122 A2 | 7/2005 |

OTHER PUBLICATIONS

Alderman, D., "A review of cellulose ethers in hydrophilic matrices for oral controlled-release dosage forms," *Int. J. Pharm. Tech. & Prod. Mfr.*, 1984, 5(3):1-9.

Almer, S. et al., "Pharmakokinetics of tranexamic acid in patients with ulcerative colitis and in healthy volunteers after the single installation of 2g rectally," *J. Clin. Pharmacol.*, 1992, 32:49-54.

Astudillo, L. et al., "A very simple oxidation of olefins and ketones with UHP-maleic anhydride," *Heterocycles*, 1993, 36(5):1075-1080.

(Continued)

*Primary Examiner*—Paul A Zucker
(74) *Attorney, Agent, or Firm*—Finnegan, Henderson, Farabow, Garrett & Dunner, LLP

(57) ABSTRACT

Acyloxyalkyl carbamate prodrugs of trans-4-(aminomethyl)-cyclohexanecarboxylic acid, pharmaceutical compositions thereof, methods of making prodrugs of trans-4-(aminomethyl)-cyclohexane-carboxylic acid, and methods of using prodrugs of trans-4-(aminomethyl)-cyclohexanecarboxylic acid and pharmaceutical compositions thereof to treat or prevent various diseases or disorders are disclosed. Acyloxyalkyl carbamate prodrugs of trans-4-(aminomethyl)-cyclohexanecarboxylic acid and pharmaceutical compositions thereof suitable for oral and topical administration and for administration using sustained release dosage forms are also disclosed.

44 Claims, 2 Drawing Sheets

U.S. PATENT DOCUMENTS

| | | | |
|---|---|---|---|
| 6,627,223 | B2 | 9/2003 | Percel et al. |
| 6,927,036 | B2 | 8/2005 | Gallop et al. |
| 7,351,740 | B2 * | 4/2008 | Zerangue et al. ............ 514/533 |
| 2004/0014940 | A1 | 1/2004 | Raillard et al. |
| 2005/0002825 | A1 | 1/2005 | Crescenzi et al. |
| 2005/0070715 | A1 | 3/2005 | Bhat et al. |
| 2005/0222431 | A1 | 10/2005 | Gallop et al. |
| 2007/0027210 | A1 | 2/2007 | Zerangue et al. |

OTHER PUBLICATIONS

Balicki, R. & Kaczmarek, L., "Mild and efficient conversion of nitriles to amides with basic urea-hydrogen peroxide adduct," *Synth. Commun.*, 1993, 23(22):3149-3155.

Bamba, M. et al., "Release mechanisms in gelforming sustained release preparations," *Intl. J. Pharmaceutics*, 1979, 2:307-315.

Bradlow, J. et al., *Patterns of Referral*, University of Oxford, Health Services Research Unit, Table of Contents, 5 pages (1992).

Butcher, K., "Carbamate esters: a simple, mild method of formation," *Synlett*, 1994, pp. 825-826.

Coleman, M. et al., "Polymer Reviews, A practical guide to polymer miscibility," *Polymer*, 1990, 31:1187-1203.

*Compendium of Organic Synthetic Methods*, vols. 1-8, Harrison, I. & Harrison, S., Eds., Table of Contents, John Wiley & Sons, Inc., New York, 32 pages (1971-1996).

*Controlled Drug Bioavailability*, vol. 1, Drug Product Design and Performance, Table of Contents, John Wiley & Sons, New York, 2 pages (1984).

Cooper, M. et al., "Oxidation reactions using urea-hydrogen peroxide; A safe alternative to anhydrous hydrogen peroxide," *Synlett*, 1990, pp. 533-535.

Coulter, A. et al., "Outcomes of referrals to gynaecology outpatient clinics for menstrual problems: an audit of general practice records," *Br. J. Obstet. Gynaecol.*, 1991, 98:789-796.

Denda, M. et al., "*trans*-4-(Aminomethyl)cyclohexane carboxylic acid (T-AMCHA), an anti-fibrinolytic agent, accelerates barrier recovery and prevents the epidermal hyperplasia induced by epidermal injury in hairless mice and humans," *J. Invest. Dermatol.*, 1997, 109:84-90.

Dockeray, C. et al., "The fibrinolytic enzyme system in normal menstuation and excessive uterine bleeding and the effect of tranexamic acid," *Eur. J. Obstet. Gynecol. Reprod. Biol.*, 1987, 24, 309-318.

Dunbar, S. et al., "Cancer treatment with inhibitors of urokinase-type plasminogen activator and plasmin," *Exp. Opin. Invest. Drugs*, 2000, 9(9):2085-2092.

Dunn, C. & Goa, K., "Tranexamic acid, A review of its use in surgery and other indications," *Drugs*, 1999, 57(6):1005-1032.

During, M. et al., "Controlled release of dopamine from a polymeric brain implant: in vivo characterization," *Ann. Neurol.*, 1989, 25:351-356.

Edlund, M. et al., "Reduction of menstrual blood loss in women suffering from idiopathic menorrhagia with a novel antifibrinolytic drug (Kabi 2161)," *Br. J. Obstet. Gynaecol.*, 1995, 102:913-917.

*Encyclopedia of Reagents for Organic Synthesis*, vols. 1-8, L. Paquette, Ed., Table of Contents, John Wiley & Sons, New York, 10 pages (1995).

Fincher, J., "Particle size of drugs and its relationship to absorption and activity," *J. Pharm. Sci.*, 1968, 57(11):1825-1835.

Gleeson, N., "Cyclic changes in endometrial tissue plasminogen activator and plasminogen activator inhibitor type 1 in women with normal menstruation and essential menorrhagia," *Am. J. Obstet. Gynecol.*, 1994, 171:178-183.

Goodson, J., "Dental Applications," Chapter 6 in *Medical Applications of Controlled Release*, vol. II, Langer, R. & Wise, D., Eds., CRC Press, Inc., Boca Raton, FL, pp. 115-138 (1984).

Hoes, C. & Feijen, J., "The application of drug-polymer conjugates in chemotherapy," *Horizons in Biochemsitry and Biophysics*, vol. 9, Drug Carrier Systems, Roerdink, F. et al., Eds., John Wiley & Sons, Inc., New York, pp. 57-109 (1989).

Howard, III, M. et al., "Intracerebral drug delivery in rats with lesion-induced memory deficits," *J. Neurosurg.*, 1989, 71:105-112.

Kayser, M. et al., "Designer yeast': an enantioselective oxidizing reagent for organic synthesis," *Synlett*, 1999, No. 1, pp. 153-158.

Kitamura, K. et al., "Research on the mechanism by which dry skin occurs and the development of an effective compound for its treatment," *J. Soc. Cosmet. Chem. Japan*, 1995, 29(2):133-145.

Kramer, M. et al., "Plasminogen activation by human keratinocytes: Molecular pathways and cell-biological consequences," *Biol. Chem. Hoppe-Seyler*, 1995, 376:131-141.

Langer, R. & Peppas, N., "Chemical and physical structure of polymers as carriers for controlled release of bioactive agents: A review," *J Macromol. Sci. Rev. Macromol Chem. Phys.*, 1983, C23(1):61-126.

Langer, R., "New methods of drug delivery," *Science*, 1990, 249:1527-1533.

Larock, R., *Comprehensive Organic Transformations: A Guide to Functional Group Preparations*, VCH Publishers, Inc., New York, Table of Contents, 20 pages (1989).

Leong, K. & Langer, R., "Polymeric controlled drug delivery," *Adv. Drug Delivery Rev.*, 1987, 1:199-233.

Levy, R. et al., "Inhibition of calcification of bioprosthetic heart valves by local controlled-release diphosphonate," *Science*, 1985, 228:190-192.

Linhardt, R., "Biodegradable polymers for controlled release of drugs," *Controlled Release of Drugs*, Chapter 2, VCH Publishers, pp. 53-95 (1989).

List, B. et al., "The proline-catalyzed direct asymmetric three-component Mannich reaction: Scope, optimization, and application to the highly enantioselective synthesis of 1,2-amino alcohols," *J. Am. Chem. Soc.*, 2002, 124(5):827-833.

Lu, S. & Lu, J-Y., "Dimensionless presentation for drug release from a coated pure drug bead: 2. Experiment," *Int. J. Pharmaceutics*, 1994, 112:117-124.

Maeda, K. & Naganuma, M., "Topical *trans*-4-aminomethylcyclohexanecarboxylic acid prevents ultraviolet radiation-induced pigmentation," *J. Photochem. Photobiol. B*, 1998, 47:136-141.

Manosroi, A., et al., "Stability and release of topical tranexamic acid lipsome formulations," *J. Cosmet. Sci.*, 2002, 53, 375-386.

*Medical Applications of Controlled Release*, vols. I and II, Langer, R. & Wise, D., Eds., CRC Press, Inc., Boca Raton, FL, Table of Contents, 6 pages (1984).

Mulvihill, M. et al., "Benzaldehyde-derived chloroformates and their application towards the synthesis of methoxyfenozide-*N*-[(acyloxy)benzyloxy]carbonyl derivatives," *Tetrahedron Lett.*, 2001, 42:7751-7754.

Mulvihill, M. et al., "Synthesis and application of novel glyoxylate-derived chloroformates," *Synthesis*, 2002, 3:365-370.

Pereira, J. & Phan, T., "Management of bleeding in patients with advanced cancer," *The Oncologist*, 2004, 9:561-570.

Peto, V. et al., "Factors affecting general practitioners' recruitment of patients into a prospective study," *Fam. Practice*, 1993, 10, 207-211.

*Protective Groups in Organic Synthesis*, Second Edition, Greene, T. & Wuts, P., Eds., John Wiley & Sons, Inc., New York, Table of Contents, 4 pages (1991).

*Remington: The Science and Practice of Pharmacy*, 19th Edition, Mack Publishing Co., Easton, PA, Table of Contents, 5 pages (1995).

*Reminton's Pharmaceutical Sciences*, 14th Edition, Mack Publishing Co., Easton, PA, pp. 1626-1627 (1970).

*Remington's Pharmaceutical Sciences*, 17th Edition, Mack Publishing Co., Easton, PA, pp. 1603-1625 (1985).

Renz, M. & Meunier, B., "100 years of Baeyer-Villiger oxidations," *Eur. J. Org. Chem.*, 1999, 4:737-750.

Roff, W. et al., *Handbook of Common Polymers*, Table of Contents, Butterworth & Co., London, 7 pages (1971).

Sidenius, N. & Blasi, F., "The urokinase plasminogen activator system in cancer: Recent advances and implication for prognosis and therapy," *Cancer Metastasis Rev.*, 2003, 22:205-222.

Stonelake, P. et al., "Proteinase inhibitors reduce basement membrane degradation by human breast cancer cell lines," *Br. J. Cancer*, 1997, 75(7):951-959.

Strukul, G., "Transition metal catalysis in the Baeyer-Villiger oxidation of ketones," *Angew. Chem. Int. Ed.*, 1998, 37:1198-1209.

Sun, X. et al., "N-Acyloxymethyl carbamate linked prodrugs of pseudomycins are novel antifungal agents," *Bioorg. Med. Chem. Lett.*, 2001, 11:1875-1879.

Sun, X. et al., "Synthesis and evaluation of novel pseudomycin side-chain analogues. Part 3," *Bioorg. Med. Chem. Lett.*, 2001, 11:3055-3059.

Svahn, C. et al., "Absorption of tranexamic acid as a prodrug in healthy volunteers," *Arzneim.-Forsch./Drug Res.*, 1988, 38(I), No. 5, pp. 735-738.

Svahn, C. et al., "Tranexamic acid derivatives with enhanced absorption," *J. Med. Chem.*, 1986, 29, 448-453.

*Transition Metals in Organic Synthesis*, vol. 1, Beller, M. & Bolm, C., Eds, Table of Contents, Wiley-VCH, New York, 23 pages (1998).

Varma, R. & Naicker, K., "The urea-hydrogen peroxide complex: Solid-state oxidative protocols for hydroxylated aldehydes and ketones (Dakin reaction), nitriles, sulfides, and nitrogen heterocycles," *Org. Lett.*, 1999, 1(2):189-191.

Verma, R. et al., "Osmotically controlled oral drug delivery," *Drug Dev. Ind. Pharm.*, 2000, 26(7):695-708.

Wellington, K. & Wagstaff, A., "Tranexamic acid, A review of its use in the management of menorrhagia," *Drugs*, 63(13):1417-1433.

*Women's Problems in General Practice*, Oxford General Practice Series 4, McPherson, A. & Anderson, A., Eds., Oxford University Press, Oxford, pp. 21-41 (1983).

International Search Report and Written Opinion mailed Dec. 19, 2006, for PCT Application No. PCT/US2006/023873, filed Jun. 20, 2006.

Cundy et al., "XP13512 [(+/−)-1-([(α-Isobutanoyloxyethoxy)carbonyl]aminomethyl)-1-cyclohexane Acetic Acid], A Novel Gabapentin Prodrug: II. Improved Oral Bioavailability, Dose Proportionality, and Colonic Absorption Compared with Gabapentin in Rats and Monkeys," *Journal of Pharmacology and Experimental Therapeutics*, 311(1):324-333 (2004).

Notice of Allowance and Issue Fee Due and Notice of Allowability including Examiner-Initiated Interview Summary, and Examiner's Amendment mailed Jul. 6, 2007 for U.S. Appl. No. 11/455,855, filed Jun. 20, 2006.

Gyurosiova et al., Permeability profiles of m-alkoxysubstituted pyrroldinoethylesters of phenylcarbamic acid across Caco-2 monolayers and human skin. *Pharm. Res* 2002, 19(2), 162-168.

Rha et al., Modulation of biological phenotypes for tumor growth and metastasis by target-specific biological inhibitors in gastric cancer. *Int J Mol Med* 1999, 4(2), 203-12.

Tanaka et al., Effects of tranexamic acid and urokinase on hematogenous metastases of Lewis lung carcinoma in mice. *Invasion Metastasis* 1981, 1(3), 149-157.

Vávrová et al., Biodegradable derivatives of tranexamic acid as transdermal permeation enhances. *J Controlled Release* 2005, 104, 41-49.

* cited by examiner

ACYLOXYALKYL CARBAMATE PRODRUGS OF TRANEXAMIC ACID, METHODS OF SYNTHESIS AND USE

This application is a continuation of U.S. patent application Ser. No. 11/455,855 filed Jun. 20, 2006, now U.S. Pat. No. 7,351,740, which claims benefit of U.S. Provisional Patent Application No. 60/692,625, filed Jun. 20, 2005. Each of these applications is incorporated by reference herein for all purposes.

TECHNICAL FIELD

The disclosure relates to prodrugs of acyloxyalkyl carbamate trans-4-(aminomethyl)-cyclohexanecarboxylic acid, pharmaceutical compositions thereof, methods of making prodrugs of trans-4-(aminomethyl)-cyclohexane-carboxylic acid, and methods of using prodrugs of trans-4-(aminomethyl)-cyclohexanecarboxylic acid and pharmaceutical compositions thereof to treat various diseases or disorders. The disclosure also relates to such prodrugs suitable for oral and topical administration including for oral administration using sustained release dosage forms.

BACKGROUND

Tranexamic acid (1) (trans-4-(aminomethyl)-cyclohexanecarboxylic acid, Cyklokapron®):

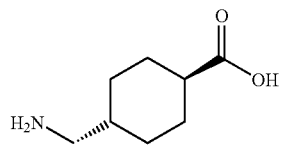

(1)

is an antifibrinolytic agent that reversibly blocks lysine binding sites on plasminogen and plasmin, and acts to prevent proteolytic degradation of fibrin clots which form in the normal physiologic process of hemostasis. Both plasminogen and plasmin are activators of fibrinolysis and active clot-lysing agents. Tranexamic acid thus helps to stabilize fibrin clots, which in turn maintains coagulation and helps to control bleeding.

Tranexamic acid is used clinically to control excess bleeding, for example, heavy bleeding associated with cardiac surgery, upper gastrointestinal hemorrhage, blood loss in patients with advanced cancer (both acute hemorrhagic events and low-volume chronic bleeding), excessive bleeding that occurs during dental procedures in hemophiliacs, and for heavy bleeding during menstruation, i.e., menorrhagia (see Wellington and Wagstaff, *Drugs*, 2003, 63, 1417-1433; Dunn and Goa, *Drugs*, 1999, 57, 1005-1032; Pereira and Phan, *The Oncologist*, 2004, 9, 561-570).

The importance of the plasminogen/plasmin proteolytic cascade in epidermal biology and pathophysiology is also well appreciated (Kramer et al., *Biol. Chem. Hoppe-Seylar*, 1995, 3, 131-141). Disruption of the stratum corneum by mechanical or chemical injury induces epidermal proteolytic activity. Topical treatment of human or rodent skin with tranexamic acid significantly accelerates barrier recovery and greatly decreases epidermal hyperplasia, suggesting a role for plasmin inhibitory compounds in promoting epidermal wound healing (Denda et al., *J. Invest. Dermatol.*, 1997, 109, 84-90; Kitamura et al., *J. Soc. Cosmet. Chem.*, 1995, 29, 133-145). Exposure of human skin to ultraviolet radiation causes erythema and pigmentation, with pigmentation resulting from increased melanin production. A role for plasmin in contributing to increased production of arachidonic acid and prostaglandin metabolites in skin following U.V. exposure has also been demonstrated. Topical application of tranexamic acid prevents U.V.-induced pigmentation in vivo through dose-dependent reduction in prostaglandin production (Maeda and Naganuma, *J. Photochem. Photobiol. B*, 1998, 47, 136-141; Manosroi et al., *J. Cosmet. Sci.*, 2002, 53, 375-386; Suetsugu et al., U.S. Pat. No. 5,690,914).

The plasminogen activation system is also a predominant protease pathway responsible for extracellular matrix (ECM) degradation. Cancer dissemination and metastasis is synonymous with invasive cell migration, a process in which the ECM plays the dual role of the substratum on which the cells move as well as the physical obstacle that the cells have to surpass. To degrade the physical obstacle that the ECM poses in the direction of migration, cells use proteolytic enzymes such as plasminogen and plasmin capable of hydrolyzing the ECM components (Stonelake et al., *Br. J. Cancer*, 1997, 75, 951-959; Dunbar et al., *Expert Opin. Investig. Drugs*, 2000, 9, 2085-2092; Sidenius and Blasi, *Cancer Metastasis Rev.*, 2003, 22, 205-222). Plasmin inhibitory compounds such as tranexamic acid, therefore, show utility as anti-metastatic agents either alone or in combination with cytotoxic anticancer agents (Tsutsumi and Konishi, *Jpn. Kokai Tokkyo Koho*, 2002114673).

Menorrhagia is defined as blood loss >80 mL per menstrual cycle and affects many women and represents a significant health problem. Prevalence rates are believed to be similar across the Western world, and in the U.K. at least one in 20 women aged between 34 and 49 years will consult their general practitioners because of menstrual disorders. Menorrhagia accounts for 60% of primary-care consultations for menstrual problems and 12% of all gynecology referrals (Peto et al., *Fam. Pract.*, 1993, 10, 207-211; McPherson and Andersson, eds., *Women's problems in general practice*, Oxford: Oxford University Press, 1983, pp 21-41; Bradlow et al., *Patterns of referral*, Oxford: Oxford Health Services Research Unit, 1992). While various pathological mechanisms may contribute to the cause of menorrhagia, approximately 50% of women with heavy menstrual blood loss have no underlying anatomical or endocrinological abnormality. In such women fibrinolytic activity in utero is higher than in women with normal menstrual blood loss, with this increased fibrinolysis resulting from elevated levels of endometrium-derived plasmin and plasminogen activators (Gleeson, *Am. J. Obstet. Gynecol.*, 1994, 171, 178-183; Dockeray et al., *Eur. J. Obstet. Gynecol. Reprod. Biol.*, 1987, 24, 309-318).

Despite the availability of clinically effective antifibrinolytic agents such as tranexamic acid (which has been shown to reduce menstrual blood loss by ~50%), approximately 60% of women with menorrhagia undergo hysterectomy within 5 years of referral to a gynecologist (Coulter et al., *Br. J. Obstet. Gynaecol.*, 1991, 98, 789-796). Women suffering from menorrhagia are typically treated orally with tranexamic acid concurrently with menstruation (4-7 days). Doses of 500-1500 mg tranexamic acid tablets administered three or four times daily are typical. Intravenous dosage formulations are also available for use as a continuous infusion in the surgical setting. The requirement for frequent daily oral administration results from the suboptimal pharmacokinetic properties of tranexamic acid, which includes modest oral bioavailability (~30%) and a rapid terminal elimination half-life of ~2 hours.

Sustained released oral dosage formulations are a conventional solution to the problem of rapid systemic drug clearance, as is well known in the art (See, e.g., "Remington's Pharmaceutical Sciences," Philadelphia College of Pharmacy and Science, 19th Edition, 1995). Osmotic delivery systems are also recognized methods for sustained drug delivery (see e.g., Verma et al., *Drug Dev. Ind. Pharm.*, 2000, 26, 695-708). Successful application of these technologies depends on the drug of interest having an effective level of absorption from the large intestine (also referred to herein as the colon), where the dosage form spends a majority of its time during its passage through the gastrointestinal tract. Tranexamic acid is poorly absorbed following rectal administration in humans (Almer et al., *J. Clin. Pharm.*, 1992, 32, 49-54), consistent with limited permeability of the drug across the colonic mucosa. Development of an oral controlled release formulation for tranexamic acid should considerably improve the convenience, efficacy and side effect profile of tranexamic acid therapy. However, the rapid passage of conventional dosage forms through the proximal absorptive region of the small intestine has thus far prevented the successful application of sustained release technologies to this drug. Heasley et al. have described delayed release oral formulations of tranexamic acid based on the use of enteric polymer coatings that are designed to retard the dissolution of the drug by 1-2 hours until the dosage form has passed from the stomach to the small intestine (U.S. Patent Application No. 2005/002825). Such formulations are said to reduce the adverse gastrointestinal reactions that may accompany oral tranexamic acid therapy (including nausea, vomiting, diarrhea, dyspepsia and cramping). However these formulations would not be expected to substantially alter the elimination half-life of the drug, and hence overcome the requirement for frequent daily dosing.

There is a significant need for new prodrugs of tranexamic acid that are well absorbed in the large intestine and hence suitable for oral sustained release formulations, thus improving the convenience, efficacy and side effect profile of antifibrinolytic therapy. Moreover, since the zwitterionic character of tranexamic acid limits the permeability of the compound across the epidermal barrier, there is also a need for more lipophilic prodrug derivatives of tranexamic acid which would provide for more effective topical administration in the treatment of skin disorders such as wound healing, epidermal hyperplasia, skin roughening, unwanted skin pigmentation, etc.

One solution to the incomplete gastrointestinal absorption of tranexamic acid is through design of prodrug derivatives (see Svahn et al., *J. Med. Chem.*, 1986, 29, 448-453; Svahn et al., European Patent No. 0 079 872 B1; Svahn et al., U.S. Pat. No. 4,483,867; Jonsson, International Publication No. WO94/15904; Svahn et al., *Arzneim-Forsch.*, 1988, 38, 735-738; Edlund et al., *Br. J. Obstet. Gynaecol.*, 1995, 102, 913-917). The prodrug 1-(ethoxycarbonyl)oxyethyl trans-4-(aminomethyl)-cyclohexanecarboxylate (i.e., Kabi 2161) showed markedly improved oral bioavailability of tranexamic acid in human patients, and was effective in reducing menstrual blood loss in women suffering from idiopathic menorrhagia.

SUMMARY

The needs described above, among other needs, can be satisfied by the disclosure herein of acyloxyalkyl carbamate prodrugs of tranexamic acid, pharmaceutical compositions of acyloxyalkyl carbamate prodrugs of tranexamic acid, methods of making acyloxyalkyl carbamate prodrugs of tranexamic acid, and methods of using acyloxyalkyl carbamate prodrugs of tranexamic acid and/or pharmaceutical compositions thereof to treat various medical pathologies. The disclosure also provides prodrugs suitable for oral and topical administration including for oral administration using sustained release dosage forms.

In one aspect, compounds of Formula (I) are provided,

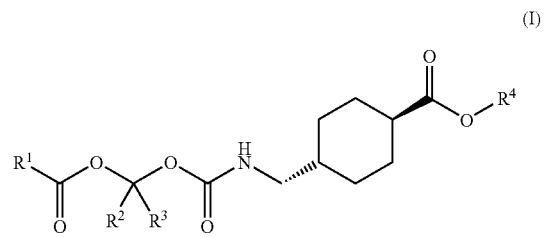

(I)

pharmaceutically acceptable salts thereof, and pharmaceutically acceptable solvates of any of the foregoing, wherein:

$R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

$R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring; and $R^4$ is selected from hydrogen, alkyl, substituted alkyl, aryl, substituted aryl, arylalkyl, substituted arylalkyl, aryldialkylsilyl, substituted aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, trialkylsilyl, and substituted trialkylsilyl.

In another aspect, compounds of Formula (II) are provided,

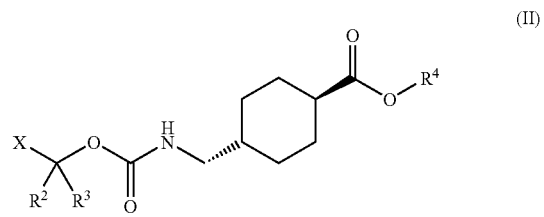

(II)

pharmaceutically acceptable salts thereof, and pharmaceutically acceptable solvates of any of the foregoing, wherein:

X is selected from fluoro, chloro, bromo, iodo, and $R^{20}SO_3$— wherein $R^{20}$ is selected from $C_{1-6}$ alkyl, $C_{5-7}$ aryl, and substituted $C_{5-7}$ aryl; and $R^2$, $R^3$ and $R^4$ are as defined above.

In another aspect, methods of synthesizing a compound of Formula (I) are provided, comprising:

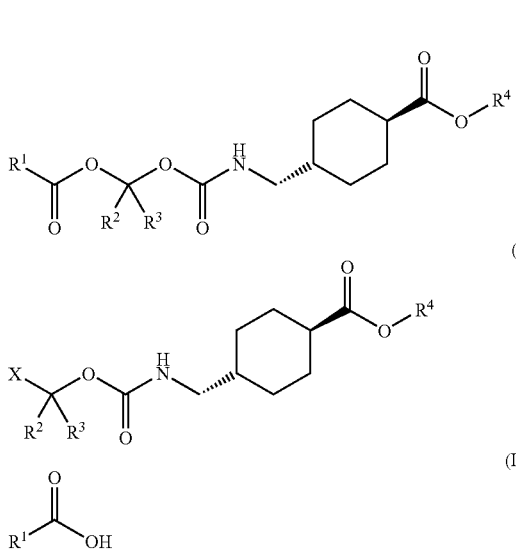

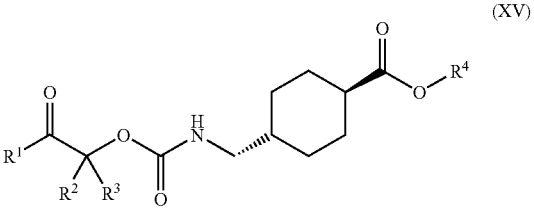

contacting a compound of Formula (II), a compound of Formula (III) and at least one equivalent of a reactant selected from an organic base, an inorganic base, and combinations thereof, to provide a compound of Formula (I), pharmaceutically acceptable salts thereof, and pharmaceutically acceptable solvates of any of the foregoing, wherein:

X, $R^1$, $R^2$, $R^3$ and $R^4$ are as defined above.

In another aspect, methods of synthesizing a compound of Formula (I) are provided, comprising:

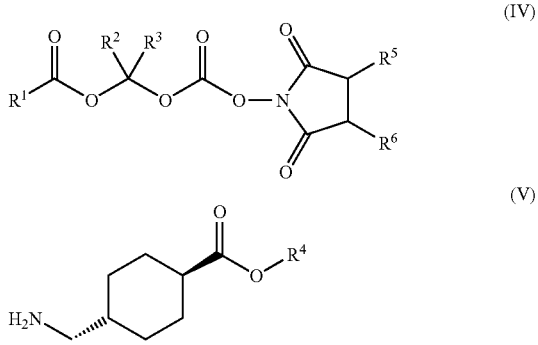

contacting a compound of Formula (IV) with a compound of Formula (V) to provide a compound of Formula (I), pharmaceutically acceptable salt thereof, or a pharmaceutically acceptable solvate of any of the foregoing, wherein:

$R^5$ and $R^6$ are independently selected from hydrogen, acylamino, acyloxy, alkoxycarbonylamino, alkoxycarbonyloxy, alkyl, substituted alkyl, alkoxy, substituted alkoxy, aryl, substituted aryl, arylalkyl, substituted arylalkyl, carbamoyloxy, dialkylamino, heteroaryl, substituted heteroaryl, hydroxy, and sulfonamido, or $R^5$ and $R^6$ together with the atoms to which they are bonded form a substituted cycloalkyl, substituted cycloheteroalkyl, or substituted aryl ring; and $R^1$, $R^2$, $R^3$ and $R^4$ are as defined above.

In another aspect, methods of synthesizing a compound of Formula (I) are provided, comprising contacting a compound of Formula (XV) with an oxidant, to provide a compound of Formula (I), or pharmaceutically acceptable salts thereof, or pharmaceutically acceptable solvates of any of the foregoing,

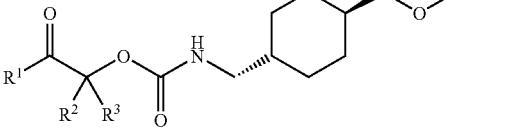

wherein $R^1$, $R^2$, $R^3$ and $R^4$ are as defined above.

In another aspect, pharmaceutical compositions comprising at least one pharmaceutically acceptable vehicle and a therapeutically effective amount of at least one compound of Formula (I), a pharmaceutically acceptable salt thereof, or a pharmaceutically acceptable solvate of any of the foregoing, are provided.

In another aspect, oral dosage forms, comprising at least one tranexamic acid prodrug of Formula (I), a pharmaceutically acceptable salt thereof, or a pharmaceutically acceptable solvate of any of the foregoing, are provided.

In another aspect, sustained release oral dosage forms, comprising at least one prodrug of Formula (I), a pharmaceutically acceptable salt thereof, or a pharmaceutically acceptable solvate of any of the foregoing, are provided.

In another aspect, topical dosage forms are provided, comprising at least one compound of Formula (I), a pharmaceutically acceptable salt thereof, or a pharmaceutically acceptable solvate of any of the foregoing, formulated in a pharmaceutically acceptable topical vehicle.

In another aspect, methods of topically administering to a patient at least one compound of Formula (I), a pharmaceutically acceptable salt thereof, or a pharmaceutically acceptable solvate of any of the foregoing, are provided, the methods comprising applying the at least one compound of Formula (I) onto a surface area of the patient.

In another aspect, methods are provided for treating excessive bleeding, including heavy bleeding associated with cardiac surgery, upper gastrointestinal hemorrhage, blood loss in patients with advanced cancer, excessive bleeding that occurs during dental procedures, for example in hemophiliacs, and heavy bleeding during menstruation, i.e., menorrhagia. The methods include administering to a patient in need of such treatment a therapeutically effective amount of at least one compound of Formula (I), a pharmaceutically acceptable salt thereof, or a solvate of any of the foregoing and/or a pharmaceutical composition thereof.

In another aspect, methods are provided for treating skin disorders such as wound healing, epidermal hyperplasia, skin roughening and unwanted skin pigmentation. The methods include topically administering to a patient in need of such treatment a therapeutically effective amount of at least one compound of Formula (I), a pharmaceutically acceptable salt thereof, or a solvate of any of the foregoing, and/or a pharmaceutical composition thereof.

In another aspect, methods are provided for treating tumor metastasis in a patient suffering from a disorder, such as a malignant disorder. These methods include administering to a patient in need of such treatment a therapeutically effective amount of at least one compound of Formula (I), a pharmaceutically acceptable salt thereof, or a solvate of any of the foregoing and/or a pharmaceutical composition thereof, either alone or in combination with one or more cytotoxic agents.

In another aspect, methods are provided for achieving a sustained therapeutic or prophylactic concentration of tranexamic acid in the systemic circulation of a patient comprising orally administering at least one compound of Formula (I), a pharmaceutically acceptable salt thereof, or a solvate of any of the foregoing to the patient.

BRIEF DESCRIPTION OF THE DRAWINGS

The skilled artisan will understand that the drawings, described herein, are for illustration purposes only. The drawings are not intended to limit the scope of the present disclosure.

DETAILED DESCRIPTION

Definitions

Figure 1:
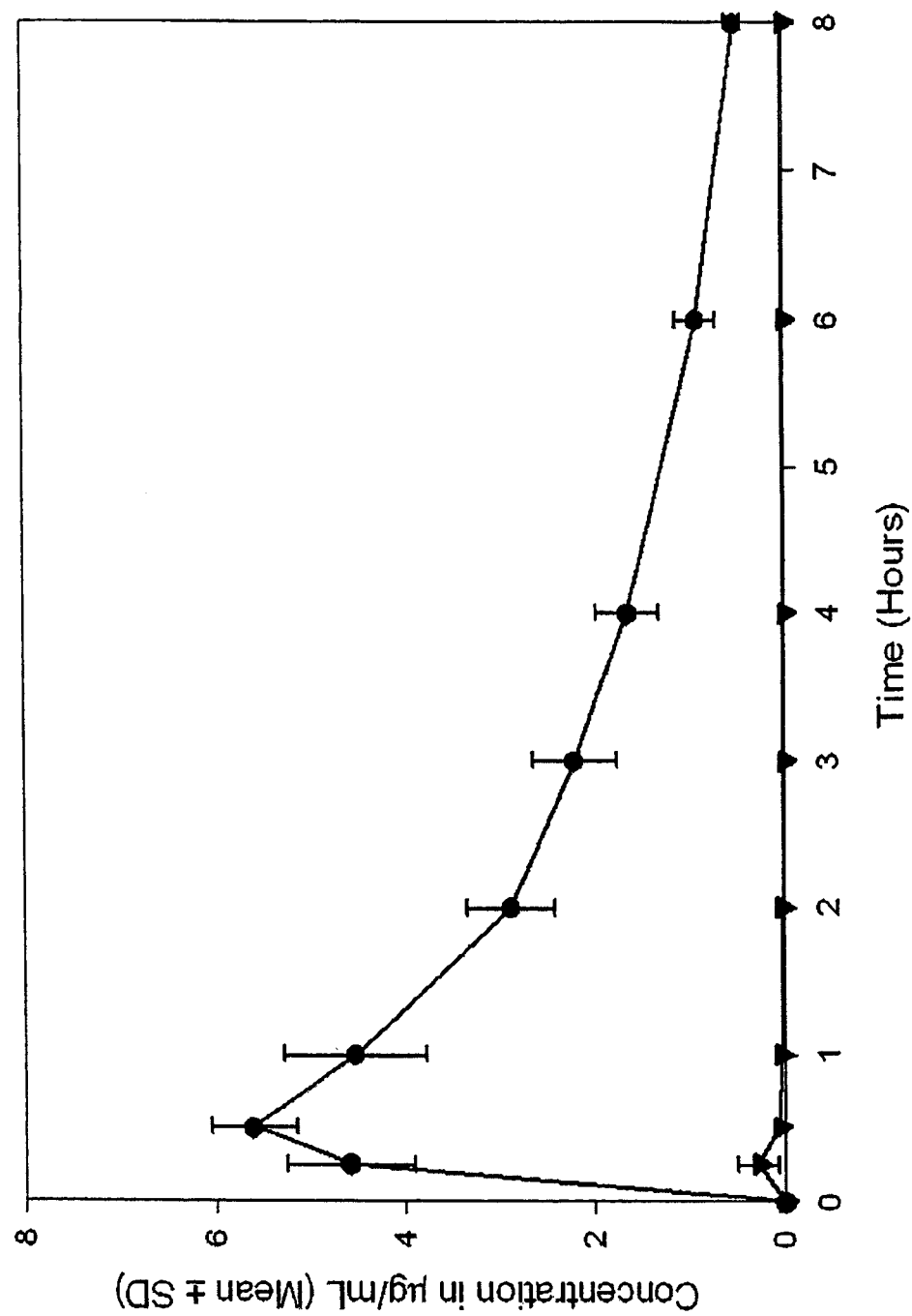
FIG. 1 shows the pharmacokinetics profile of released tranexamic acid (-●-) and remaining tranexamic acid prodrug 13 (-▼-) following intracolonic administration of tranexamic acid prodrug 13.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the embodiments are approximations, the numerical values set forth in the specific examples are reported as precisely as possible. Any numerical values, however, inherently contain certain errors necessarily resulting from in the error inherent in measurements.

The section headings used herein are for organizational purposes only and are not to be construed as limiting the subject matter disclosed.

To the extent the definitions of terms in the publications, patents, and patent applications incorporated herein by reference are not the same as the definitions set forth in this specification, the definitions in this specification control for the entire specification, including the claims. Any other definitions in the publications, patents, and patent applications incorporated herein by reference that are not explicitly provided in this specification apply only to the embodiments discussed in the publications, patents, and patent applications incorporated herein by reference.

A dash ("-") that is not between two letters or symbols is used to indicate a point of attachment for a substituent. For example, —$CONH_2$ is attached through the carbon atom.

"Acyl" by itself or as part of another substituent refers to a radical —$C(O)R^{30}$ where $R^{30}$ is hydrogen, alkyl, heteroalkyl, cycloalkyl, cycloheteroalkyl, cycloalkylalkyl, cyclohetereoalkylalkyl, aryl, heteroaryl, arylalkyl, or heteroarylalkyl, which may be substituted, as defined herein. Examples of acyl groups include, but are not limited to, formyl, acetyl, cyclohexylcarbonyl, cyclohexylmethylcarbonyl, benzoyl, benzylcarbonyl. In certain embodiments, an acyl group is $C_{1-3}$ acyl.

"Acylamino" by itself or as part of another substituent refers to a radical —$NR^{31}C(O)R^{32}$, where $R^{31}$ and $R^{32}$ are independently hydrogen, alkyl, cycloalkyl, cycloheteroalkyl, aryl, arylalkyl, heteroalkyl, heteroaryl, or heteroarylalkyl, which may be substituted as defined herein. Examples of acylamino groups include, but are not limited to, formamido, acetamido and benzamido.

"1-Acyloxy-Alkyl Carbamate" refers to an N-1-(acyloxy) alkoxycarbonyl derivative of tranexamic acid as encompassed by compounds of Formula (I) disclosed herein.

"Alkyl" by itself or as part of another substituent refers to a saturated or unsaturated, branched or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group comprises from 1 to 20 carbon atoms, in certain embodiments, from 1 to 6 carbon atoms, and in certain embodiments, from 1 to 3 carbon atoms. In certain embodiments, alkyl is $C_{1-6}$ alkyl, $C_{1-4}$ alkyl, $C_{1-3}$ alkyl, methyl, ethyl, n-propyl, isopropyl, n-butyl, isobutyl, sec-butyl, tert-butyl, or allyl.

"Alkanyl" by itself or as part of another substituent refers to a saturated branched or straight-chain alkyl radical derived by the removal of one hydrogen atom from a single carbon atom of a parent alkane. Examples of alkanyl groups include, but are not limited to, methanyl, ethanyl, propanyls such as propan-1-yl, propan-2-yl (isopropyl), etc.; butanyls such as butan-1-yl, butan-2-yl (sec-butyl), 2-methyl-propan-1-yl (isobutyl), 2-methyl-propan-2-yl (t-butyl), etc.; and the like.

"Alkenyl" by itself or as part of another substituent refers to an unsaturated branched or straight-chain alkyl radical having at least one carbon-carbon double bond derived by the removal of one hydrogen atom from a single carbon atom of a parent alkene. The group may be in either the cis or trans conformation about the double bond(s). Examples of alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, etc.; and the like.

"Alkynyl" by itself or as part of another substituent refers to an unsaturated branched or straight-chain alkyl radical having at least one carbon-carbon triple bond derived by the removal of one hydrogen atom from a single carbon atom of a parent alkyne. Examples of alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyloxy" by itself or as part of another substituent refers to a radical —OC(O)R$^{33}$, where R$^{33}$ is alkyl, cycloalkyl, cycloheteroalkyl, aryl, arylalkyl, heteroalkyl, heteroaryl, or heteroarylalkyl, which may be substituted, as defined herein. Examples of acyloxy groups include, but are not limited to, acetoxy, isobutyroyloxy, benzoyloxy, phenylacetoxy.

"Alkoxy" by itself or as part of another substituent refers to a radical —OR$^{34}$ where R$^{34}$ is alkyl, cycloalkyl, cycloalkylalkyl, aryl, or arylalkyl, which may be substituted, as defined herein. Examples of alkoxy groups include, but are not limited to, methoxy, ethoxy, propoxy, butoxy, cyclohexyloxy.

"Alkoxycarbonyl" by itself or as part of another substituent refers to a radical —C(O)OR$^{35}$ where R$^{35}$ is an alkyl or substituted alkyl group, as defined herein. Examples of alkoxycarbonyl groups include, but are not limited to, methoxycarbonyl, ethoxycarbonyl, propoxycarbonyl, butoxycarbonyl. In certain embodiments, an alkoxycarbonyl group is $C_{1-3}$ alkoxycarbonyl.

"Alkoxycarbonylamino" by itself or as part of another substituent refers to a radical —NR$^{36}$C(O)—OR$^{37}$ where R$^{36}$ represents an alkyl, substituted alkyl, cycloalkyl, or substituted cycloalkyl group and R$^{37}$ is alkyl, cycloalkyl, cycloheteroalkyl, aryl, arylalkyl, heteroalkyl, heteroaryl, or heteroarylalkyl, which may be substituted, as defined herein. Examples of alkoxycarbonylamino groups include, but are not limited to, methoxycarbonylamino, tert-butoxycarbonylamino, and benzyloxycarbonylamino.

"Alkoxycarbonyloxy" by itself or as part of another substituent refers to a radical —OC(O)—OR$^{38}$ where R$^{38}$ is an alkyl, substituted alkyl, cycloalkyl, or substituted cycloalkyl group, as defined herein. Examples of alkoxyarbonyloxy groups include, but are not limited to, methoxycarbonyloxy, ethoxycarbonyloxy, and cyclohexyloxycarbonyloxy.

"Alkylamino" by itself or as part of another substituent refers to a radical —NHR$^{39}$ where R$^{39}$ is an alkyl, substituted alkyl, cycloalkyl, or substituted cycloalkyl group, as defined herein. In certain embodiments, an alkylamino group is $C_{1-3}$ alkylamino.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene. In certain embodiments, an aryl group may have from 5 to 20 carbon atoms, and in certain embodiments, from 5 to 12 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein. In certain embodiments, aryl is $C_{6-10}$ aryl or phenyl.

"Arylalkyl" by itself or as part of another substituent refers to an acyclic alkyl radical in which one of the hydrogen atoms bonded to a carbon atom, typically a terminal or Sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$. In certain embodiments, arylalkyl is $C_{7-16}$ arylalkyl or benzyl.

"Aryldialkylsilyl" by itself or as part of another substituent refers to the radical —SiR$^{40}$R$^{41}$R$^{42}$ where one of R$^{40}$, R$^{41}$, and R$^{42}$ is aryl or substituted aryl as defined herein and the other two of R$^{40}$, R$^{41}$, and R$^{42}$ are alkyl or substituted alkyl, as defined herein. In certain embodiments, an aryldialkylsilyl group is $C_{7-14}$ aryldialkylsilyl.

"AUC" is the area under the plasma drug concentration-versus-time curve extrapolated from zero time to infinity.

"$C_{max}$" is the highest drug concentration observed in plasma following an extravascular dose of drug.

"Carbamoyl" by itself or as part of another substituent refers to the radical —C(O)NR$^{43}$R$^{44}$ where R$^{43}$ and R$^{44}$ are independently hydrogen, alkyl, substituted alkyl, cycloalkyl, substituted cycloalkyl, aryl, or substituted aryl, as defined herein.

"Carbamoyloxy" by itself or as part of another substituent refers to a radical —OC(O)$_2$NR$^{43}$R$^{44}$ where R$^{45}$ and R$^{46}$ are independently selected from hydrogen, alkyl, cycloalkyl, cycloheteroalkyl, aryl, arylalkyl, heteroalkyl, heteroaryl, and heteroarylalkyl, which may be substituted, as defined herein, or R$^{45}$ and R$^{46}$ together with the atoms to which they are bonded form a cycloheteroalkyl or heteroaryl ring.

"Cleave" refers to breakage of chemical bonds and is not limited to chemical or enzymatic reactions or mechanisms unless clearly intended by the context.

"Compounds" refers to compounds encompassed by structural Formulae (I)-(XIX) disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers, i.e., geometric isomers, enantiomers and diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and other stereoisomeric mixtures. Enantiomeric and stereoisomeric mixtures may be resolved into their component enantiomers or stereoisomers using separation techniques or stereocontrolled synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass found in nature. Examples of isotopes that may be incorporated into the compounds disclosed herein include, but are not limited to, $^2$H, $^3$H, $^{11}$C, $^{13}$C, $^{14}$C, $^{15}$N, $^{17}$O, $^{18}$O, etc. Compounds may exist in unsolvated forms as well as solvated forms, including hydrated forms and as N-oxides. In general, compounds may be hydrated, solvated, or N-oxides. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, an asterisk (*) indicates the point of attachment of the partial structure to the rest of the molecule.

"Cycloalkoxycarbonyl" by itself or as part of another substituent refers to a radical —C(O)OR$^{47}$ where R$^{47}$ represents an cycloalkyl or substituted cycloalkyl group as defined herein. Examples of cycloalkoxycarbonyl groups include, but are not limited to, cyclobutyloxycarbonyl, cyclohexyloxycarbonyl.

"Cycloalkyl" by itself or as part of another substituent refers to a partially saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane. In certain embodiments, a cycloalkyl group is $C_{3-15}$ cycloalkyl, and in certain embodiments, $C_{5-12}$ cycloalkyl. In certain embodiments, a cycloalkyl group is $C_{3-7}$ cycloalkyl or cyclohexyl.

"Cycloheteroalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S and Si. Where a specific level of saturation is intended, the nomenclature "cycloheteroalkanyl" or "cycloheteroalkenyl" is used. Examples of cycloheteroalkyl groups include, but are not limited to, groups derived from epoxides, azirines, thiiranes, imidazolidine, morpholine, piperazine, piperidine, pyrazolidine, pyrrolidine, quinuclidine.

"Dialkylamino" by itself or as part of another substituent refers to the radical —NR$^{48}$R$^{49}$ where R$^{48}$ and R$^{49}$ are independently alkyl, substituted alkyl, cycloalkyl, substituted cycloalkyl, cycloheteroalkyl, substituted cycloheteroalkyl, arylalkyl, substituted arylalkyl, heteroalkyl, substituted heteroalkyl, heteroarylalkyl, or substituted heteroarylalkyl, or R$^{48}$ and R$^{49}$ together with the nitrogen to which they are attached form a cycloheteroalkyl or substituted cycloheteroalkyl ring. In certain embodiments, a dialkylamino group is $C_{1-3}$ dialkylamino.

"1-Haloalkyl carbamate" refers to an N-1-haloalkoxycarbonyl derivative of tranexamic acid as encompassed by compounds of Formula (II) disclosed herein.

"Heteroalkyl" by itself or as part of another substituent refer to an alkyl group in which one or more of the carbon atoms (and any associated hydrogen atoms) are independently replaced with the same or different heteroatomic groups. Examples of heteroatomic groups include, but are not limited to, —O—, —S—, —O—O—, —S—S—, —O—S—, —NR$^{50}$R$^{51}$—, =N—N=, —N=N—, —N=N—NR$^{52}$R$^{53}$, —PR$^{54}$—, —P(O)$_2$—, —POR$^{55}$—, —O—P(O)$_2$—, —SO—, —SO$_2$—, —SnR$^{56}$R$^{57}$—, where R$^{50}$, R$^{51}$, R$^{52}$, R$^{53}$, R$^{54}$, R$^{55}$, R$^{56}$, and R$^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, or substituted heteroarylalkyl. Where a specific level of saturation is intended, the nomenclature "heteroalkanyl," "heteroalkenyl," or "heteroalkynyl" is used.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which may be aromatic or non-aromatic in which at least one ring atom is a heteroatom. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene. In certain embodiments, a heteroaryl group is from 5- to 20-membered heteroaryl, and in certain embodiments from 5- to 10-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Immediately preceding embodiments" means the embodiments disclosed in the same paragraph.

"Parent aromatic ring system" refers to an unsaturated cyclic or polycyclic ring system having a conjugated π electron system. Included within the definition of "parent aromatic ring system" are fused ring systems in which one or more of the rings are aromatic and one or more of the rings are saturated or unsaturated, such as, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene.

"Patient" includes mammals, such as for example, humans.

"Pharmaceutical composition" refers to at least one compound and a pharmaceutically acceptable vehicle, with which the compound is administered to a patient.

"Pharmaceutically acceptable" refers to approved or approvable by a regulatory agency of the Federal or a state government or listed in the U.S. Pharmacopoeia or other generally recognized pharmacopoeia for use in animals, including humans.

"Pharmaceutically acceptable salt" refers to a salt of a compound which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound of the present disclosure may be administered to a patient and which does not destroy the pharmacological activity thereof and which is nontoxic when administered in doses sufficient to provide a therapeutically effective amount of the compound.

"Preventing" or "prevention" refers to a reduction in risk of acquiring a disease or disorder, i.e., causing at least one of the clinical symptoms of the disease not to develop in a patient that may be exposed to or predisposed to the disease but does not yet experience or display symptoms of the disease.

"Prodrug" refers to a derivative of a drug molecule that requires a transformation within the body to release the active drug. Prodrugs can be, although not necessarily, pharmacologically inactive until converted to the parent drug.

"Promoiety" refers to a form of protecting group that when used to mask a functional group within a drug molecule converts the drug into a prodrug. For example, the promoiety may be attached to the drug via bond(s) that are cleaved by enzymatic or non-enzymatic means in vivo.

"Protecting group" refers to a grouping of atoms, which when attached to a reactive group in a molecule masks, reduces, or prevents that reactivity. Examples of protecting groups can be found in Green et al., "Protective Groups in Organic Chemistry," (Wiley, 2nd ed. 1991) and Harrison et al., "Compendium of Synthetic Organic Methods," Vols. 1-8 (John Wiley and Sons, 1971-1996). Examples of amino protecting groups include, but are not limited to, formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC). Examples of hydroxy protecting groups include, but are not limited to, those in which the hydroxy group is either acylated or alkylated such as benzyl, and trityl ethers as well as alkyl ethers, tetrahydropyranyl ethers, trialkylsilyl ethers, and allyl ethers.

"Solvate" refers to a molecular complex of a compound with one or more solvent molecules in a stoichiometric or non-stoichiometric amount. Such solvent molecules are those commonly used in the pharmaceutical art, which are known to be innocuous to the recipient, e.g., water, ethanol, and the like. A molecular complex of a compound or moiety of a compound and a solvent can be stabilized by non-covalent intra-molecular forces such as, electrostatic forces, van der Waals forces, or hydrogen bonds. The term "hydrate" refers to a complex where the one or more solvent molecules are water including monohydrates and hemi-hydrates.

"Substantially one enantiomer" refers to a compound containing 1 or more stereogenic centers such that the enantiomeric excess (e.e.) of the compound is at least about 90%, in certain embodiments greater than about 95%, in certain embodiments greater than about 98%, and in certain embodiments greater than about 99%.

"Substituted" refers to a group in which one or more hydrogen atoms are independently replaced with the same or different substituent(s). Example of substituents include, but are not limited to, -M, —$R^{60}$, —$O^-$ (—OH), =O, —$OR^{60}$, —$SR^{60}$, —$S^-$ (—SH), =S, —$NR^{60}R^{61}$, =$NR^{60}$, —$CF_3$, —CN, —OCN, —SCN, —NO, —$NO_2$, =$N_2$, —$N_3$, —S(O)$_2$O$^-$, —S(O)$_2$OH, —S(O)$_2$R$^{60}$, —OS(O)$_2$O$^-$—, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, NC(O)R$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is a halogen; R$^{60}$, R$^{61}$, R$^{62}$, and R$^{63}$ are independently selected from hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl, and substituted heteroaryl, or when bonded to a nitrogen atom, R$^{60}$ and R$^{61}$ together with the nitrogen atom to which they are bonded form a cycloheteroalkyl or substituted cycloheteroalkyl ring; and R$^{62}$ and R$^{63}$ are independently selected from hydrogen, alkyl, substituted alkyl, aryl, cycloalkyl, substituted cycloalkyl, cycloheteroalkyl, substituted cycloheteroalkyl, aryl, substituted aryl, heteroaryl, and substituted heteroaryl, or when bonded to a nitrogen atom, R$^{62}$ and R$^{63}$ together with the nitrogen atom to which they are bonded form a cycloheteroalkyl or substituted cycloheteroalkyl ring. In certain embodiments, substituents include -M, —R$^{60}$, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O)$_2$O$^-$, —OS(O)$_2$R$^6$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, C(O)O$^{31}$, and —NR$^{62}$C(O)NR$^{60}$R$^{61}$, where R$^{60}$, R$^{61}$, and R$^{62}$ are as defined above. In other embodiments, substituents may be chosen from -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —C(O)O$^-$, where R$^{60}$ and R$^{61}$ are as defined above. In yet other embodiments, substituents include -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —OP(O)(OR$^{60}$)(OR$^{61}$), —C(O)R$^{60}$, —C(O)OR$^{60}$, and —C(O)O$^-$, where R$^{60}$ and R$^{61}$ are as defined above. In certain embodiments, each substituent is independently selected from C$_{1-3}$ alkyl, —OH, —NH$_2$, —SH, C$_{1-3}$ alkoxy, C$_{1-3}$ acyl, C$_{1-3}$ thioalkyl, C$_{1-3}$ alkoxycarbonyl, C$_{1-3}$ alkylamino, and C$_{1-3}$ dialkylamino, as defined herein.

"Sulfonamido" by itself or as part of another substituent refers to a radical —NR$^{65}$S(O)$_2$R$^{66}$, where R$^{65}$ is alkyl, substituted alkyl, cycloalkyl, cycloheteroalkyl, aryl, substituted aryl, arylalkyl, heteroalkyl, heteroaryl, or heteroarylalkyl, and R$^{66}$ is hydrogen, alkyl, cycloalkyl, cycloheteroalkyl, aryl, arylalkyl, heteroalkyl, heteroaryl, or heteroarylalkyl, which may be substituted, as defined herein. Examples of sulfonamido groups include, but are not limited to, methanesulfonamido, benzenesulfonamido, and p-toluenesulfonamido.

"Thioalkyl" by itself or as part of another substituent refers to a radical —SR$^{67}$ where R$^{67}$ is alkyl or substituted alkyl, as defined herein. In certain embodiments, a thioalkyl group is C$_{1-3}$ thioalkyl.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder.

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. The "therapeutically effective amount" may vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate amount in any given instance may be readily ascertained by those skilled in the art or capable of determination by routine experimentation.

"Trialkylsilyl" by itself or as part of another substituent refers to a radical —SiR$^{68}$R$^{69}$R$^{70}$ where R$^{68}$R$^{69}$, and R$^{70}$ are independently selected from alkyl and substituted alkyl, as defined herein. In certain embodiments, a trialkylsilyl group is C$_{3-12}$ trialkylsilyl.

Reference is now be made in detail to embodiments of the present disclosure. While certain embodiments of the present disclosure are described, it will be understood that it is not intended to limit the embodiments of the present disclosure to the disclosed embodiments. To the contrary, reference to embodiments of the present disclosure is intended to cover alternatives, modifications, and equivalents as may be included within the spirit and scope of the embodiments of the present disclosure as defined by the appended claims.

Compounds

Certain embodiments of the present disclosure provide a compound of Formula (I)"

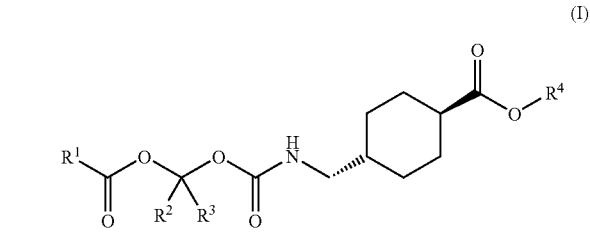

(I)

a pharmaceutically acceptable salt thereof, or solvate of any of the foregoing, wherein:

R$^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;

R$^2$ and R$^3$ are independently selected from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring; and $R^4$ is selected from hydrogen, alkyl, substituted alkyl, aryl, substituted aryl, arylalkyl, substituted arylalkyl, aryldialkylsilyl, substituted aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, trialkylsilyl, and substituted trialkylsilyl.

In certain embodiments of a compound of Formula (I), the compound, which when administered in the intestinal lumen of a patient is absorbed to a sufficient extent so as to achieve a bioavailability of trans-4-(aminomethyl)-cyclohexanecarboxylic acid at least 2-fold greater than the bioavailability of trans-4-(aminomethyl)-cyclohexanecarboxylic acid achieved when trans-4-(aminomethyl)-cyclohexanecarboxylic acid itself is administered in the intestinal lumen of the patient.

In certain embodiments of a compound of Formula (I), $R^1$ is selected from $C_{1-6}$ alkyl, substituted $C_{1-6}$ alkyl, $C_{6-10}$ aryl, substituted $C_{6-10}$ aryl, $C_{3-7}$ cycloalkyl, substituted $C_{3-7}$ cycloalkyl, $C_{7-16}$ arylalkyl, and $C_{7-16}$ substituted arylalkyl. In certain of the immediately preceding embodiments, the substituent group of $R^1$ is selected from at least one of $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of a compound of Formula (I), $R^1$ is selected from $C_{1-4}$ alkyl, substituted $C_{1-4}$ alkyl, phenyl, substituted phenyl, cyclohexyl, and substituted cyclohexyl. In certain of the immediately preceding embodiments, each substituent group of $R^1$ is independently selected from at least one of $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino. In certain embodiments of a compound of Formula (I), each substituent group of $R^1$ is independently selected from at least one of $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino. In certain embodiments of a compound of Formula (I), $R^1$ is selected from methyl, ethyl, n-propyl, isopropyl, n-butyl, isobutyl, sec-butyl, tert-butyl, phenyl, o-tolyl, and cyclohexyl.

In certain embodiments of a compound of Formula (I), $R^4$ is selected from hydrogen, $C_{1-6}$ alkyl, substituted $C_{1-6}$ alkyl, $C_{3-7}$ cycloalkyl, substituted $C_{3-7}$ cycloalkyl, $C_{6-10}$ aryl, substituted $C_{6-10}$ aryl, $C_{7-16}$ arylalkyl, substituted $C_{7-16}$ arylalkyl, $C_{3-12}$ trialkylsilyl, and $C_{7-14}$ aryldialkylsilyl. In certain of the immediately preceding embodiments, each substituent group of $R^4$ is independently selected from at least one of $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino. In certain embodiments of a compound of Formula (I), $R^4$ is selected from hydrogen, methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl, and phenyldimethylsilyl.

In certain embodiments of a compound of Formula (I), $R^4$ is selected from hydrogen, allyl, benzyl, and trimethylsilyl.

In certain embodiments of a compound of Formula (I), $R^4$ is hydrogen.

In certain embodiments of a compound of Formula (I), $R^2$ and $R^3$ are independently selected from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl. In certain of the immediately preceding embodiments, each substituent group of $R^2$ and/or $R^3$ is independently selected from at least one of $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino. In certain embodiments of a compound of Formula (I), $R^2$ and $R^3$ are independently selected from hydrogen, methyl, ethyl, n-propyl, isopropyl, phenyl, and cyclohexyl.

In certain embodiments of a compound of Formula (I), $R^2$ is hydrogen, and $R^3$ is selected from hydrogen, methyl, ethyl, n-propyl, isopropyl, phenyl, and cyclohexyl. In certain embodiments of a compound of Formula (I), $R^2$ is hydrogen, and $R^3$ is selected from methyl, ethyl, n-propyl, isopropyl, phenyl, and cyclohexyl.

In certain embodiments of a compound of Formula (I), $R^1$ is selected from $C_{1-6}$ alkyl, substituted $C_{1-6}$ alkyl, $C_{6-10}$ aryl, substituted $C_{6-10}$ aryl, $C_{3-7}$ cycloalkyl, substituted $C_{3-7}$ cycloalkyl, $C_{7-16}$ arylalkyl, and $C_{7-16}$ substituted arylalkyl, and $R^2$ and $R^3$ are independently selected from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl. In certain of the immediately preceding embodiments, each substituent group of $R^1$ is independently selected from at least one of $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of a compound of Formula (I), $R^1$ is selected from methyl, ethyl, n-propyl, isopropyl, n-butyl, isobutyl, sec-butyl, tert-butyl, phenyl, o-tolyl, and cyclohexyl, $R^2$ is hydrogen, and $R^3$ is selected from hydrogen, methyl, ethyl, n-propyl, isopropyl, phenyl, and cyclohexyl. In certain embodiments of a compound of Formula (I), $R^1$ is selected from methyl, ethyl, n-propyl, isopropyl, n-butyl, isobutyl, sec-butyl, tert-butyl, phenyl, o-tolyl, and cyclohexyl, $R^2$ is hydrogen, and $R^3$ is selected from methyl, ethyl, n-propyl, isopropyl, phenyl, and cyclohexyl.

In certain embodiments of a compound of Formula (I), $R^4$ is hydrogen.

In certain embodiments of a compound of Formula (I), each of $R^2$ and $R^3$ is other than hydrogen. When each of $R^2$ and $R^3$ is hydrogen, a metabolite of certain acyloxyalkylcarbamate promoieties may be formaldehyde. In some embodiments for methods of treatment comprising administering large amounts of a compound of Formula (I) it may be desirable that the amount of toxic metabolites of the promoiety such as formaldehyde be minimized or eliminated.

In certain embodiments of a compound of Formula (I), the compound is selected from:

trans-4-{[(2-Methylpropanoyloxy)methoxycarbonyl]aminomethyl}-cyclohexanecarboxylic acid;

trans-4-{[(2,2-Dimethylpropanoyloxy)methoxycarbonyl]aminomethyl}-cyclohexanecarboxylic acid;

trans-4-{[(3-Methylbutanoyloxy)methoxycarbonyl]aminomethyl}-cyclohexanecarboxylic acid;

trans-4-{[(Benzoyloxy)methoxycarbonyl]aminomethyl}-cyclohexanecarboxylic acid;

trans-4-{[1-(2-Methylpropanoyloxy)ethoxycarbonyl]aminomethyl}-cyclohexanecarboxylic acid;

trans-4-{[1-(2-Methylpropanoyloxy)propoxycarbonyl]aminomethyl}-cyclohexanecarboxylic acid;

trans-4-{[1-(2-Methylpropanoyloxy)-2-methylpropoxycarbonyl]aminomethyl}-cyclohexanecarboxylic acid;

trans-4-{[1-(Benzoyloxy)-2-methylpropoxycarbonyl]aminomethyl}-cyclohexanecarboxylic acid;
trans-4-{[1-(Cyclohexylcarbonyloxy)-2-methylpropoxycarbonyl]aminomethyl}-cyclohexanecarboxylic acid;
trans-4-{[1-(Pentanoyloxy)-2-methylpropoxycarbonyl]aminomethyl}-cyclohexanecarboxylic acid;
trans-4-{[1-(Propanoyloxy)-2-methylpropoxycarbonyl]aminomethyl}-cyclohexanecarboxylic acid;
trans-4-{[1-(Butanoyloxy)ethoxycarbonyl]aminomethyl}-cyclohexanecarboxylic acid;
trans-4-{[1-(Pentanoyloxy)ethoxycarbonyl]aminomethyl}-cyclohexanecarboxylic acid;
trans-4-{[1-(3-Methylbutanoyloxy)ethoxycarbonyl]aminomethyl}-cyclohexanecarboxylic acid;
trans-4-{[1-(2,2-Dimethylpropanoyloxy)ethoxycarbonyl]aminomethyl}-cyclohexanecarboxylic acid;
trans-4-{[1-(Cyclohexylcarbonyloxy)ethoxycarbonyl]aminomethyl}-cyclohexanecarboxylic acid;
trans-4-{[1-(Benzoyloxy)ethoxycarbonyl]aminomethyl}-cyclohexanecarboxylic acid;
trans-4-{[1-(2-Methylbenzoyloxy)ethoxycarbonyl]aminomethyl}-cyclohexanecarboxylic acid;
trans-4-{[1-(Butanoyloxy)butoxycarbonyl]aminomethyl}-cyclohexanecarboxylic acid;
trans-4-{[1-(2-Methylpropanoyloxy)butoxycarbonyl]aminomethyl}-cyclohexanecarboxylic acid;
trans-4-{[1-(3-Methylbutanoyloxy)butoxycarbonyl]aminomethyl}-cyclohexanecarboxylic acid;
trans-4-{[1-(2,2-Dimethylpropanoyloxy)butoxycarbonyl]aminomethyl}-cyclohexanecarboxylic acid;
trans-4-{[1-(Benzoyloxy)butoxycarbonyl]aminomethyl}-cyclohexanecarboxylic acid;
trans-4-{[1-(Propanoyloxy)propoxycarbonyl]aminomethyl}-cyclohexanecarboxylic acid;
trans-4-{[1-(Butanoyloxy)propoxycarbonyl]aminomethyl}-cyclohexanecarboxylic acid;
trans-4-{[1-(2,2-Dimethylpropanoyloxy)propoxycarbonyl]aminomethyl}-cyclohexanecarboxylic acid;
trans-4-{[1-(Benzoyloxy)propoxycarbonyl]aminomethyl}-cyclohexanecarboxylic acid;
trans-4-{[1-(Butanoyloxy)-2-methylpropoxycarbonyl]aminomethyl}-cyclohexanecarboxylic acid;
trans-4-{[1-(Butanoyloxy)-1-cyclohexylmethoxycarbonyl]aminomethyl}-cyclohexanecarboxylic acid;
trans-4-{[1-(2-Methylpropanoyloxy)-1-cyclohexylmethoxycarbonyl]aminomethyl}-cyclohexanecarboxylic acid;
trans-4-{[1-(Acetoxy)butoxycarbonyl]aminomethyl}-cyclohexanecarboxylic acid;
trans-4-{[1-(Propanoyloxy)butoxycarbonyl]aminomethyl}-cyclohexanecarboxylic acid;
trans-4-{[1-(Acetoxy)-2-methylpropoxycarbonyl]aminomethyl}-cyclohexanecarboxylic acid;
trans-4-{[1-(3-Methylbutanoyloxy)-2-methylpropoxycarbonyl]aminomethyl}-cyclohexanecarboxylic acid;
trans-4-{[1-(2,2-Dimethylpropanoyloxy)-2-methylpropoxycarbonyl]aminomethyl}-cyclohexanecarboxylic acid;
trans-4-{[1-(Acetoxy)ethoxycarbonyl]aminomethyl}-cyclohexanecarboxylic acid; and
trans-4-{[1-(Propanoyloxy)ethoxycarbonyl]aminomethyl}-cyclohexanecarboxylic acid;

including pharmaceutically acceptable salts thereof and pharmaceutically acceptable solvates of any of the foregoing.

Certain embodiments of the present disclosure provide a compound of Formula (II):

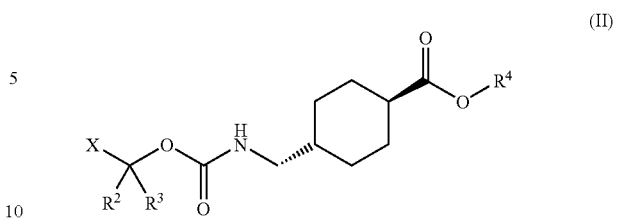

a pharmaceutically acceptable salt thereof, or solvate of any of the foregoing, wherein:

X is selected from fluoro, chloro, bromo, and $R^{20}SO_3$— wherein $R^{20}$ is selected from $C_{1-6}$ alkyl, $C_{5-7}$ aryl, and substituted $C_{5-7}$ aryl; and $R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring; and $R^4$ is selected from hydrogen, alkyl, substituted alkyl, aryl, substituted aryl, arylalkyl, substituted arylalkyl, aryldialkylsilyl, substituted aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, trialkylsilyl, and substituted trialkylsilyl.

In certain embodiments of a compound of Formula (II), at least one of $R^2$, $R^3$, and $R^4$ is substituted with a substituent group selected from at least one of $C_{1-3}$ alkyl, —OH, —NH_2, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of a compound of Formula (II), X is chloro.

In certain embodiments of a compound of Formula (II), $R^4$ is selected from hydrogen, $C_{1-6}$ alkyl, substituted $C_{1-6}$ alkyl, $C_{3-7}$ cycloalkyl, substituted $C_{3-7}$ cycloalkyl, $C_{6-10}$ aryl, substituted $C_{6-10}$ aryl, $C_{7-16}$ arylalkyl, substituted $C_{7-16}$ arylalkyl, $C_{3-12}$ trialkylsilyl, and $C_{7-14}$ aryldialkylsilyl. In certain of the immediately preceding embodiments, each substituent group of $R^4$ is independently selected from at least one of $C_{1-3}$ alkyl, —OH, —NH_2, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino. In certain embodiments of a compound of Formula (II), $R^4$ is selected from hydrogen, methyl, ethyl, tert-butyl, allyl, benzyl, 4-methoxybenzyl, diphenylmethyl, triphenylmethyl, trimethylsilyl, triethylsilyl, triisopropylsilyl, tert-butyldimethylsilyl, and phenyldimethylsilyl.

In certain embodiments of a compound of Formula (II), $R^4$ is selected from hydrogen, allyl, benzyl, and trimethylsilyl.

In certain embodiments of a compound of Formula (II), $R^4$ is hydrogen.

In certain embodiments of a compound of Formula (II), $R^2$ and $R^3$ are independently selected from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl. In certain of the immediately preceding embodiments, each substituent group of $R^2$ and/or $R^3$ is independently selected from at least one of $C_{1-3}$ alkyl, —OH, —NH_2, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino. In certain embodiments of a compound of Formula (II), $R^2$ and $R^3$ are independently selected from hydrogen, methyl, ethyl, n-propyl, isopropyl, phenyl, and cyclohexyl.

In certain embodiments of a compound of Formula (II), $R^2$ is hydrogen, and $R^3$ is selected from hydrogen, methyl, ethyl, n-propyl, isopropyl, phenyl, and cyclohexyl.

In certain embodiments of a compound of Formula (II), $R^2$ and $R^3$ are independently selected from hydrogen, $C_{1-6}$ alkyl, substituted $C_{1-6}$ alkyl, $C_{6-10}$ aryl, substituted $C_{6-10}$ aryl, $C_{3-7}$ cycloalkyl, and substituted $C_{3-7}$ cycloalkyl, and $R^4$ is selected from hydrogen, $C_{1-6}$ alkyl, substituted $C_{1-6}$ alkyl, $C_{3-7}$ cycloalkyl, substituted $C_{3-7}$ cycloalkyl, $C_{6-10}$ aryl, substituted $C_{6-10}$ aryl, $C_{7-16}$ arylalkyl, substituted $C_{7-16}$ arylalkyl, $C_{3-12}$ trialkylsilyl, and $C_{7-14}$ aryldialkylsilyl. In certain of the immediately preceding embodiments, each substituent group of $R^2$ and/or $R^3$ is independently selected from at least one of $C_{1-3}$ alkyl, —OH, —NH$_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino. In certain embodiments of a compound of Formula (II), $R^2$ is hydrogen, $R^3$ is selected from hydrogen, methyl, ethyl, n-propyl, isopropyl, phenyl, and cyclohexyl, and $R^4$ is hydrogen.

In certain embodiments of a compound of Formula (II), X is chloro, $R^2$ is hydrogen, $R^3$ is selected from hydrogen, methyl, ethyl, n-propyl, isopropyl, phenyl, and cyclohexyl, and $R^4$ is hydrogen.

Compounds of Formula (II) are useful intermediates in the synthesis of compounds of Formula (I) as described below.

Synthesis

Compounds of the present disclosure may be obtained via the synthetic methods illustrated in Schemes 1-9. Those of ordinary skill in the art will appreciate that a synthetic route to the disclosed compounds consists of attaching promoieties to tranexamic acid.

A variety of methods for synthesis of acyloxyalkyl carbamate derivatives of amines are known in the art (for example, see Alexander et al., U.S. Pat. No. 4,426,391; Alexander, U.S. Pat. No. 4,760,057; Lund, U.S. Pat. No. 5,401,868; Saari et al., European Patent No. 0416689B 1; Mulvihill et al., *Tetrahedron Lett.*, 2001, 7751-7754; Sun et al., *Bioorg. Med. Chem. Lett.*, 2001, 11, 1875-1879; Sun et al., *Bioorg. Med. Chem. Lett.*, 2001, 11, 3055-3059; Chen et al., International Publication No. WO 01/05813; Mulvihill et al., *Synthesis*, 2002, 3, 365-370; Gallop et al., U.S. Pat. No. 6,927,036; Raillard et al., U.S. Patent Application Publication No. 2004/0014940; Bhat et al., U.S. Patent Application Publication No. 2005/0070715; Gallop et al., U.S. Patent Application Publication No. 2005/0222431).

General synthetic methods useful in the synthesis of the compounds described herein are available in the art (e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996; Larock, "Comprehensive Organic Transformations," VCH Publishers, 1989; and Paquette, "Encyclopedia of Reagents for Organic Synthesis," John Wiley & Sons, 1995).

Accordingly, starting materials useful for preparing compounds and intermediates thereof, and/or for practicing methods described herein are commercially available or may be prepared by well-known synthetic methods. Other methods for synthesis of the prodrugs of the present disclosure are either described in the art or will be readily apparent to the skilled artisan in view of the references provided above and may be used to synthesize the compounds described herein. Accordingly, the methods presented in the Schemes herein are illustrative rather than comprehensive.

Intermediate (V), useful in the preparation of 1-haloalkyl carbamates of Formula (II), may be generated according to the reactions detailed in Scheme 1:

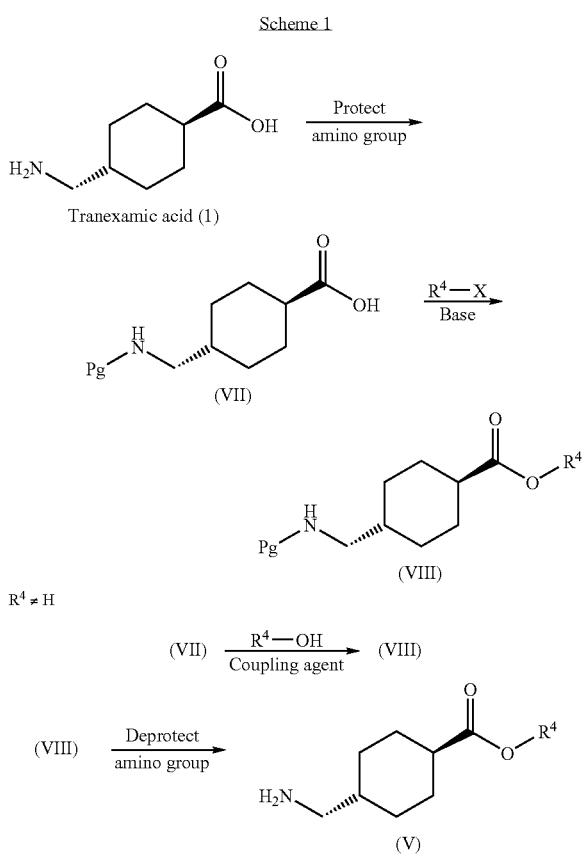

The amino group of tranexamic acid is protected under standard conditions with a protecting group (Pg) to afford compound (VII). The carboxylic acid moiety of compound (VII) is esterified to yield compound (VIII), either via alkylation or silylation with $R^4$—X, where X is selected from fluoro, chloro, bromo, iodo, and $R^{20}SO_3$— wherein $R^{20}$ is selected from $C_{1-6}$ alkyl, $C_{5-7}$ aryl, and substituted $C_{5-7}$ aryl, or any other suitable leaving group, or via condensation with alcohol $R^4$—OH under standard acylation conditions (e.g., in the presence of a coupling agent such as a carbodiimide, via an acyl halide, acid anhydride, or other activated ester intermediate). Removal of the protecting group from compound (VIII) under standard deprotection conditions affords compound (V).

In certain embodiments, a compound of Formula (II) is prepared by acylation of compound (V) with compound (IX) (see Scheme 2), where X is a halide and Z is a leaving group (e.g., halide, p-nitrophenolate, imidazolyl, etc.). In certain embodiments, X is F, Cl, Br, or I. In some of these embodiments, Z is Cl. In certain embodiments, X and Z are each Cl. The acylation reaction may be performed in the presence of an inorganic base or an organic base (e.g., tertiary amine bases, such as triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene or 1,5-diazabicyclo[4.3.0]undec-7-ene), and combinations of any of the foregoing. Suitable solvents for acylation include, but are not limited to, dichloromethane, dichloroethane, chloroform, toluene, dimethylformamide, dimethylacetamide, N-methylpyrrolidinone, dimethyl sulfoxide, pyridine, ethyl acetate, isopropyl acetate, acetonitrile, acetone, 2-butanone, methyl tert-butyl ether, and combinations of any of the foregoing. Alternatively, biphasic solvent mixtures comprising water and including one or more of dichloromethane, dichloroethane, chloroform, toluene, ethyl acetate, isopropyl acetate, or methyl tert-butyl ether, can be utilized. Temperatures for performing the reaction of Scheme 2 can range from about −20° C. to about 50° C., and in certain embodiments can range from about −20° C. to about 25° C.

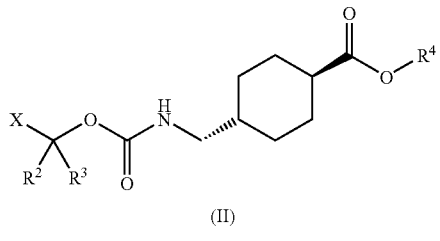

(II)

$R^4$ = trialkylsilyl, aryldialkylsilyl

In certain embodiments, N-1-acyloxylalkyl carbamates of Formula (I) can be prepared from compounds of Formula (II) by treatment with carboxylic acids of Formula (III) in the presence of an organic or inorganic base, or other metal salt, as illustrated in Scheme 4.

Scheme 2

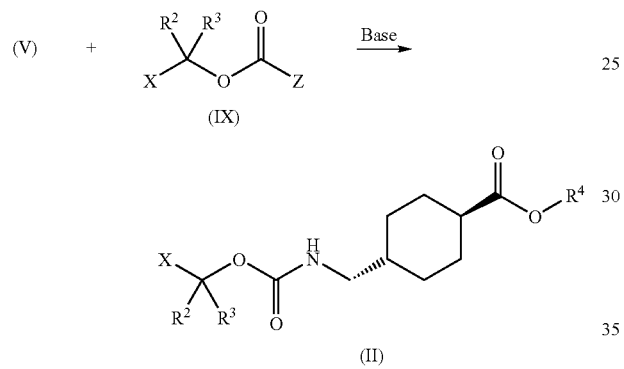

Scheme 4

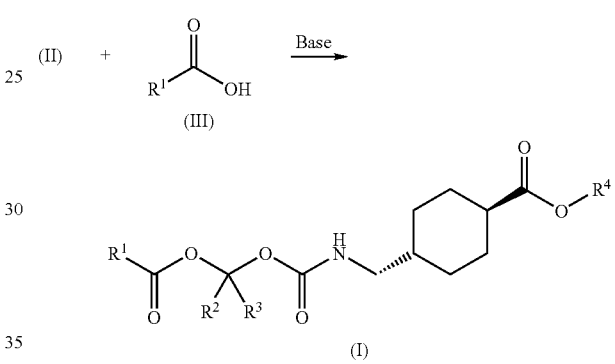

In certain embodiments, a compound of Formula (II), where $R^4$ is trialkylsilyl or aryldialkylsilyl, can be prepared directly from tranexamic acid by silylation (e.g., using a silyl halide or silylamide reagent) followed by acylation of the resulting intermediate with compound (IX) (see Scheme 3). Suitable solvents for performing this reaction include, but are not limited to, dichloromethane, dichloroethane, chloroform, toluene, pyridine, acetonitrile, and combinations of any of the foregoing. Suitable bases for performing this reaction include but are not limited to, triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1, 8-diazabicyclo[5.4.0]undec-7-ene, 1,5-diazabicyclo[4.3.0]undec-7-ene, and combinations of any of the foregoing. Temperatures for performing the reaction of Scheme 3 can range from about −78° C. to about 50° C., and in certain embodiments can range from about −20° C. to about 25° C.

Scheme 3

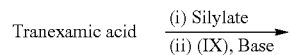

In certain embodiments of a compound of Formula (II) in the method of Scheme 4, X is selected from fluoro, chloro, bromo, and $R^2SO_3$—wherein $R^{20}$ is selected from $C_{1-6}$ alkyl, $C_{5-7}$ aryl, and substituted $C_{5-7}$ aryl. In certain embodiments of compounds of Formulae (I) and (III) in the method of Scheme 4, $R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl. In certain embodiments of compounds of Formulae (I) and (II) in the method of Scheme 4, $R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring. In certain embodiments of compounds of Formulae (I) and (II) in the method of Scheme 4, $R^4$ is selected from hydrogen, alkyl, substituted alkyl, aryl, substituted aryl, arylalkyl, substituted arylalkyl, aryldialkylsilyl, substituted aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, trialkylsilyl, and substituted trialkylsilyl. In certain of the immediately preceding embodiments, each substituent group of $R^1$, $R^2$, $R^3$, and/or $R^4$ is independently selected from at least one of $C_{1-3}$ alkyl, —OH, —NH$_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of compounds of Formulae (I), (II), and (III) in the method of Scheme 4, X is chloro, $R^1$ is selected from methyl, ethyl, n-propyl, isopropyl, n-butyl, isobutyl, sec-butyl, tert-butyl, phenyl, o-tolyl, and cyclohexyl, $R^2$ is hydrogen, $R^3$ is selected from hydrogen, methyl, ethyl, n-propyl, isopropyl, phenyl, and cyclohexyl, and $R^4$ is hydrogen.

In certain embodiments of the method of Scheme 4, the ratio of a compound of Formula (II) to a compound of Formula (III) can range from about 1:1 to about 1:20. In certain embodiments, the ratio of a compound of Formula (II) to a compound of Formula (III) can range from about 1:1 to about 1:5. In certain embodiments, the ratio of a compound of Formula (II) to a compound of Formula (III) is about 1:1.

In certain embodiments of the method of Scheme 4, compounds of Formulae (II) and (III) and a metal salt are contacted with a solvent. In certain embodiments in which a compound of Formula (I), a compound of Formula (II) and a metal salt are contacted with a solvent, the ratio of a compound of Formula (II) to a compound of Formula (III) can range from about 1:1 to about 1:20, in certain embodiments, from about 1:1 to about 1:5, and in certain embodiments, the ratio of a compound of Formula (II) to a compound of Formula (III) is about 1:1. In certain embodiments, the solvent can be dichloromethane, dichloroethane, chloroform, toluene, dimethylformamide, dimethylacetamide, N-methylpyrrolidinone, dimethyl sulfoxide, pyridine, ethyl acetate, acetonitrile, acetone, 2-butanone, methyl tert-butyl ether, methanol, ethanol, isopropanol, tert-butanol, water, hexamethylphosphoramide, and combinations of any of the foregoing. In certain embodiments, the metal salt can be a salt of Ag, Hg, Na, K, Li, Cs, Ca, Mg, Zn, and combinations of any of the foregoing.

In certain embodiments of the method of Scheme 4, compounds of Formulae (II) and (III) and an organic base are contacted with a solvent. In certain embodiments in which a compound of Formula (II), a compound of Formula (III) and an organic base are contacted with a solvent, the ratio of a compound of Formula (II) to a compound of Formula (III) can range from about 1:1 to about 1:20, in certain embodiments, from about 1:15 to about 1:20, and in certain embodiments, can range from about 1:1 to about 1:5. In certain embodiments in which a compound of Formula (II), a compound of Formula (III) and an organic base are contacted with a solvent, the ratio of a compound of Formula (II) to a compound of Formula (III) is about 1:1, and in certain embodiments, is about 1:10. In some embodiments, the solvent can be dichloromethane, dichloroethane, chloroform, toluene, dimethylformamide, dimethylacetamide, N-methylpyrrolidinone, dimethyl sulfoxide, pyridine, ethyl acetate, acetonitrile, acetone, 2-butanone, methyl tert-butyl ether, methanol, ethanol, isopropanol, tert-butanol, water, hexamethylphosphoramide, and combinations of any of the foregoing. In certain embodiments, the organic base can be triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, 1,5-diazabicyclo[4.3.0]undec-7-ene, and combinations of any of the foregoing.

In some embodiments of the method of Scheme 4, a compound of Formula (III) is a liquid under the conditions of contacting with a compound of Formula (II), and the compound of Formula (III) further serves as a solvent for the reaction with a compound of Formula (II). In certain embodiments, a compound of Formula (III) can be acetic acid, methoxyacetic acid, ethoxyacetic acid, propionic acid, butyric acid, isobutyric acid, pivalic acid, valeric acid, isovaleric acid, 2-methylbutyric acid, cyclobutanecarboxylic acid, cyclopentanecarboxylic acid, or cyclohexanecarboxylic acid.

In some embodiments of the method of Scheme 4, a compound of Formula (II), a compound of Formula (III), and a metal salt can be contacted at a temperature ranging from about −25° C. to about 120° C. In certain embodiments, the temperature can range from about 0° C. to about 25° C.

In certain other embodiments of the method of Scheme 4, a compound of Formula (II), a compound of Formula (III), and an organic base can be contacted at a temperature ranging from about −25° C. to about 120° C. In certain embodiments, the temperature can range from about 0° C. to about 25° C.

In some embodiments of the method of Scheme 4, a compound of Formula (II), a compound of Formula (III), and an organic base can be contacted with a catalytic amount of an iodide salt. In certain embodiments, the iodide salt can be sodium iodide, potassium iodide, tetramethylammonium iodide, tetraethylammonium iodide, or tetrabutylammonium iodide.

In some embodiments of the method of Scheme 4, $R^4$ can be a carboxylic acid protecting group that can be removed under mild conditions to provide a compound of Formula (I) where $R^4$ is hydrogen. Carboxylic acid protecting groups removable via mild acidic hydrolysis, fluoride ion-promoted hydrolysis, catalytic hydrogenolysis, transfer hydrogenolysis, or other transition metal-mediated deprotection reactions can be used. In some embodiments, $R^4$ can be trimethylsilyl, allyl, or benzyl.

In certain embodiments, a compound of Formula (I) can be prepared as illustrated in Scheme 5.

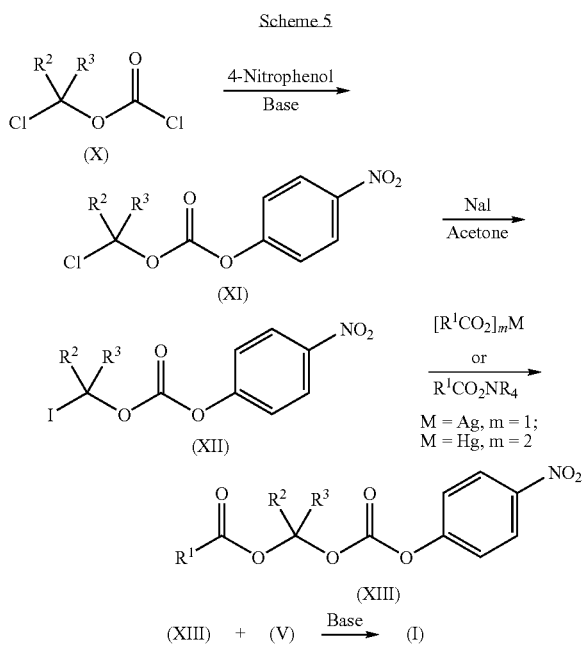

Chloroformate (X) is treated with an aromatic leaving group such as p-nitrophenol in the presence of base to provide p-nitrophenylcarbonate (XI). Halide interchange provides iodide (XII), which is reacted with a metal or tetraalkylammonium salt of a carboxylic acid to afford compound (XIII). Treatment of (XIII) with tranexamic acid derivative (V), optionally in the presence of trimethylsilyl chloride, affords a compound of Formula (I). Methods for making related acyloxyalkyl carbamate compounds are described in the art (e.g., Alexander, U.S. Pat. No. 4,760,057; Alexander, U.S. Pat. No. 4,916,230; Alexander, U.S. Pat. No. 5,466,811; Alexander, U.S. Pat. No. 5,684,018).

Another method for synthesis of compounds of Formula (I) proceeds via carbonylation of tranexamic acid derivative (V) to an intermediate carbamic acid species, which is captured by an in situ alkylation reaction in an adaptation of methods disclosed in the art (Butcher, Synlett, 1994, 825-6; Ferres et al., U.S. Pat. No. 4,036,829). Carbon dioxide gas is bubbled into a solution containing tranexamic acid derivative (V) and a base (e.g., $Cs_2CO_3$, $Ag_2CO_3$, or AgO) in a solvent such as DMF or NMP. An activated halide is added, optionally, in the presence of iodide ion as a catalyst, and the carbonylation continued until the reaction is completed. This method is illustrated in Scheme 6 for the preparation of a compound of Formula (I) from halide (XIV).

Scheme 6

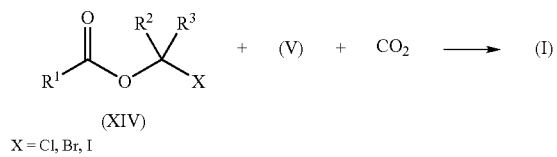

X = Cl, Br, I

Yet another method for synthesis of a compound of Formula (I) relies upon oxidation of ketocarbamate derivatives of tranexamic acid (e.g., Gallop et al., U.S. Pat. No. 6,927,036; and Bhat et al., U.S. Application Publication No. 2005/0070715). As illustrated in Scheme 7, oxidation of ketocarbamate (XV) affords a compound of Formula (I). Methods for synthesis of a compound of Formula (XV) are disclosed in U.S. Pat. No. 6,927,036 and U.S. Application Publication No. 2005/0070715. Examples of oxidants useful in the method of Scheme 6 include those successfully used in Baeyer-Villager oxidations of ketones to esters or lactones (Strukul, *Angew. Chem. Int. Ed.*, 1998, 37, 1198; Renz., *Eur. J. Org. Chem.*, 1999, 4, 737-50; Beller et al., in "Transition Metals in Organic Synthesis" Chapter 2, Wiley VCH; Stewart, *Current Organic Chemistry*, 1998, 2, 195; Kayser et al., *Synlett*, 1999, 153). The use of anhydrous oxidants can be beneficial since prodrugs of Formula (I) may be labile. Thus, performing the oxidation under anhydrous reaction conditions can avoid hydrolysis of the reactive products.

Scheme 7

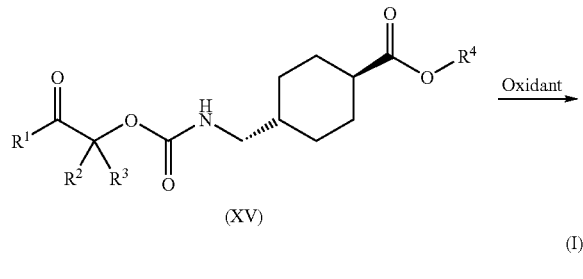

In certain embodiments of compounds of Formulae (I) and (XV) in the method of Scheme 7, $R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl. In certain embodiments of compounds of Formulae (I) and (XV), $R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl, or $R^2$ and $R^3$ together with the atom to which they are bonded form a cycloalkyl, substituted cycloalkyl, cycloheteroalkyl or substituted cycloheteroalkyl ring. In certain embodiments of compounds of Formulae (I) and (XV), $R^4$ is selected from hydrogen, alkyl, substituted alkyl, aryl, substituted aryl, arylalkyl, substituted arylalkyl, aryldialkylsilyl, substituted aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, trialkylsilyl, and substituted trialkylsilyl. In certain embodiments of compounds of Formulae (I) and (XV), each substituent group of $R^1$, $R^2$, $R^3$, and/or $R^4$ is independently selected from at least one of $C_{1-3}$ alkyl, —OH, —$NH_2$, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of compounds of Formulae (I) and (XV) in the method of Scheme 7, $R^1$ is selected from methyl, ethyl, n-propyl, isopropyl, n-butyl, isobutyl, sec-butyl, tert-butyl, phenyl, o-tolyl, and cyclohexyl, $R^2$ is hydrogen, $R^3$ is selected from hydrogen, methyl, ethyl, n-propyl, isopropyl, phenyl, and cyclohexyl, and $R^4$ is hydrogen.

In the method of Scheme 7 oxidation can be performed in the liquid phase, and in certain embodiments, in the presence of a solvent. Choosing a solvent for oxidation of a compound of Formula (XV) is well within the ambit of one of skill in the art. Generally, a useful solvent will dissolve, at least partially, both the oxidant and a compound of Formula (XV) and will be inert to the reaction conditions. Useful solvents can be anhydrous and include, but are not limited to, dichloromethane, dichloroethane, chloroform, ethyl acetate, isopropyl acetate, toluene, chlorobenzene, xylene, acetonitrile, diethyl ether, methyl tert-butyl ether, acetic acid, cyclohexane, and hexanes. Combinations of the above solvents can also be used in the oxidation of a compound of Formula (XV) to a compound of Formula (I).

In some embodiments, the anhydrous oxidant is an anhydrous peroxyacid generated in situ by reaction of a urea-hydrogen peroxide complex (UHP) with a carboxylic acid anhydride. In certain embodiments, the anhydrous oxidant is an anhydrous peroxysulfonic acid generated in situ by reaction of a urea-hydrogen peroxide complex with a sulfonic acid anhydride. The UHP complex serves as a source of anhydrous hydrogen peroxide and has been used in a variety of oxidative transformations in anhydrous organic solvents (Cooper et al., *Synlett.*, 1990, 533-535; Balicki et al., *Synth. Commun.*, 1993, 23, 3149; Astudillo et al., *Heterocycles*, 1993, 36, 1075-1080; Varmaet et al., *Org. Lett.*, 1999, 1, 189-191). However, other suitable sources of anhydrous hydrogen peroxide can also be used in the reaction instead of the UHP-complex (e.g., the 1,4-diazabicyclo[2.2.2]octane-hydrogen peroxide complex).

A useful oxidant is anhydrous peroxytrifluoroacetic acid, generated in situ by reacting the UHP-complex with trifluoroacetic anhydride (Cooper et al., Synlett., 1990, 533-535; Benjamin, et al., *J. Am. Chem. Soc.*, 2002, 124, 827-833). Anhydrous peroxycarboxylic acids (XVII) can be prepared by treating carboxylic acid anhydrides (XVI) with anhydrous hydrogen peroxide, and in certain embodiments, with the UHP-complex. Similarly, anhydrous peroxysulfonic acids (XIX) can be prepared by reacting sulfonic acid anhydrides (XVIII) with anhydrous hydrogen peroxide, and in certain embodiments, with the UHP-complex. Preparation of anhydrous peroxycarboxylic acids (XVII) and peroxysulfonic acids (XIX) is illustrated in Scheme 8.

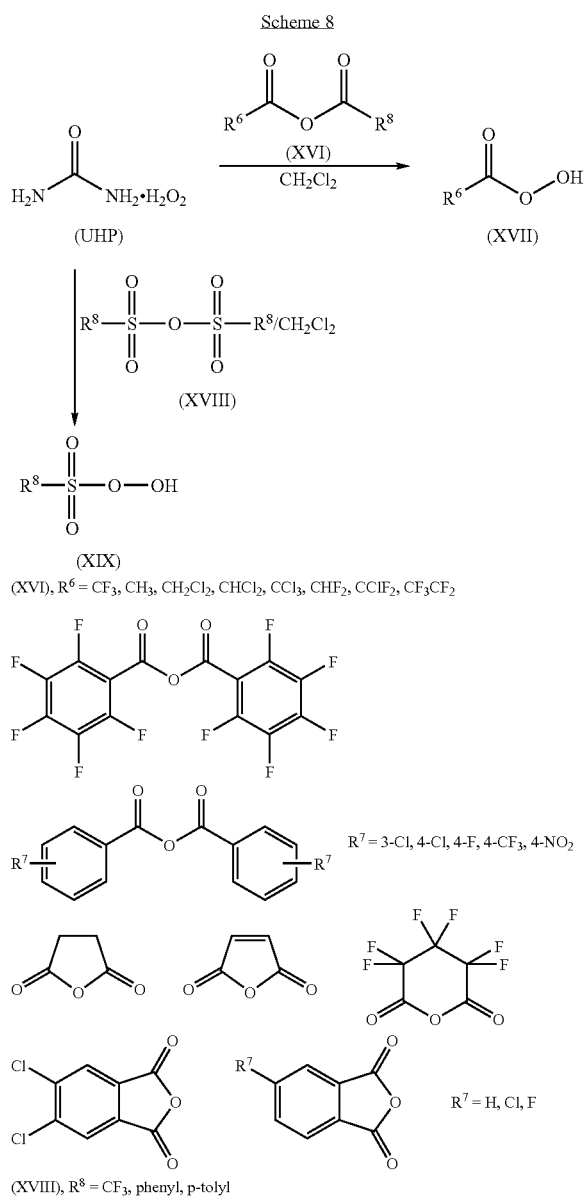

The UHP-complex and a carboxylic acid anhydride (XVI) or a sulfonic acid anhydride (XVIII) can be reacted in dichloromethane or other suitable solvent at temperatures ranging from about −25° C. to about 100° C. to generate the corresponding anhydrous peroxyacid oxidant. The peroxyacid oxidant can be generated first and subsequently reacted with a ketocarbamate (XV). In some embodiments, a carboxylic acid anhydride (XVI) is added to a stirred suspension or solution containing the UHP-complex and a ketocarbamate (XV) to generate the peroxycarboxylic acid, which reacts in situ with the ketocarbamate (XV) to give compound (I). In certain embodiments, the molar ratio of UHP-complex and carboxylic acid anhydride (XVI) is about 6:1. In certain embodiments, the molar ratio of UHP-complex and carboxylic acid anhydride (XVI) can range from about 5:1 to about 1:1. In certain embodiments, the molar ratio of UHP-complex and acid anhydride (XVI) can range from about 2:1 to about 1:1.

In some embodiments of the method of Scheme 8, the molar ratio of the peroxyacid oxidant to a compound of Formula (XV) can range from about 8:1 to about 1:1. In certain embodiments, the molar ratio of the peroxyacid oxidant to a compound of Formula (XV) can range from about 4:1 to about 1:1. In certain embodiments, the molar ratio of the peroxyacid oxidant to a compound of Formula (XV) can range from about 2:1 to about 1:1. In certain embodiments, when the oxidant is peroxytrifluoroacetic acid or another substituted peroxyacetic acid, the molar ratio of the peroxyacid oxidant to a compound of Formula (XV) is about 2:1.

Further, in the method of Scheme 8 the use of additives in the oxidation of a compound of Formula (XV) to a compound of Formula (I) is also contemplated. For example, additives can either catalyze the reaction or stabilize the final product or both. In some embodiments, a Lewis acid or a protic acid or any combination of Lewis acid or protic acid can be used in the oxidation of a compound of Formula (XV) and in certain embodiments, in the presence of a solvent. Examples of Lewis acids include, but are not limited to, $BF_3$, $SeO_2$, $MeReO_3$, $MnO_2$, $SnCl_4$, $Sc(OTf)_3$, $Ti(O-iPr)_4$, $Al_2O_3$, and $Fe_2O_3$. Examples of protic acids include, but are not limited to, trifluoroacetic acid, acetic acid, p-toluenesulfonic acid, methanesulfonic acid, trifluoromethanesulfonic acid, hydrochloric acid, and sulfuric acid. In certain embodiments, the Lewis acid and/or protic acid can catalyze oxidation by increasing the electrophilicity of the carbonyl group in Formula (XV).

In certain embodiments of the method of Scheme 8, the oxidation can be conducted in the presence of an anhydrous base. In certain embodiments, the base can stabilize acid sensitive products by reacting with acidic by-products formed during oxidation.

Generally, in the method of Scheme 8 the temperature of the reaction can be optimized by methods known to those of ordinary skill in the art. In certain embodiments, the oxidation of a compound of Formula (XV) can be carried out at a temperature ranging from about −25° C. to about 100° C., and in certain embodiments, from about 0° C. to about 25° C.

A feature of this method of synthesis of a compound of Formula (I) is that oxidation of a ketocarbamate derivative (XV) proceeds stereospecifically, with retention of configuration at the carbon atom initially adjacent to the carbonyl group in the ketocarbamate derivative (XV). This stereospecificity can be exploited in a stereoselective synthesis of prodrug derivatives of Formula (I).

Another method for synthesis of a compound of Formula (I), illustrated in Scheme 9, relies upon reaction of tranexamic acid, or a compound of Formula (V), with a 1-(acyloxy)-alkyl N-hydroxysuccinimidyl carbonate compound of Formula (IV), as described in the co-pending application Gallop et al., U.S. Application Publication No. 2005/0222431:

Scheme 9

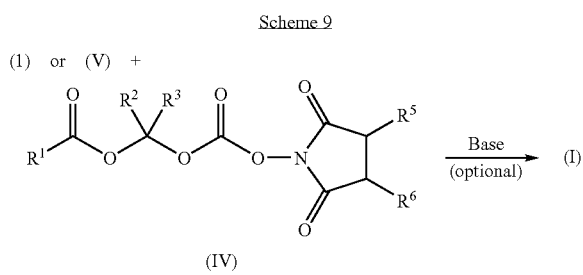

wherein $R^1$, $R^2$, $R^3$ and $R^4$ are as defined herein, and $R^5$ and $R^6$ are independently selected from hydrogen, acylamino, acyloxy, alkoxycarbonylamino, alkoxycarbonyloxy, alkyl, substituted alkyl, alkoxy, substituted alkoxy, aryl, substituted aryl, arylalkyl, substituted arylalkyl, carbamoyloxy, dialkylamino, heteroaryl, substituted heteroaryl, hydroxy, and sulfonamido, or $R^5$ and $R^6$ together with the atoms to which they are bonded form a substituted cycloalkyl, substituted cycloheteroalkyl, or substituted aryl ring. In certain of the immediately preceding embodiments, the substituent group of $R^1$, $R^2$, $R^3$, $R^4$, $R^5$, and/or $R^6$ is selected from at least one of $C_{1-3}$ alkyl, —OH, —$NH_2$, —SH, $C_{1-3}$ alkoxy, $C_{1-3}$ acyl, $C_{1-3}$ thioalkyl, $C_{1-3}$ alkoxycarbonyl, $C_{1-3}$ alkylamino, and $C_{1-3}$ dialkylamino.

In certain embodiments of compounds of Formula (I), (IV), and (V) of the method of Scheme 9, $R^1$ is selected from methyl, ethyl, n-propyl, isopropyl, n-butyl, isobutyl, sec-butyl, tert-butyl, phenyl, o-tolyl, and cyclohexyl, $R^2$ is hydrogen, $R^3$ is selected from hydrogen, methyl, ethyl, n-propyl, isopropyl, phenyl, and cyclohexyl, $R^4$ is hydrogen, and $R^5$ and $R^6$ are each hydrogen.

In some embodiments, the method of Scheme 9 can be carried out in a solvent. Useful solvents include, but are not limited to, acetone, acetonitrile, dichloromethane, dichloroethane, chloroform, toluene, tetrahydrofuran, dioxane, dimethylformamide, dimethylacetamide, N-methylpyrrolidinone, dimethyl sulfoxide, pyridine, ethyl acetate, methyl tert-butyl ether, methanol, ethanol, isopropanol, tert-butanol, water, and combinations of any of the foregoing. In certain embodiments, the solvent can be acetone, acetonitrile, dichloromethane, toluene, tetrahydrofuran, pyridine, methyl tert-butyl ether, methanol, ethanol, isopropanol, water, and combinations of any of the foregoing. In certain embodiments, the solvent can be a combination of acetonitrile and water. In certain embodiments, the solvent can be a combination of acetonitrile and water, with a volume ratio of acetonitrile to water ranging from about 1:5 to about 5:1. In certain embodiments, the solvent can be a combination of methyl tert-butyl ether and water. In certain embodiments, the solvent can be a combination of methyl tert-butyl ether and water, with a volume ratio of methyl tert-butyl ether to water ranging from about 2:1 to about 20:1. In certain embodiments, the solvent can be a combination of methyl tert-butyl ether and water, wherein the methyl tert-butyl ether contains from about 10% to about 50% acetone by volume. In certain embodiments, the solvent can be dichloromethane, water, or a combination thereof. In certain embodiments, the solvent is a biphasic combination of dichloromethane and water. In certain embodiments, the solvent can be a biphasic combination of dichloromethane and water containing from about 0.001 equivalents to about 0.1 equivalents of a phase transfer catalyst. In certain embodiments, the phase transfer catalyst is a tetraalkylammonium salt, and in certain embodiments, the phase transfer catalyst is a tetrabutylammonium salt.

The method of Scheme 9 can be carried out a temperature ranging from about −20° C. to about 40° C. In certain embodiments, the temperature can range from about −20° C. to about 25° C. In certain embodiments, the temperature can range from about 0° C. to about 25° C. In certain embodiments, the temperature can range from about 25° C. to about 40° C.

In certain embodiments of the method of Scheme 9, the reaction can be performed in the absence of a base.

In certain embodiments of the method of Scheme 9, the reaction can be performed in the presence of an inorganic base. In some embodiments, the reaction can be performed in the presence of an alkali metal bicarbonate or alkali metal carbonate salt. In certain embodiments, the reaction can be performed in the presence of sodium bicarbonate.

In certain embodiments of the method of Scheme 9, the reaction can be performed in the presence of an organic base. In certain embodiments, the reaction can be performed in the presence of triethylamine, tributylamine, diisopropylethylamine, dimethylisopropylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, 1,5-diazabicyclo[4.3.0]undec-7-ene, or a combination of any of the foregoing. In certain embodiments, the reaction can be performed in the presence of triethylamine, diisopropylethylamine, N-methylmorpholine, or pyridine.

Pharmaceutical Compositions

Pharmaceutical compositions comprising a therapeutically effective amount of one or more tranexamic acid prodrug compounds of Formula (I), optionally in purified form, together with a suitable amount of a pharmaceutically acceptable vehicle, so as to provide a form for proper administration to a patient are provided herein. Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Compositions of the present disclosure, if desired, can also contain minor amounts of wetting agents, emulsifying agents, or pH buffering agents. In addition, auxiliary, stabilizing, thickening, lubricating, and coloring agents can be included.

Pharmaceutical compositions can be manufactured, for example, by means of conventional mixing, dissolving, granulating, dragee-making, levigating, emulsifying, encapsulating, entrapping, and lyophilizing processes. Pharmaceutical compositions can be formulated in a conventional manner using one or more physiologically acceptable carriers, diluents, excipients, and auxiliaries, which facilitate processing of compounds disclosed herein into preparations, which can be used pharmaceutically. Proper formulation can be dependent upon the route of administration chosen.

The present pharmaceutical compositions can take the form of, for example, solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, a pharmaceutically acceptable vehicle can be a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). In some embodiments, compositions can be formulated for oral delivery, for example, oral sustained release administration. In certain embodiments, compositions can be formulated for topical delivery, and in certain embodiments, for topical sustained release administration.

Pharmaceutical compositions for oral delivery can be in the form of, for example, tablets, lozenges, aqueous or oily suspensions, granules, powders, emulsions, capsules, syrups, or elixirs, for example. Orally administered compositions can contain one or more optional agents, sweetening agents such as fructose, aspartame or saccharin, flavoring agents such as peppermint, oil of wintergreen, cherry coloring agents, and preserving agents, to provide a palatable preparation. Moreover, when in tablet or pill form, the compositions can be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, etc. Such vehicles may be of pharmaceutical grade.

For oral liquid preparations for example, suspensions, elixirs and solutions, suitable carriers, excipients or diluents include water, saline, alkyleneglycols (e.g., propylene glycol), polyalkylene glycols (e.g., polyethylene glycol), oils, alcohols, slightly acidic buffers between about pH 4 and about pH 6 (e.g., acetate, citrate, ascorbate at between about 5 mM to about 50 mM), etc. Additionally, flavoring agents, preservatives, coloring agents, bile salts, acylcamitines, and the like can be added.

For topical formulations of tranexamic acid prodrug compounds of Formula (I) in the form of creams, gels, viscous lotions, transdermal patches, and/or sprays can be used as appropriate delivery forms. Such formulations can comprise one or more tranexamic acid prodrug compounds of Formula (I), optionally in purified form, together with a suitable amount of any pharmaceutically acceptable topical excipients including, but not limited to, gels, patches, lotions, creams, ointments, and liquids.

Compositions for topical administration include those for delivery via the mouth (buccal), nose (nasal), the rectum (rectal), the vagina (vaginal), and through the skin (dermal). Topical delivery systems also include transdermal patches containing at least one compound of Formula (I) to be administered. Delivery through the skin can be achieved by diffusion or by more active energy sources such as iontophoresis or electrotransport.

Compositions suitable for topical administration in the mouth include lozenges comprising a compound of Formula (I) optionally in a flavored basis such as sucrose and acacia or tragacanth, pastilles comprising a compound of Formula (I) in an inert basis such as gelatin and glycerin, or sucrose and acacia; and mouthwashes comprising a compound of Formula (I) administered in a suitable liquid vehicle.

Compositions suitable for topical administration to the skin include ointments, creams, gels, patches, pastes and sprays comprising a compound of Formula (I) to be administered in a pharmaceutical acceptable vehicle. Formulations of a compound of Formula (I) for topical use, such as in creams, ointments and gels, can include an oleaginous or water-soluble ointment base. For example, topical compositions can include vegetable oils, animal fats, and in certain embodiments, semisolid hydrocarbons obtained from petroleum. Topical compositions can further include white ointment, yellow ointment, cetyl esters wax, oleic acid, olive oil, paraffin, petrolatum, white petrolatum, spermaceti, starch glycerite, white wax, yellow wax, lanolin, anhydrous lanolin, and glyceryl monostearate. Various water-soluble ointment bases can also be used, including glycol ethers and derivatives, polyethylene glycols, polyoxyl 40 stearate, and polysorbates.

Compositions for rectal administration can be in the form of a suppository with a suitable base comprising, for example, cocoa butter or a salicylate. Compositions suitable for vaginal administration can be provided as pessaries, tampons, creams, gels, pastes, foams, or spray formulations containing in addition to a compound of Formula (I) such vehicles as are known in the art to be appropriate. Compositions for nasal administration can be in the form of, for example, nasal solutions, sprays, aerosols, or inhalants, and can include in addition to at least one compound of Formula (I), vehicles suitable for nasal administration.

When a compound of Formula (I), is acidic, it can be included in any of the above-described formulations as the free acid, a pharmaceutically acceptable salt, a solvate, or a hydrate. Pharmaceutically acceptable salts can substantially retain the activity of the free acid, can be prepared by reaction with bases, and can be more soluble in aqueous and other protic solvents than the corresponding free acid form. In some embodiments, sodium salts of a compound of Formula (I) can be used in the above described formulations.

Sustained Release Oral Dosage Forms

The disclosed compounds may be used with a number of different dosage forms, which can be adapted to provide sustained release of a compound of Formula (I) upon oral administration.

In some embodiments, a dosage form can comprise beads that on dissolution or diffusion release a compound disclosed herein over an extended period of hours, in certain embodiments, over a period of at least 4 hours, in certain embodiments, over a period of at least 8 hours and in certain embodiments, over a period of at least 12 hours. The beads can have a central composition or core comprising a compound disclosed herein and pharmaceutically acceptable vehicles, including an optional lubricant, antioxidant, and buffer. The beads can be medical preparations with a diameter ranging from about 0.05 mm to about 2 mm. Individual beads can comprise doses of a compound disclosed herein, for example, doses of up to about 40 mg of the compound. The beads, in some embodiments, can be formed of non-cross-linked materials to enhance their discharge from the gastrointestinal tract. The beads can be coated with a release rate-controlling polymer that gives a timed-release profile.

The time-release beads can be manufactured into a tablet for therapeutically effective administration. The beads can be made into matrix tablets by the direct compression of a plurality of beads coated with, for example, an acrylic resin and blended with excipients such as hydroxypropylmethyl cellulose. The manufacture of beads has been disclosed in the art (Lu, *Int. J. Pharm.*, 1994, 112, 117-124; "Pharmaceutical Sciences" by Remington, 14th Ed, pp. 1626-1628 (1970); Fincher, *J. Pharm. Sci.*, 1968, 57, 1825-1835; and U.S. Pat. No. 4,083,949) as has the manufacture of tablets ("Pharmaceutical Sciences," by Remington, 17th Ed, Ch. 90, pp 1603-1625 (1985)).

One type of sustained release oral dosage formulation that can be used with the disclosed compounds comprises an inert core, such as a sugar sphere, coated with an inner drug-containing layer and an outer membrane layer controlling drug release from the inner layer. A "sealcoat" can be provided between the inert core and the layer containing the active ingredient. When the core is of a water-soluble or water-swellable inert material, the sealcoat can be in the form of a relatively thick layer of a water-insoluble polymer. Such a controlled release bead an thus comprise: (i) a core unit of a substantially water-soluble or water-swellable inert material; (ii) a first layer on the core unit of a substantially water-insoluble polymer; (iii) a second layer covering the first layer and containing an active ingredient; and (iv) a third layer on the second layer of polymer effective for controlled release of the active ingredient, wherein the first layer is adapted to control water penetration into the core.

In certain embodiments, the first layer (ii) above can constitute more than about 2% (w/w) of the final bead composition, and in certain embodiments, more than about 3% (w/w), e.g., from about 3% to about 80% (w/w). The amount of the second layer (ii) above can constitute from about 0.05% to about 60% (w/w), and in certain embodiments from about 0.1% to about 30% (w/w) of the final bead composition. The amount of the third layer (iv) above can constitute from about 1% to about 50% (w/w), in certain embodiments, from about 2% to about 25% (w/w) of the final bead composition. The core unit can have a size ranging from about 0.05 to about 2 mm. The controlled release beads can be provided in a multiple unit formulation, such as a capsule or a tablet.

The cores can comprise a water-soluble or swellable material and can be any such material that is conventionally used as cores or any other pharmaceutically acceptable water-soluble or water-swellable material made into beads or pellets. The cores can be spheres of materials such as sucrose/starch (Sugar Spheres NF), sucrose crystals, or extruded and dried spheres typically comprised of excipients such as microcrystalline cellulose and lactose. The substantially water-insoluble material in the first, or sealcoat layer can be a "GI insoluble" or "GI partially insoluble" film forming polymer (dispersed or dissolved in a solvent). Examples include, but are not limited to, ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. In certain embodiments, a plasticizer can be used together with the polymer. Examples of plasticizers include, but are not limited to, dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, and fractionated coconut oil (medium-chain triglycerides). The second layer containing the active ingredient can comprise an active ingredient with or without a polymer as a binder. The binder, when used, can be hydrophilic, and in certain embodiments can be water-soluble or water-insoluble. Examples of polymers that can be used in the second layer containing the active drug include hydrophilic polymers such as, polyvinylpyrrolidone (PVP), polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethylhydroxyethyl cellulose, acrylic acid polymers, polymethacrylates, or any other pharmaceutically acceptable polymer. The ratio of drug to hydrophilic polymer in the second layer can range from about 1:100 to about 100:1 (w/w). Suitable polymers for use in the third layer, or membrane, for controlling the drug release can be selected from water-insoluble polymers or polymers with pH-dependent solubility, such as, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above. Optionally, the controlled release layer comprises, in addition to the polymers above, other substance(s) with different solubility characteristics, to adjust the permeability and thereby the release rate, of the controlled release layer. Example of polymers that can be used as a modifier together with, for example, ethyl cellulose include, but are not limited to, HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer, methacrylic acid copolymer, and combinations of any of the foregoing. Additives such as sucrose, lactose and pharmaceutical grade surfactants can also be included in the controlled release layer, if desired.

The preparation of the multiple unit formulation can comprise the additional step of transforming the prepared beads into a pharmaceutical formulation, such as by filling a predetermined amount of the beads into a capsule, or compressing the beads into tablets. Examples of multi-particulate sustained release oral dosage forms are described in, for example, U.S. Pat. Nos. 6,627,223 and 5,229,135.

In certain embodiments, polymeric materials can be used (See "Medical Applications of Controlled Release," Langer and Wise (eds.), CRC Press, Boca Raton, Fla. (1974); "Controlled Drug Bioavailability, Drug Product Design and Performance," Smolen and Ball (eds.), Wiley, New York (1984); Langer et al., *J Macromol. Sci. Rev. Macromol Chem.*, 1983, 23, 61; see also Levy et al., *Science*, 1985, 228, 190; During et al., *Ann. Neurol.*, 1989, 25, 351; Howard et al., *J. Neurosurg.*, 1989, 71, 105). In some embodiments, polymeric materials can be used for oral sustained release delivery. Polymers include, but are not limited to, sodium carboxymethylcellulose, hydroxypropylcellulose, hydroxypropylmethylcellulose, and hydroxyethylcellulose (especially, hydroxypropylmethylcellulose). Other cellulose ethers have been described (Alderman, *Int. J. Pharm. Tech. & Prod. Mfr.*, 1984, 5(3), 1-9). Factors affecting drug release are well known to the skilled artisan and have been described in the art (Bamba et al., *Int. J. Pharm.*, 1979, 2, 307).

In certain embodiments, enteric-coated preparations can be used for oral sustained release administration. Examples of useful coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release), and polymers that form firm layers that are destroyed by an increase in pressure (i.e., pressure-controlled release).

In certain embodiments, drug-releasing lipid matrices can be used for oral sustained release administration. An example is when solid microparticles of a compound disclosed herein are coated with a thin controlled release layer of a lipid (e.g., glyceryl behenate and/or glyceryl palmitostearate) as disclosed in Farah et al., U.S. Pat. No. 6,375,987 and Joachim et al., U.S. Pat. No. 6,379,700. The lipid-coated particles can optionally be compressed to form a tablet. Another controlled release lipid-based matrix material that is suitable for sustained release oral administration comprises polyglycolized glycerides as disclosed in Roussin et al., U.S. Pat. No. 6,171,615.

In certain embodiments, waxes can be used for oral sustained release administration. Examples of suitable sustained compound-releasing waxes are disclosed in Cain et al., U.S. Pat. No. 3,402,240 (carnauba wax, candelilla wax, esparto wax and ouricury wax); Shtohryn et al., U.S. Pat. No. 4,820,523 (hydrogenated vegetable oil, bees wax, carnauba wax, paraffin, candelilla, ozokerite and combinations of any of the foregoing); and Walters, U.S. Pat. No. 4,421,736 (mixture of paraffin and castor wax).

In certain embodiments, osmotic delivery systems can be used for oral sustained release administration (Verma et al., *Drug Dev. Ind. Pharm.*, 2000, 26, 695-708). In some embodiments, OROS® systems made by Alza Corporation, Mountain View, Calif. can be used for oral sustained release delivery devices (Theeuwes et al., U.S. Pat. No. 3,845,770; Theeuwes et al., U.S. Pat. No. 3,916,899).

In certain embodiments, a controlled-release system can be placed in proximity of the target of a compound disclosed herein (e.g., within the spinal cord), thus requiring only a fraction of the systemic dose (See, e.g., Goodson, in "Medical Applications of Controlled Release," supra, vol. 2, pp. 115-138 (1984)). Other controlled-release systems discussed in Langer, *Science*, 1990, 249, 1527-1533 can also be used.

In certain embodiments, a dosage form can comprise a compound disclosed herein coated on a polymer substrate. The polymer can be an erodible, or a nonerodible polymer. The coated substrate can be folded onto itself to provide a bilayer polymer drug dosage form. For example, a compound disclosed herein can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, a bioerodible dosage form erodes at a controlled rate to dispense a compound disclosed herein over a sustained release period. Representative biodegradable polymers include biodegradable poly(amides), poly (amino acids), poly(esters), poly(lactic acid), poly(glycolic acid), poly(carbohydrate), poly(orthoester), poly(orthocarbonate), poly(acetyl), poly(anhydrides), biodegradable poly(dihydropyrans), and poly(dioxinones) which are known in the art (Rosoff, *Controlled Release of Drugs Chap.* 2, pp. 53-95 (1989); and in U.S. Pat. Nos. 3,811,444; 3,962,414; 4,066,747, 4,070,347; 4,079,038; and 4,093,709).

In certain embodiments, a dosage form can comprise a compound of Formula (I) loaded into a polymer that releases the compound by diffusion through a polymer, or by flux through pores or by rupture of a polymer matrix. The drug delivery polymeric dosage form can comprise from about 10 mg to about 500 mg of the compound homogenously contained in or on a polymer. The dosage form can comprise at least one exposed surface at the beginning of dose delivery. The non-exposed surface, when present, can be coated with a pharmaceutically acceptable material impermeable to the passage of the compound. The dosage form can be manufactured by procedures known in the art. An example of providing a dosage form comprises blending a pharmaceutically acceptable carrier such as polyethylene glycol, with a known dose of a compound at an elevated temperature, (e.g., 37° C.), and adding the blended composition to a silastic medical grade elastomer with a cross-linking agent, for example, octanoate, followed by casting in a mold. The step can be repeated for each optional successive layer. The system can be allowed to set for about 1 hour, to provide the dosage form. Representative polymers for manufacturing the dosage include olefinic polymers, vinyl polymers, addition polymers, condensation polymers, carbohydrate polymer and silicone polymers as represented by polyethylene, polypropylene, polyvinyl acetate, polymethylacrylate, polyisobutylmethacrylate, poly alginate, polyamide and polysilicone. The polymers and procedures for manufacturing the polymers have been described in the art (Coleman et al., *Polymers*, 1990, 31, 1187-1231; Roerdink et al., *Drug Carrier Systems*, 1989, 9, 57-10; Leong et al., *Adv. Drug Delivery Rev.*, 1987, 1, 199-233; Roff et al., *Handbook of Common Polymers*, 1971, CRC Press; and U.S. Pat. No. 3,992,518).

In certain embodiments, a dosage form can comprise a plurality of pills. The time-release pills can provide a number of individual doses for providing various time doses for achieving a sustained-release prodrug delivery profile over an extended period of time up to about 24 hours. The matrix can comprise a hydrophilic polymer such as, a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, or a hydrophilic colloid. The hydrophilic matrix can comprise a plurality of 4 to 50 time release pills, each time release pill comprising a dose population of from about 10 ng, about 0.5 mg, 1 mg, about 1.2 mg, about 1.4 mg, about 1.6 mg, about 5.0 mg, etc. The pills can comprise a release rate-controlling wall ranging from about 0.001 mm to about 10 mm thick to provide for the timed release of a compound of Formula (I). Representative wall forming materials include a triglyceryl ester such as glyceryl tristearate, glyceryl monostearate, glyceryl dipalmitate, glyceryl laureate, glyceryl didecenoate and glyceryl tridenoate. Other wall forming materials include polyvinyl acetate, phthalate, methylcellulose phthalate, and microporous olefins. Procedures for manufacturing pills are disclosed in U.S. Pat. Nos. 4,434,153; 4,721,613; 4,853,229; 2,996,431; 3,139,383; and 4,752,470.

In certain embodiments, a dosage form can comprise an osmotic dosage form, which comprises a semipermeable wall that surrounds a therapeutic composition comprising the compound. In use within a patient, an osmotic dosage form comprising a homogenous composition, imbibes fluid through the semipermeable wall into the dosage form in response to the concentration gradient across the semipermeable wall. The therapeutic composition in the dosage form develops osmotic pressure differential that causes the therapeutic composition to be administered through an exit from the dosage form over a prolonged period of time up to about 24 hours (or even in some cases up to about 30 hours) to provide controlled and sustained compound release. These delivery platforms can provide an essentially zero order delivery profile as opposed to the spiked profiles of immediate release formulations.

In certain embodiments, the dosage form can comprise another osmotic dosage form comprising a wall surrounding a compartment, the wall comprising a semipermeable polymeric composition permeable to the passage of fluid and substantially impermeable to the passage of compound present in the compartment, a compound-containing layer composition in the compartment, a hydrogel push layer composition in the compartment comprising an osmotic formulation for imbibing and absorbing fluid for expanding in size for pushing the compound composition layer from the dosage form, and at least one passageway in the wall for releasing the prodrug composition. The method delivers the compound by imbibing fluid through the semipermeable wall at a fluid imbibing rate determined by the permeability of the semipermeable wall and the osmotic pressure across the semipermeable wall causing the push layer to expand, thereby delivering the compound from the dosage form through the exit passageway to a patient over a prolonged period of time (up to about 24 or even about 30 hours). The hydrogel layer composition can comprise from about 10 mg to about 1000 mg of a hydrogel such as a member selected from the group consisting of a polyalkylene oxide of about 1,000,000 to about 8,000,000 weight-average molecular weight, which are selected from the group consisting of a polyethylene oxide of about 1,000,000 weight-average molecular weight, a polyethylene oxide of about 2,000,000 molecular weight, a polyethylene oxide of about 4,000,000 molecular weight, a polyethylene oxide of about 5,000,000 molecular weight, a polyethylene oxide of about 7,000,000 molecular weight and a polypropylene oxide of the about 1,000,000 to about 8,000,000 weight-average molecular weight; or about 10 mg to about 1000 mg of an alkali carboxymethylcellulose of about 10,000 to about 6,000,000 weight average molecular weight, such as sodium carboxymethylcellulose or potassium carboxymethylcellulose. The hydrogel expansion layer comprises about 0 mg to about 350 mg, in present manufacture; about 0.1 mg to about 250 mg of a hydroxyalkylcellulose of about 7,500 to about 4,500,00 weight-average molecular weight (e.g., hydroxymethylcellulose, hydroxyethylcellulose, hydroxypropylcellulose, hydroxybutylcellulose or hydroxypentylcellulose) in present manufacture; about 1 mg to about 50 mg of an agent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to about 5 mg of a colorant, such as ferric oxide; about 0 mg to about 30 mg, in present manufacture, 0.1 mg to 30 mg of a hydroxypropylalkylcellulose of about 9,000 to about 225,000 average-number molecular weight, selected from the group consisting of hydroxypropylethylcellulose, hydroxypropypentylcellulose, hydroxypropylmethylcellulose, and hydropropylbutylcellulose; about 0.00 to about 1.5 mg of an antioxidant selected from the group consisting of ascorbic acid, butylated hydroxyanisole, butylated hydroxyquinone, butylhydroxyanisol, hydroxycoumarin, butylated hydroxytoluene, cephalm, ethyl gallate, propyl gallate, octyl gallate, lauryl gallate, propyl-hydroxybenzoate, trihydroxybutylrophenone, dimethylphenol, dibutylphenol, vitamin E, lecithin, and ethanolamine; and about 0.0 mg to about 7 mg of a lubricant selected from the group consisting of calcium stearate, magnesium stearate, zinc stearate, magnesium oleate, calcium palmitate, sodium suberate, potassium laurate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

In the osmotic dosage forms, the semipermeable wall can comprise a composition that is permeable to the passage of fluid and impermeable to the passage of prodrug. The wall is nontoxic and comprises a polymer selected from the group consisting of a cellulose acylate, cellulose diacylate, cellulose triacylate, cellulose acetate, cellulose diacetate and cellulose triacetate. The wall comprises about from 75 wt % (weight percent) to about 100 wt % of the cellulosic wall-forming polymer or, the wall can comprise additionally about 0.01 wt % to about 80 wt % of polyethylene glycol, or about from 1 wt % to about 25 wt % of a cellulose ether selected from the group consisting of hydroxypropylcellulose and a hydroxypropylalkycellulose such as hydroxypropylmethylcellulose. The total weight percent of all components comprising the wall is equal to about 100 wt %. The internal compartment comprises the compound-containing composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of prodrug to a patient over time. The dosage form comprises a passageway in the wall that connects the exterior of the dosage form with the internal compartment. The osmotic powered dosage form can be made to deliver prodrug from the dosage form to the patient at a zero order rate of release over a period of up to about 24 hours.

The expression "passageway" as used herein comprises means and methods suitable for the metered release of the compound from the compartment of the dosage form. The exit means comprises at least one passageway, including an orifice, bore, aperture, pore, porous element, hollow fiber, capillary tube, channel, porous overlay, or porous element that provides for the osmotic controlled release of compound. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square, or elliptical, for the metered release of prodrug from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770; 3,916,899; 4,063,064; 4,088,864; and 4,816,263. Passageways formed by leaching are disclosed in U.S. Pat. Nos. 4,200,098 and 4,285,987.

Regardless of the specific form of sustained release oral dosage form used, compounds of Formula (I) can be released from the dosage form over a period of at least about 4 hours, for example, over a period of at least about 8 hours or at least about 12 hours. Further, in certain embodiments, the dosage form can release from about 0% to about 30% of the prodrug in from 0 to about 2 hours, from about 20% to about 50% of the prodrug in from about 2 to about 12 hours, from about 50% to about 85% of the prodrug in from about 3 to about 20 hours and greater than about 75% of the prodrug in from about 5 to about 18 hours. In certain embodiments, a sustained release oral dosage form can provide a concentration of tranexamic acid in the blood plasma of a patient over time, which curve has an area under the curve ($C_{max}$) that is proportional to the dose of the prodrug of tranexamic acid administered, and a maximum concentration $C_{max}$.

In certain embodiments, dosage forms are administered once or twice per day, and in certain embodiments, once per day.

Therapeutic Uses of Compounds, Compositions and Dosage Forms

In some embodiments, a therapeutically effective amount of one or more compounds of Formula (I) can be administered to a patient, such as a human, suffering from excessive bleeding, including heavy bleeding associated with cardiac surgery, upper gastrointestinal hemorrhage, blood loss in patients with advanced cancer, excess bleeding that occurs during dental procedures in hemophiliacs, and heavy bleeding during menstruation, i.e., menorrhagia. In certain embodiments, bleeding associated with these and other indications, can be considered heavy or excessive when the bleeding is greater than normal and will depend, at least in part, on the particular pathology and the judgment of the treating physician.

In certain embodiments, a therapeutically effective amount of one or more compounds of Formula (I) can be administered to a patient, such as a human, suffering from skin diseases or disorders such as wound healing, epidermal hyperplasia, skin roughening and unwanted skin pigmentation. In certain embodiments, a therapeutically effective amount of one or more compounds of Formula (I) can be administered to a patient, such as a human, suffering from cancer to treat or prevent tumor metastasis. In some of the above embodiments, sustained release oral dosage forms can be administered to the patient. In certain embodiments, topical formulations of one or more compounds of Formula (I) can be administered to the patient.

Further, in certain embodiments, a therapeutically effective amount of one or more compounds of Formula (I) can be administered to a patient, such as a human, as a preventative measure against various diseases or disorders. Thus, the therapeutically effective amount of one or more compounds of Formula (I) can be administered as a preventative measure to a patient having a predisposition for excessive bleeding, including, but not limited to, excessive bleeding associated with cardiac surgery, upper gastrointestinal hemorrhage, blood loss in patients with advanced cancer, excessive bleeding that occurs during dental procedures, for example in hemophiliacs, and excessive bleeding during menstruation, i.e., menorrhagia. In certain embodiments, the therapeutically effective amount of one or more compounds of Formula (I) can be administered as a preventive measure to a patient having a predisposition for skin disease and disorder including, but not limited to, wound healing, epidermal hyperplasia, skin roughening, and unwanted skin pigmentation. In certain embodiments, the therapeutically effective amount of one or more compounds of Formula (I) can be administered as a preventive measure to a patient having a predisposition for tumor metastasis.

When used to treat or prevent the above diseases or disorders a therapeutically effective amount of one or more compounds of Formula (I) can be administered or applied singly, or in combination with other agents. The therapeutically effective amount of one or more compounds of Formula (I) can also deliver a compound of Formula (I) in combination with another pharmaceutically active agent, including another compound of Formula (I). For example, in the treatment of a patient suffering from cancer, a dosage form comprising a compound of Formula (I) can be administered in conjunction with an anti-cancer agent, such as adriamycin, Alkeran, Aredia, Arimidex, Avastin, BiCNU, Bleomycin, Blenoxane, Camptosar, carboplatin, Casodex, Celestone, Cerubidine, cisplatin, Cosmegan, Cytosar U, Cytoxan, daunorubricin, DaunoXome, Didronel, diethylstilbestrol, Diflucan, Doxil, doxorubicin, Elspar, Emcyt, Epogen, ergamisol, Ethyol, Etopophos, Etoposide, Eulexin, Femara, Fludara, Fluorouracil, Gemzar, Gleevec, Gliade, Herceptin, Hexylen, Hycamtin, Hydrea, hydroxyurea, idamycin, Iflex, Intron A, Kytril, Leucovorin calcium, Leukeran, Leukine, Leustatin, Lupron, Lysodren, Marinol, Matulane, Mesnex, methotrexate, Mithracin, Mitoxantrosc, Mustargen, Mutamycin, Myleran, Navelbine, Neupogen, Nilandron, Nipent, Nolvadex, Novantrone, Oncaspar, Oncovin, oxaliplatin, Paraplatin, Photofrin, Platinol, Procrit, Proleukin, Purinethol, Rituxan, Roferon A, Rubex, Salagen, Sandostatin, squalamine, Tarcvea, Taxol, Taxotere, thioguanine, Thioplex, Tice BCG, TNP 470, Velban, Vesanoid, VePesid, Vitaxin, Vumon, Zanosar, Zinecard, Zofran, Zoladex, and Zyloprim.

In certain embodiments, in the treatment of a patient suffering from excessive bleeding, such as for example menorrhagia, a dosage form comprising a compound of Formula (I) can be administered in conjunction with an agent known or believed to be effective in treating excessive bleeding, including oral synthetic progestins such as medroxyprogesterone, norethindrone acetate, and norgestrel; natural progestins such as progesterone; gonadatrophin inhibitors such as danazol; or nonsteroidal anti-inflammatory agent such as aspirin, salsalate, diflunisal, ibuprofen, detaprofen, nabumetone, piroxicam, mefenamic acid, naproxen, diclofenac, indomethacin, sulindac, tolmetin, etodolac, ketorolac, oxaprozin, and COX-2 inhibitors such as celecoxib, meloxicam, and rofecoxib.

In certain embodiments, a compound of Formula (I) can be administered to a patient in combination with another antifibrinolytic agent such as desmopressin, aprotinin, ε-aminocaproic acid, a plasmin inhibitor, or another compound used to treat patients having excessive bleeding such as aluminum hydroxide, ranitidine, or goserelin.

In certain embodiments, compounds of Formula (I) are prodrugs of both tranexamic acid and a second therapeutic agent. The moiety having the structure:

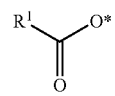

can comprise a second therapeutic agent having a —COOH group. In certain embodiments, the second therapeutic agent can be a compound effective treating a symptom associated with excessive bleeding. For example, in certain embodiments such as for treating menorrhagia, the second therapeutic agent can be a non-steroidal anti-inflammatory agent having a —COOH group such as aspirin, salsalate, diflunisal, ibuprofen, ketaprofen, mefenamic acid, naproxen, diclofenac, indomethacin, sulindac, tolmetin, etodolac, ketorolac, or oxaprozin. In certain embodiments, a compound of Formula (I) is a prodrug of tranexamic acid and a non-steroidal anti-inflammatory agent such as ibuprofen or naproxen.

Dosage forms, upon releasing a tranexamic acid prodrug of Formula (I), can provide tranexamic acid upon in vivo administration to a patient. The promoiety or promoieties of the prodrug of Formula (I) can be cleaved either chemically and/or enzymatically. One or more enzymes present in the stomach, intestinal lumen, intestinal tissue, blood, liver, brain or any other suitable tissue of a mammal can enzymatically cleave the promoiety or promoieties of the prodrug. If the promoiety or promoieties are cleaved after absorption by the gastrointestinal tract, tranexamic acid prodrugs of Formula (I) can be absorbed into the systemic circulation from the large intestine. In certain embodiments, the promoiety or promoieties are cleaved after absorption by the gastrointestinal tract. In certain embodiments, the promoiety or promoieties are cleaved in the gastrointestinal tract and tranexamic acid is absorbed into the systemic circulation form the large intestine. In certain embodiments, the tranexamic acid prodrug is absorbed into the systemic circulation from the gastrointestinal tract, and the promoiety or promoieties are cleaved in the systemic circulation, after absorption of the tranexamic acid prodrug from the gastrointestinal tract.

In certain embodiments, a tranexamic prodrug of Formula (I) can be provided to a patient by topical administration. For example, a pharmaceutical composition comprising at least on compound of Formula (I) and at least one pharmaceutically acceptable topical vehicle can be formulated in the form of a cream, lotion, ointment, solution, aerosol, spray and the like. The topical formulation can be applied to a surface area of a patient to be treated, for example, by spreading or spraying. The surface area of a patient to be treated can be an area exhibiting excessive or heavy bleeding such as a wound, oral mucosa, buccal mucosa, rectal mucosa, vaginal mucosa, nasal mucosa, surfaces exposed during surgery, or an area of the skin exhibiting a skin disease or disorder. In prophylactic applications, the surface area of a patient to be treated can be, for example, an area of a mucosa or the skin having a predisposition for a skin disease or disorder including, but not limited to, bleeding, epidermal hyperplasia, skin roughening, and unwanted skin pigmentation.

Doses

The amount of tranexamic acid prodrug that will be effective in the treatment of a particular disorder or condition disclosed herein can depend on the nature of the disorder or condition, and can be determined by standard clinical techniques known in the art. In addition, in vitro or in vivo assays can optionally be employed to help identify optimal dosage ranges. The amount of a compound administered can depend on, among other factors, the subject being treated, the weight of the subject, the severity of the affliction, the manner of administration, and the judgment of the prescribing physician.

In certain embodiments, a dosage form are adapted to be administered to a patient no more than twice per day, and in certain embodiments, only once per day. Dosing can be provided alone or in combination with other drugs and can continue as long as required for effective treatment of the disease state or disorder. When used to treat or prevent menorrhagia, a therapeutically effective amount of one or more compounds of Formula (I) can be administered concurrently with menstruation (typically for 4 to 7 days).

Suitable daily dosage ranges for oral administration can range from about 2 mg to about 50 mg of tranexamic acid equivalents per kilogram body weight. Suitable drug concentrations in formulations for topical administration can range from about 1% to about 10% (on a weight basis). Appropriate dosage ranges can be readily determined by methods known to the skilled artisan.

EXAMPLES

The following examples describe in detail preparation of compounds and compositions disclosed herein and assays for using compounds and compositions disclosed herein. It will be apparent to those of ordinary skill in the art that many modifications, both to materials and methods, may be practiced.

In the examples below, the following abbreviations have the following meanings. If an abbreviation is not defined, it has its generally accepted meaning.

DMSO=dimethylsulfoxide
g=gram
h=hour
HPLC=high pressure liquid chromatography
LC/MS=liquid chromatography/mass spectroscopy
M=molar
mg=milligram
min=minute
mL=milliliter
mmol=millimoles
MTBE=methyl tert-butyl ether
NMM=N-methylmorpholine
nM=nanomolar
µL=microliter
µM=micrometer
µM=micromolar
v/v=volume to volume
w/v=weight to volume General Experimental Protocols trans-4-(Aminomethyl)-cyclohexanecarboxylic acid (tranexamic acid) was purchased from Sigma-Aldrich, Inc. and was used without further manipulation. O-(1-Acyloxyalkyl) S-alkylthiocarbonates were previously synthesized according to the procedures disclosed in Gallop et al., U.S. Application Publication No. 2005/0222431 and converted to the corresponding acyloxyalkyl N-hydroxysuccinimide carbonic acid esters as described therein, or according to the general procedure given below. All other reagents and solvents were purchased from commercial suppliers and used without further purification or manipulation.

Proton NMR spectra (400 MHz) were recorded on a Varian AS 400 NMR spectrometer equipped with an autosampler and data processing computation. DMSO-$d^6$ (99.9% D) or CDCl$_3$ (99.8% D) were used as solvents unless otherwise noted. The DMSO or chloroform solvent signal was used for calibration of the individual spectra (H. E. Gottlieb et al., *J. Org. Chem.*, 1997, 62, 7512). Analytical LC/MS was performed on a Waters 2790 separation module equipped with a Waters Micromass QZ mass spectrometer, a Waters 996 photodiode detector, and a Merck Chromolith UM2072-027 or Phenomenex Luna C-18 analytical column. Mass-guided preparative HPLC purification of final compounds was performed on an instrument equipped with a Waters 600 controller, ZMD Micromass spectrometer, a Waters 2996 photodiode array detector, and a Waters 2700 Sample Manager. Acetonitrile/water gradients containing 0.05% formic acid were used as eluents in both analytical and preparative HPLC experiments.

General Procedure for the Synthesis of Acyloxyalkyl N-hydroxysuccinimide Carbonic Acid Esters A 250 mL round-bottomed flask equipped with a magnetic stir bar and a pressure-equilibrating dropping funnel was charged with the 1-acyloxyalkyl alkylthiocarbonate (10 mmol) and N-hydroxysuccinimide (20-40 mmol). Dichloromethane (20-40 mL) was added and the reaction mixture cooled to ca. 0° C. in an ice-bath. Peracetic acid (32 wt. %) in a 40-45% aqueous acetic acid solution (30 mmol) was added dropwise with stirring over a period of ca. one hour to the cooled solution. After addition was complete, stirring was continued for additional three to five hours at this temperature, the reaction being monitored by $^1$H NMR spectroscopy. After complete consumption of the starting material, the reaction mixture was diluted with additional dichloromethane, and the organic solution was washed successively with water (three times) and once with a 10% aqueous solution of sodium metabisulfite or sodium thiosulfate to quench any remaining oxidant. The combined organic extracts were dried over MgSO$_4$, filtered, and the solvent removed under reduced pressure with a rotary evaporator. Compound identity, integrity, and purity were checked by $^1$H NMR spectroscopy. The crude material was used directly in the next step, or could be further purified by commonly employed techniques well-known to those skilled in the art.

Example 1

1-[(2,5-Dioxopyrrolidinyl)oxycarbonyloxy]-propyl 2-methylpropanoate (2)

Following the above general procedure, 1-(ethylthiocarbonyloxy)-propyl 2-methylpropanoate (2.3 g, 9.82 mmol) and N-hydroxysuccinimide (4.6 g, 40 mmol) were reacted in dichloromethane (20 mL) with peracetic acid (32 wt. %, 6.13 mL). After aqueous workup, isolation and removal of residual solvents in vacuo, the crude product 2 (1.76 g, 61%) was obtained as a yellow oil. The material was used in the next step without further purification. $^1$H NMR (400 MHz, CDCl$_3$): δ=1.02 (t, J=7.6 Hz, 3H), 1.20 (d, J=6.8 Hz, 3H), 1.21 (d, J=7.2 Hz, 3H), 1.88-2.00 (m, 2H), 2.61 (hept., J=7.2 Hz, 1H), 2.84 (s, 4H), 6.71 (t, J=5.2 Hz, 1H).

Example 2

1-[(2,5-Dioxopyrrolidinyl)oxycarbonyloxy]-2-methylpropyl 2-methylpropanoate (3)

Following the above general procedure, 2-methyl-1-(methylthiocarbonyloxy)-propyl 2-methylpropanoate (2.34 g, 10.0 mmol) and N-hydroxysuccinimide (5.76 g, 50 mmol) were reacted in dichloromethane (30 mL) with peracetic acid (32 wt. %, 8.17 mL). After aqueous workup, isolation and removal of residual solvents in vacuo, the crude product 3 (2.12 g, 70%) was obtained as a pale yellow oil. The material was used in the next step without further purification. $^1$H NMR (400 MHz, CDCl$_3$): δ=1.04 (d, J=7.2 Hz, 6H), 1.21 (d, J=6.8 Hz, 3H), 1.22 (d, J=6.8 Hz, 3H), 2.15-2.21 (m, 1H), 2.63 (hept., J=7.2 Hz, 1H), 2.84 (s, 4H), 6.59 (d, J=5.2 Hz, 1H). MS (ESI) m/z 324.10 (M+Na)$^+$.

General Nucleophilic Carbamoylation Procedure for Synthesis of Acyloxyalkyl Carbamates of Tranexamic Acid A screw-capped 40 mL glass vial equipped with a magnetic stir bar was charged with trans-4-(aminomethyl)cyclohexanecarboxylic (tranexamic) acid (472 mg, 3.0 mmol). The appropriate acyloxyalkyl N-hydroxysuccinimide carbonic acid ester (2.0 mmol) was added either as a solid or was dissolved in a small volume of solvent (for oily materials). A mixture of methyl tert-butyl ether (MTBE), acetone, and water (v/v/v=4:3:1) (15-20 mL) was added, and the reaction mixture stirred for ca. 12 hours at room temperature. Upon completion of the reaction, the mixture was diluted with ethyl acetate and 1 N aqueous hydrochloric acid (ca. 10 mL) was added. After vigorous mixing followed by phase separation, the aqueous layer was extracted once more with EtOAc, and the combined organic extracts were washed with brine. The solvents were evaporated under reduced pressure, the dry residue was dissolved in a mixture of 60% (v/v) acetonitrile/water, and the solution filtered through a 0.2 μm nylon syringe filter. Final purification was achieved by mass-guided preparative HPLC. After lyophilization of the solvents, the pure compounds were obtained as white powders.

General Procedure for One Pot Synthesis of Acyloxyalkyl Carbamates of Tranexamic Acid Under an atmosphere of nitrogen, a dry 100 mL round-bottomed flask equipped with a magnetic stir bar and a rubber septum was charged with trans-4-(aminomethyl)cyclohexanecarboxylic (tranexamic) acid (786.1 mg, 5.0 mmol). Anhydrous dichloromethane (10-15 mL) was added, and the reaction mixture was cooled to ca. 0° C. with an icebath. Chlorotrimethylsilane (1.396 mL, 1.195 g, 11.0 mmol) was added neat at this temperature, followed by slow addition of N-methylmorpholine (1.374 mL, 1.264 g, 12.5 mmol). The reaction mixture was stirred at this temperature for ca. 30 min, when an appropriately substituted chloroalkylchloroformate (7.5 mmol) was added dropwise and in neat form. The reaction mixture was stirred at this temperature for an additional 30 min when a premixed mixture of NMM (2.75 mL, 2.53 g, 25 mmol) and an appropriately substituted carboxylic acid (50 mmol) was added at ca. 0° C. The reaction mixture was stirred overnight with warming to room temperature. The dichloromethane was removed in vacuo from the dark brownish reaction mixture using a rotary evaporator. The crude reaction product was diluted with methyl tert-butyl ether (MTBE), and the solution washed three times with water. The organic layer was dried over MgSO$_4$, and the filtrate evaporated in vacuo using a rotary evaporator. The crude dry residue was dissolved in a small amount of a mixture of 60% (v/v) acetonitrile/water (ca. 5 mL), and the solution filtered through a 0.2 μm nylon syringe filter. Final purification was achieved by mass-guided preparative HPLC. After lyophilization of the solvents, the pure compounds were generally obtained as white powders.

General Procedure for the Synthesis of Sodium Salts of Acyloxyalkyl Carbamates of Tranexamic Acid A screw-capped 40 mL vial equipped with a magnetic stir bar was charged with an appropriately substituted acyloxyalkyl carbamate of tranexamic acid (5.0 mmol). The material was dissolved in ca. 10 mL of acetonitrile. A solution of sodium bicarbonate (NaHCO$_3$) (420.1 mg, 5.0 mmol) in ca. 20 mL of water was added at room temperature and the mixture was stirred one hour after the evolution of carbon dioxide subsided. The clear solution was frozen at −78° C. and the solvents were lyophilized. After lyophilization of the solvents, the pure compounds were obtained as white powders.

Example 3 trans-4-{[(2-Methylpropanoyloxy)methoxycarbonyl]aminomethyl}-Cyclohexanecarboxylic Acid (4)

Following the general nucleophilic carbamoylation procedure, tranexamic acid (472 mg, 3.0 mmol) and 1-[(2,5-dioxopyrrolidinyl)oxycarbonyloxy]methyl 2-methylpropanoate (518 mg, 2.0 mmol) were reacted in the MTBE/acetone/water mixture (16 mL) to yield the title compound 4 (397 mg, 66% yield) as a white powder after work-up and mass-guided preparative HPLC purification. $^1$H NMR (400 MHz, DMSO-d$^6$): δ=0.82-0.95 (br. m, 2H), 1.08 (d, J=7.2 Hz, 6H), 1.17-1.39 (br. m, 3H), 1.64-1.73 (br. m, 2H), 1.82-1.91 (br. m, 2H), 2.10 (tt, J=11.8, 3.8 Hz, 1H), 2.55 (hept., J=7.2 Hz, 1H), 2.78-2.88 (br. m, 2H), 5.61 (s, 2H), 7.55 (t, J=5.6 Hz, 1H), 11.98 (br. s, 1H). MS (ESI) m/z 302.09 (M+H)$^+$; 299.99 (M−H)$^-$.

Example 4 trans-4-{[(3-Methylbutanoyloxy)methoxycarbonyl]aminomethyl}-Cyclohexanecarboxylic Acid (5)

Following the general nucleophilic carbamoylation procedure, tranexamic acid (472 mg, 3.0 mmol) and 1-[(2,5-dioxopyrrolidinyl)oxycarbonyloxy]methyl 3-methylbutanoate (547 mg, 2.0 mmol) were reacted in the MTBE/acetone/water mixture (16 mL) to yield the title compound 5 (310 mg, 49% yield) as a white powder after work-up and mass-guided preparative HPLC purification. $^1$H NMR (400 MHz, DMSO-$d^6$): δ=0.86-0.94 (br. m, 8H), 1.17-1.38 (br. m, 3H), 1.64-1.72 (br. m, 2H), 1.83-1.91 (br. m, 2H), 1.96 (hept., J=7.2 Hz, 1H), 2.09 (tt, J=12.4, 3.6 Hz, 1H), 2.21 (d, J=6.8 Hz, 2H), 2.78-2.86 (br. m, 2H), 5.61 (s, 2H), 7.55 (t, J=5.6 Hz, 1H), 11.99 (br. s, 1H). MS (ESI) m/z 316.11 (M+H)$^+$; 314.07 (M−H)$^−$.

Example 5 trans-4-{[(2,2-Dimethylpropanoyloxy)methoxycarbonyl]-aminomethyl}-Cyclohexanecarboxylic Acid (6)

Following the general nucleophilic carbamoylation procedure, tranexamic acid (472 mg, 3.0 mmol) and 1-[(2,5-dioxopyrrolidinyl)oxycarbonyloxy]methyl 2,2-dimethylpropanoate (547 mg, 2.0 mmol) were reacted in the MTBE/acetone/water mixture (16 mL) to yield the title compound 6 (476 mg, 76% yield) as a white powder after work-up and mass-guided preparative HPLC purification. $^1$H NMR (400 MHz, DMSO-$d^6$): δ=0.82-0.94 (br. m, 2H), 1.13 (s, 9H), 1.17-1.38 (br. m, 3H), 1.64-1.72 (br. m, 2H), 1.82-1.91 (br. m, 2H), 2.09 (tt, J=12.0, 3.6 Hz, 1H), 2.78-2.87 (br. m, 2H), 5.61 (s, 2H), 7.54 (t, J=5.6 Hz, 1H), 11.98 (br. s, 1H). MS (ESI) m/z 316.11 (M+H)$^+$; 314.01 (M−H)$^−$.

Example 6 trans-4-{-[(Benzoyloxy)methoxycarbonyl]aminomethyl}-Cyclohexanecarboxylic Acid (7)

Following the general nucleophilic carbamoylation procedure, tranexamic acid (472 mg, 3.0 mmol) and 1-[(2,5-dioxopyrrolidinyl)oxycarbonyloxy]methyl benzoate (587 mg, 2.0 mmol) were reacted in the MTBE/acetone/water mixture (16 mL) to yield the title compound 7 (445 mg, 66% yield) a white powder after work-up and mass-guided preparative HPLC purification. $^1$H NMR (400 MHz, DMSO-$d^6$): δ=0.83-0.95 (br. m, 2H), 1.16-1.39 (br. m, 3H), 1.65-1.72 (br. M, 2H), 1.82-1.91 (br. m, 2H), 2.09 (tt, J=12.4, 3.6 Hz, 1H), 2.81-2.88 (br. m, 2H), 5.88 (s, 2H), 7.50-7.57 (m, 2H), 7.61 (t, J=6.0 Hz, 1H), 7.65-7.70 (m, 1H), 7.93-7.97 (m, 2H), 11.96 (br. s, 1H). MS (ESI) m/z 336.01 (M+H)$^+$; 333.98 (M−H)$^−$.

Example 7 trans-4-{[1-(Acetoxy)ethoxycarbonyl]aminomethyl}-Cyclohexanecarboxylic Acid (8)

Following the general procedure for the one pot synthesis, tranexamic acid (786 mg, 5.0 mmol) was reacted with chlorotrimethylsilane (1.396 mL, 1.195 g, 11.0 mmol) in anhydrous dichloromethane (10 mL) and in the presence of N-methylmorpholine (1.374 mL, 1.264 g, 12.5 mmol). Subsequent reaction of the intermediate with 1-chloroethylchloroformate (0.82 mL, 1.07 g, 7.5 mmol) followed by a mixture of NMM (2.75 mL, 2.53 g, 25 mmol) and acetic acid (2.86 mL, 3.00 g, 50 mmol) yielded the title compound 8 (320 mg, 22% yield) as a very slightly orange-colored oil after aqueous work-up and mass-guided preparative HPLC purification. $^1$H NMR (400 MHz, DMSO-$d^6$): δ=0.82-0.94 (br. m, 2H), 1.17-1.35 (br. m, 3H), 1.38 (d, J=5.2 Hz, 3H), 1.66-1.73 (br. m, 2H), 1.84-1.91 (br. m, 2H), 1.99 (s, 3H), 2.10 (tt, J=12.0, 3.6 Hz, 1H), 2.74-2.88 (m, 2H), 6.62 (q, J=5.2 Hz, 1H), 7.44 (t, J=6.0 Hz, 1H), 11.97 (br. s, 1H). MS (ESI) m/z 310.12 (M+Na)$^+$; 286.08 (M−H)$^−$.

Example 8 trans-4-{[1-(Propanoyloxy)ethoxycarbonyl]aminomethyl}-Cyclohexanecarboxylic Acid (9)

Following the general procedure for the one pot synthesis, tranexamic acid (786 mg, 5.0 mmol) was reacted with chlorotrimethylsilane (1.396 mL, 1.195 g, 11.0 mmol) in anhydrous dichloromethane (10 mL) and in the presence of N-methylmorpholine (1.374 mL, 1.264 g, 12.5 mmol). Subsequent reaction of the intermediate with chloroethylchloroformate (0.82 mL, 1.07 g, 7.5 mmol) followed by a mixture of NMM (2.75 mL, 2.53 g, 25 mmol) and propionic acid (3.73 mL, 3.70 g, 50 mmol) yielded the title compound 9 (103 mg, 7% yield) as colorless, very viscous oil after aqueous work-up and two mass-guided preparative HPLC purifications. $^1$H NMR (400 MHz, DMSO-$d^6$): δ=0.82-0.94 (br. m, 2H), 1.03 (t, J=7.6 Hz, 3H), 1.17-1.35 (br. m, 3H), 1.38 (d, J=5.2 Hz, 3H), 1.65-1.73 (br. m, 2H), 1.83-1.91 (br. m, 2H), 2.09 (tt, J=12.4, 3.6 Hz, 1H), 2.26-2.33 (m, 2H), 2.74-2.90 (m, 2H), 6.64 (q, J=5.6 Hz, 1H), 7.44 (t, J=5.6 Hz, 1H), 11.99 (br. s, 1H). MS (ESI) m/z 324.14 (M+Na)$^+$; 300.10 (M−H)$^−$.

Example 9 trans-4-{[1-(Butanoyloxy)ethoxycarbonyl]aminomethyl}-Cyclohexanecarboxylic Acid (10)

Following the general nucleophilic carbamoylation procedure, tranexamic acid (800 mg, 5 mmol) and 1-[(2,5-dioxopyrrolidinyl)oxycarbonyloxy]ethyl butanoate (700 mg, 2.6 mmol) were reacted in the MTBE/acetone/water mixture (16 mL) to yield the title compound 10 (200 mg, 28% yield) as a white powder after work-up and mass-guided preparative HPLC purification. $^1$H NMR (400 MHz, DMSO-$d^6$): δ=0.89-0.97 (m, 5H), 1.22-1.36 (br. m, 3H), 1.42 (d, J=5.6 Hz, 3H), 1.51-1.60 (m, 2H), 1.72-1.73 (br. m, 2H), 1.90-1.93 (m, 2H), 2.13 (tt, J=12, 3.6 Hz, 1H), 2.29 (t, J=6.8 Hz, 2H), 2.85 (t, J=6.4 Hz, 2H), 6.69 (q, J=5.6 Hz, 1H), 7.48 (t, J=6.0 Hz, 1H), 12.03 (br. s, 1H). MS (ESI) m/z 338.15 (M+Na)$^+$; 314.12 (M−H)$^−$.

Example 10

Sodium trans-4-{[1-(Butanoyloxy)ethoxycarbonyl]aminomethyl}-Cyclohexanecarboxylate (11)

Following the general procedure for the formation of the corresponding sodium carboxylates of acyloxyalkyl carbamates of tranexamic acid, 946 mg (3.0 mmol) of trans-4-{[1-(butanoyloxy)ethoxycarbonyl]aminomethyl}-cyclohexanecarboxylic acid 10 was reacted with 252 mg (3.0 mmol) of sodium bicarbonate (NaHCO$_3$) in 20 mL of a mixture of acetonitrile and water (1:1) to yield 1.02 g (quant.) of the title compound 11 as a colorless powder. $^1$H NMR (400 MHz, DMSO-$d^6$): δ=0.73-0.84 (m, 2H), 0.87 (t, J=6.8 hz, 3H) 1.08-1.20 (m, 2H), 1.20-1.32 (m, 1H), 1.38 (d, J=5.2 Hz, 3H), 1.46-1.56 (m, 2H), 1.60-1.74 (br. m, 3H), 1.76-1.83 (br. m, 2H), 2.25 (t, J=7.2 Hz, 2H), 2.78 (t, J=6.0 Hz, 2H), 6.65 (q, J=5.2 Hz, 1H), 7.41 (t, J=5.6 Hz, 1H). MS (ESI) m/z 338.16 (M+Na)$^+$; 314.18 (M−H)$^−$.

Example 11 trans-4-{[1-(Pentanoyloxy)ethoxycarbonyl]aminomethyl}-Cyclohexanecarboxylic Acid (12)

Following the general nucleophilic carbamoylation procedure, tranexamic acid (1.1 g, 7.0 mmol) and 1-[(2,5-dioxopyrrolidinyl)oxycarbonyloxy]ethyl pentanoate (800 mg, 2.8 mmol) were reacted in the MTBE/acetone/water mixture (16 mL) to yield the title compound 12 (150 mg, 16% yield) as a white powder after work-up and mass-guided preparative HPLC purification. $^1$H NMR (400 MHz, DMSO-d$^6$): δ=0.88-0.97 (m, 5H), 1.22-1.38 (br. m, 5H), 1.42 (d, J=5.2 Hz, 3H), 1.44-1.56 (m, 2H), 1.72-1.74 (m, 2H), 1.90-1.93 (m, 2H), 2.13 (tt, J=12, 3.6 Hz, 1H), 2.30 (t, J=7.2 Hz, 2H), 2.85 (t, J=6.4 Hz, 2H), 6.68 (q, J=5.6 Hz, 1H), 7.47 (t, J=6.0 Hz, 1H), 12.01 (br. s, 1H). MS (ESI) m/z 352.18 (M+Na)$^+$; 328.14 (M−H)$^−$.

Example 12 trans-4-{[1-(2-Methylpropanoyloxy)ethoxycarbonyl]-aminomethyl}-Cyclohexanecarboxylic Acid (13)

Following the general nucleophilic carbamoylation procedure, tranexamic acid and 1-[(2,5-dioxopyrrolidinyl)oxycarbonyloxy]ethyl 2-methylpropanoate were reacted to yield the title compound 13 (333 mg, 53% yield) as a colorless powder after work-up and mass-guided preparative HPLC purification. $^1$H NMR (400 MHz, DMSO-d$^6$): d=0.82-0.94 (br. m, 2H), 1.058 (d, J=6.4 Hz, 3H), 1.062 (d, J=6.8 Hz, 3H), 1.17-1.36 (br. m, 3H), 1.38 (d, J=5.6 Hz, 3H), 1.65-1.73 (br. m, 2H), 1.83-1.91 (br. m, 2H), 2.10 (tt, J=12.0, 3.6 Hz, 1H), 2.49 (hept., J=6.8 Hz, 1H), 2.77-2.85 (br. m, 2H), 6.62 (q, J=5.2 Hz, 1H), 7.45 (t, J=6.0 Hz, 1H), 11.97 (br. s, 1H). MS (ESI) m/z 338.08 (M+Na)$^+$; 314.01 (M−H)$^−$.

Example 13

Sodium trans-4-{[1-(2-Methylpropanoyloxy)eth oxycarbonyl]-aminomethyl}-Cyclohexanecarboxylate (14)

Following the general procedure for the formation of the corresponding sodium carboxylates of acyloxyalkyl carbamates of tranexamic acid, 5.03 g (15.94 mmol) of trans-4-{[1-(2-methylpropanoyloxy)ethoxycarbonyl]-aminomethyl}-cyclohexanecarboxylic acid 13 was reacted with 1.34 g (15.94 mmol) of sodium bicarbonate (NaHCO$_3$) in 40 mL of a mixture of acetonitrile and water (1:1) to yield 5.38 g (quant.) of the title compound 14 as a colorless powder. $^1$H NMR (400 MHz, DMSO-d$^6$): δ=0.72-0.84 (br. m, 2H), 1.057 (d, J=6.4 Hz, 3H), 1.059 (d, J=6.8 Hz, 3H), 1.20-1.32 (br. m, 3H), 1.38 (d, J=5.2 Hz, 3H), 1.59-1.73 (br. m, 3H), 1.75-1.83 (m, 2H), 2.43-2.53 (m, 1H), 2.72-2.84 (br. m, 2H), 6.62 (q, J=5.6 Hz, 1H), 7.42 (t, J=5.6 Hz, 1H). MS (ESI) m/z 338.16 (M+Na)$^+$; 314.12 (M−H)$^−$.

Example 14

(+)-trans-4-({[(1S)-1-(2-Methylpropanoyloxy) ethoxy]carbonylamino}methyl)-Cyclohexanecarboxylic Acid (15)

The enantiomers of trans-4-{[1-(2-methylpropanoyloxy) ethoxycarbonyl]-aminomethyl}-cyclohexanecarboxylic acid 13 were resolved by means of a Waters mass-guided preparative HPLC using a ChiralPak AD-RH 250×20 mm column, an isocratic eluent of 30% acetonitrile/70% water/0.05% formic acid, and a flowrate of 15 mL/min. The enantiomeric excesses were determined with an analytical Waters 2690/ZQ LC/MS apparatus using a ChiralPak AD-RH column, an isocratic eluent consisting of 30% acetonitrile/70% water/0.05% formic acid, and a flowrate of 60 μL/min. 529 mg of the title compound 15 was obtained as a colorless powder after lyophilization [R$_f$=12.2 min; e.e. =98.3%; [α]$_D^{25.8}$=+18.64, c (19.97, MeOH)]. The assignment of the absolute configuration was accomplished by comparison with material obtained from an independent synthesis. $^1$H NMR (400 MHz, DMSO-d$^6$): δ=0.82-0.94 (br. m, 2H), 1.057 (d, J=6.8 Hz, 3H), 1.061 (d, J=6.8 Hz, 3H), 1.17-1.36 (br. m, 3H), 1.38 (d, J=5.6 Hz, 3H), 1.65-1.73 (br. m, 2H), 1.83-1.91 (br. m, 2H), 2.10 (tt, J=12.0, 3.6 Hz, 1H), 2.49 (hept., J=6.8 Hz, 1H), 2.77-2.85 (br. m, 2H), 6.62 (q, J=5.2 Hz, 1H), 7.45 (t, J=6.0 Hz, 1H), 11.97 (br. s, 1H). MS (ESI) m/z 338.16 (M+Na)$^+$; 314.12 (M−H)$^−$.

Example 15

Sodium trans-4-({[(1S)-1-(2-methylpropanoyloxy) ethoxy]carbonylamino}methyl)-Cyclohexanecarboxylate (16)

Following the general procedure for the formation of the corresponding sodium carboxylates of acyloxyalkyl carbamates of tranexamic acid, 90.0 mg (0.2854 mmol) of (+)-trans-4-({[(1S)-1-(2-methylpropanoyloxy)ethoxy] carbonylamino}methyl)-cyclohexanecarboxylic acid 15 was reacted with 24.0 mg (0.2854 mmol) of sodium bicarbonate (NaHCO$_3$) in 4 mL of a mixture of acetonitrile and water (1:1) to yield 96.3 mg (quant.) of the title compound 16 as a colorless powder. The enantiomeric excesses were determined with an analytical Waters 2690/ZQ LC/MS apparatus using a ChiralPak AD-RH column, an isocratic eluent consisting of 30% acetonitrile/70% water/0.05% formic acid, and a flowrate of 60 μL/min (R$_f$=12.1 min; e.e. =98.5%). $^1$H NMR (400 MHz, DMSO-d$^6$): δ=0.72-0.84 (br. m, 2H), 1.057 (d, J=6.4 Hz, 3H), 1.059 (d, J=6.8 Hz, 3H), 1.20-1.32 (br. m, 3H), 1.38 (d, J=5.2 Hz, 3H), 1.59-1.73 (br. m, 3H), 1.75-1.83 (m, 2H), 2.43-2.53 (m, 1H), 2.72-2.84 (br. m, 2H), 6.62 (q, J=5.6 Hz, 1H), 7.42 (t, J=5.6 Hz, 1H). MS (ESI) m/z 338.16 (M+Na)$^+$; 314.12 (M−H)$^−$.

Example 16

(−)-trans-4-({[(1R)-1-(2-Methylpropanoyloxy) ethoxy]carbonylamino}methyl)-Cyclohexanecarboxylic Acid (17)

The enantiomers of trans-4-{[1-(2-methylpropanoyloxy) ethoxycarbonyl]-aminomethyl}-cyclohexanecarboxylic acid 13 were resolved by means of a Waters mass-guided preparative HPLC using a ChiralPak AD-RH 250×20 mm column, an isocratic eluent of 30% acetonitrile/70% water/0.05% formic acid, and a flowrate of 15 mL/min. The enantiomeric excesses were determined with an analytical Waters 2690/ZQ LC/MS apparatus using a ChiralPak AD-RH column, an isocratic eluent consisting of 30% acetonitrile/70% water/0.05% formic acid, and a flowrate of 60 μL/min. 310 mg of the title compound 17 was obtained as a colorless powder after lyophilization [R$_f$=15.1 min; e.e. =97.6%; [α]$_D^{25.5}$=−14.94, c (24.30, MeOH)]. The assignment of the absolute configuration was accomplished by comparison with material obtained from an independent synthesis. $^1$H NMR (400 MHz, DMSO-d$^6$): δ=0.82-0.94 (br. m, 2H), 1.057 (d, J=6.8 Hz, 3H), 1.061

51

(d, J=6.8 Hz, 3H), 1.17-1.36 (br. m, 3H), 1.38 (d, J=5.6 Hz, 3H), 1.65-1.73 (br. m, 2H), 1.83-1.91 (br. m, 2H), 2.10 (tt, J=12.0, 3.6 Hz, 1H), 2.49 (hept., J=6.8 Hz, 1H), 2.77-2.85 (br. m, 2H), 6.62 (q, J=5.2 Hz, 1H), 7.45 (t, J=6.0 Hz, 1H), 11.97 (br. s, 1H). MS (ESI) m/z 338.16 (M+Na)$^+$; 314.12 (M–H)$^-$.

Example 17

Sodium trans-4-({[(1R)-1-(2-Methylpropanoyloxy) ethoxy]carbonylamino}methyl)-Cyclohexanecarboxylate (18)

Following the general procedure for the formation of the corresponding sodium carboxylates of acyloxyalkyl carbamates of tranexamic acid, 90.0 mg (0.2854 mmol) of (–)-trans-4-({[(1R)-1-(2-methylpropanoyloxy)ethoxy]carbonylamino}methyl)-cyclohexanecarboxylic acid 17 was reacted with 24.0 mg (0.2854 mmol) of sodium bicarbonate (NaHCO$_3$) in 4 mL of a mixture of acetonitrile and water (1:1) to yield 96.3 mg (quant.) of the title compound 18 as a colorless powder. The enantiomeric excesses were determined with an analytical Waters 2690/ZQ LC/MS apparatus using a ChiralPak AD-RH column, an isocratic eluent consisting of 30% acetonitrile/70% water/0.05% formic acid, and a flow-rate of 60 µL/min (R$_f$=15.0 min; e.e. =97.7%). $^1$H NMR (400 MHz, DMSO-d$^6$): δ=0.72-0.84 (br. m, 2H), 1.057 (d, J=6.4 Hz, 3H), 1.059 (d, J=6.8 Hz, 3H), 1.20-1.32 (br. m, 3H), 1.38 (d, J=5.2 Hz, 3H), 1.59-1.73 (br. m, 3H), 1.75-1.83 (m, 2H), 2.43-2.53 (m, 1H), 2.72-2.84 (br. m, 2H), 6.62 (q, J=5.6 Hz, 1H), 7.42 (t, J=5.6 Hz, 1H). MS (ESI) m/z 338.16 (M+Na)$^+$; 314.12 (M–H)$^-$.

Example 18 trans-4-{[1-(3-Methylbutanoyloxy)ethoxycarbonyl] aminomethyl}-Cyclohexanecarboxylic Acid (19)

Following the general nucleophilic carbamoylation procedure, tranexamic acid (900 mg, 6 mmol) and 1-[(2,5-dioxopyrrolidinyl)oxycarbonyloxy]ethyl 3-methylbutanoate (800 mg, 2.8 mmol) were reacted in the MTBE/acetone/water mixture (16 mL) to yield the title compound 19 (200 mg, 21% yield) as a white powder after work-up and mass-guided preparative HPLC purification. $^1$H NMR (400 MHz, DMSO-d$^6$): δ=0.88-0.97 (m, 8H), 1.22-1.38 (br. m, 3H), 1.42 (d, J=5.2 Hz, 3H), 1.71-1.74 (m, 2H), 1.90-2.02 (br. m, 3H), 2.1-2.2 (br. m, 3H), 2.85 (t, J=6.4 Hz, 2H), 6.69 (q, J=5.6 Hz, 1H), 7.48 (t, J=6.0 Hz, 1H), 12.01 (br. s, 1H). MS (ESI) m/z 352.15 (M+Na)$^+$; 328.14 (M–H)$^-$.

Example 19

Sodium trans-4-{[1-(3-Methylbutanoyloxy)ethoxycarbonyl]aminomethyl}-Cyclohexane carboxylate (20)

Following the general procedure for the formation of the corresponding sodium carboxylates of acyloxyalkyl carbamates of tranexamic acid, 1.976 g (6.0 mmol) of trans-4-{[1-(3-methylbutanoyloxy)ethoxycarbonyl]aminomethyl}-cyclohexanecarboxylic acid 19 was reacted with 504.1 mg (6.0 mmol) of sodium bicarbonate (NaHCO$_3$) in 20 mL of a mixture of acetonitrile and water (1:1) to yield 2.11 g (quant.) of the title compound 20 as a colorless powder. $^1$H NMR (400 MHz, DMSO-d$^6$): δ=0.72-0.84 (m, 2H), 0.89 (d, J=6.4 Hz, 6H), 1.07-1.21 (m, 2H), 1.22-1.32 (m, 3H), 1.38 (d, J=5.2 Hz, 3H), 1.58-1.74 (br. m, 3H), 1.76-1.84 (br. m, 2H), 1.88-2.01

52

(m, 1H), 2.08-2.20 (m, 2H), 2.74-2.85 (m, 2H), 6.66 (q, J=5.6 Hz, 1H), 7.42 (t, J=6.4 Hz, 1H). MS (ESI) m/z 352.18 (M+Na)$^+$; 328.14 (M–H)$^-$.

Example 20 trans-4-{[1-(2,2-Dimethylpropanoyloxy)-ethoxycarbonyl]aminomethyl}-Cyclohexanecarboxylic Acid (21)

Following the general nucleophilic carbamoylation procedure, tranexamic acid (1.1 g, 7 mmol) and 1-[(2,5-dioxopyrrolidinyl)oxycarbonyloxy]ethyl 2,2-dimethylpropanoate (1.1 g, 3.8 mmol) were reacted in the MTBE/acetone/water mixture (16 mL) to yield the title compound 21 (200 mg, 16% yield) as a white powder after work-up and mass-guided preparative HPLC purification. $^1$H NMR (400 MHz, DMSO-d$^6$): δ=0.86-0.99 (m, 2H), 1.14 (s, 9H), 1.21-1.39 (br. m, 3H), 1.42 (d, J=5.2 Hz, 3H), 1.71-1.74 (m, 2H), 1.89-1.91 (m, 2H), 2.13 (tt, J=12, 3.6 Hz, 1H), 2.81-2.89 (m, 2H), 6.64 (q, J=5.6 Hz, 1H), 7.49 (t, J=6.0 Hz, 1H), 12.01 (br. s, 1H). MS (ESI) m/z 352.16 (M+Na)$^+$; 328.14 (M–H)$^-$.

Example 21 trans-4-{[1-(Cyclohexylcarbonyloxy)ethoxycarbonyl]aminomethyl}-Cyclohexanecarboxylic Acid (22)

Following the general nucleophilic carbamoylation procedure, tranexamic acid (780 mg, 5.0 mmol) and 1-[(2,5-dioxopyrrolidinyl)oxycarbonyloxy]ethyl cyclohexanecarboxylate (700 mg, 2.2 mmol) were reacted in the MTBE/acetone/water mixture (16 mL) to yield the title compound 22 (200 mg, 26% yield) as a white powder after work-up and mass-guided preparative HPLC purification. $^1$H NMR (400 MHz, DMSO-d$^6$): δ=0.87-0.99 (m, 2H), 1.20-1.44 (br. m, 11H), 1.58-1.81 (m, 7H), 1.89-1.92 (m, 2H), 2.13 (tt, J=12, 3.6 Hz, 1H), 2.27-2.35 (m, 1H), 2.79-2.90 (m, 2H), 6.66 (q, J=5.6 Hz, 1H), 7.48 (t, J=6.0 Hz, 1H), 12.05 (br. s, 1H). MS (ESI) m/z 378.13 (M+Na)$^+$; 354.15 (M–H)$^-$.

Example 22 trans-4-{[1-(Benzoyloxy)ethoxycarbonyl]aminomethyl}-Cyclohexanecarboxylic Acid (23)

Following the general nucleophilic carbamoylation procedure, tranexamic acid (1.1 g, 7.0 mmol) and 1-[(2,5-dioxopyrrolidinyl)oxycarbonyloxy]ethyl benzoate (800 mg, 2.6 mmol) were reacted in the MTBE/acetone/water mixture (16 mL) to yield the title compound 23 (160 mg, 18% yield) as a white powder after work-up and mass-guided preparative HPLC purification. $^1$H NMR (400 MHz, DMSO-d$^6$): δ=0.87-0.96 (m, 2H), 1.21-1.38 (br. m, 3H), 1.57 (d, J=5.6 Hz, 3H), 1.71-1.74 (m, 2H), 1.88-1.91 (m, 2H), 2.1-2.2 (m, 1H), 2.84-2.88 (m, 2H), 6.92 (q, J=5.6 Hz, 1H), 7.54-7.58 (m, 3H), 7.70 (m, 1H), 7.94-7.96 (m, 2H), 12.05 (br. s, 1H). MS (ESI) m/z 372.10 (M+Na)$^+$; 348.05 (M–H)$^-$.

Example 23

Sodium trans-4-{[1-(Benzoyloxy)ethoxycarbonyl] aminomethyl}-Cyclohexanecarboxylate (24)

Following the general nucleophilic carbamoylation procedure for the formation of the corresponding sodium carboxylates of acyloxyalkyl carbamates of tranexamic acid, 2.096 g (6.0 mmol) of trans-4-{[1-(benzoyloxy)ethoxycarbonyl]aminomethyl}-cyclohexanecarboxylic acid 23 was reacted with 504.1 mg (6.0 mmol) of sodium bicarbonate ($NaHCO_3$) in 20 mL of a mixture of acetonitrile and water (1:1) to yield 2.23 g (quant.) of the title compound 24 as a colorless powder. $^1H$ NMR (400 MHz, DMSO-$d^6$): δ=0.72-0.86 (m, 2H), 1.08-1.21 (m, 2H), 1.22-1.32 (m, 1H), 1.53 (d, J=5.6 Hz, 3H), 1.59-1.84 (br. m, 5H), 2.73-2.86 (m, 2H), 6.88 (q, J=5.6 Hz, 1H), 7.47-7.56 (m, 3H), 7.64-7.70 (m, 1H), 7.89-7.94 (m, 2H). MS (ESI) m/z 372.10 $(M+Na)^+$; 348.12 $(M-H)^-$.

Example 24 trans-4-{[1-(2-Methylbenzovloxy)ethoxycarbonyl]aminomethyl}-Cyclohexanecarboxylic Acid (25)

Following the general nucleophilic carbamoylation procedure, tranexamic acid (780 mg, 5.0 mmol) and 1-[(2,5-dioxopyrrolidinyl)oxycarbonyloxy]ethyl 2-methylbenzoate (700 mg, 2.2 mmol) were reacted in the MTBE/acetone/water mixture (16 mL) to yield the title compound 25 (290 mg, 36% yield) as a white powder after work-up and mass-guided preparative HPLC purification. $^1H$ NMR (400 MHz, DMSO-$d^6$): δ=0.88-0.97 (m, 2H), 1.22-1.38 (br. m, 3H), 1.57 (d, J=5.6 Hz, 3H), 1.72-1.76 (m, 2H), 1.89-1.92 (m, 2H), 2.13 (tt, J=12, 3.6 Hz, 1H), 2.50 (s, 3H), 2.87 (t, J=2.8 Hz, 2H), 6.89 (q, J=5.6 Hz, 1H), 7.32-7.37 (m, 2H), 7.50-7.59 (m, 2H), 7.77 (dd, J=7.2, 1.2 Hz, 1H), 12.00 (s, 1H). MS (ESI) m/z 386.12 $(M+Na)^+$; 362.07 $(M-H)^-$.

Example 25 trans-4-{[({2-[4-(2-Methylpropyl)phenyl]propanoyloxy}ethoxy)carbonylamino]methyl}Cyclohexanecarboxylic Acid (26)

Following the general nucleophilic carbamoylation procedure, tranexamic acid (629 mg, 4.0 mmol) and 1-[(2,5-dioxopyrrolidinyl)oxycarbonyloxy]ethyl 2-[4-(2-methylpropyl)phenyl]propanoate (665 mg, 1.7 mmol) were reacted in the MTBE/acetone/water mixture (32 mL) to yield the title compound 26 (344 mg, 47% yield) as a colorless powder after work-up and mass-guided preparative HPLC purification. $^1H$ NMR (400 MHz, DMSO-$d^6$): δ=0.79-0.95 (m, 8H), 1.16-1.39 (m, 9H), 1.60-1.92 (m, 5H), 2.02-2.15 (m, 1H), 2.38-2.44 (m, 2H), 2.70-2.86 (m, 2H), 3.68-3.76 (m, 1H), 6.62-6.72 (m, 1H), 7.04-7.18 (m, 4H), 7.32-7.50 (m, 1H), 11.98 (br. s, 1H). MS (ESI) m/z 456.24 $(M+Na)^+$; 432.19 $(M-H)^-$.

Example 26 trans-4-[({[(2S)-2-(6-Methoxy(2-naphthyl))propanoyloxy]ethoxy}carbonylamino)methyl]Cyclohexanecarboxylic Acid (27)

Following the general nucleophilic carbamoylation procedure, tranexamic acid (6.9 g, 43.9 mmol) and 1-[(2,5-dioxopyrrolidinyl)oxycarbonyloxy]ethyl (2S)-2-[6-methoxy(2-naphthyl)]propanoate (ca. 6.2 g, 14.9 mmol) were reacted in the MTBE/acetone/water mixture (160 mL) to yield the title compound 27 (579 mg, 9% yield) as a colorless powder after work-up, purification by silica gel column chromatography using ethyl acetate/hexane mixtures from 2:1 to 4:1 as eluent, and subsequent mass-guided preparative HPLC. $^1H$ NMR (400 MHz, DMSO-$d^6$): δ=0.76-0.94 (m, 2H), 1.10-1.92 (m, 13H), 1.98-2.14 (m, 1H), 2.66-2.86 (m, 2H), 3.82-3.95 (m, 4H), 6.64-6.76 (m, 1H), 7.10-7.17 (m, 1H), 7.24-7.50 (m, 3H), 7.63-7.80 (m, 3H), 11.99 (br.s, 1H). MS (ESI) m/z 480.16 $(M+Na)^+$; 456.18 $(M-H)^-$.

Example 27 trans-4-{[1-(Propanoyloxy)propoxycarbonyl]aminomethyl}-Cyclohexanecarboxylic Acid (28)

Following the general nucleophilic carbamoylation procedure, tranexamic acid (472 mg, 3.0 mmol) and 1-[(2,5-dioxopyrrolidinyl)oxycarbonyloxy]propyl propanoate (281 mg, 1.03 mmol) were reacted in the MTBE/acetone/water mixture (16 mL) to yield the title compound 28 (173 mg, 53% yield) as a white powder after work-up and mass-guided preparative HPLC purification. $^1H$ NMR (400 MHz, DMSO-$d^6$): δ=0.82-0.94 (br. m, 5H), 1.01 (t, J=7.2 Hz, 3H), 1.17-1.37 (br. m, 3H), 1.64-1.75 (m, 4H), 1.83-1.91 (br. m, 2H), 2.10 (tt, J=12.0, 3.6 Hz, 1H), 2.23-2.38 (m, 2H), 2.76-2.87 (br. m, 2H), 6.54 (t, J=6.0 Hz, 1H), 7.42 (t, J=6.0 Hz, 1H), 11.97 (br. s, 1H). MS (ESI) m/z 338.16 $(M+Na)^+$; 314.12 $(M-H)^-$.

Example 28 trans-4-{[1-(Butanoyloxy)propoxycarbonyl]aminomethyl}-Cyclohexanecarboxylic Acid (29)

Following the general nucleophilic carbamoylation procedure, tranexamic acid (472 mg, 3.0 mmol) and 1-[(2,5-dioxopyrrolidinyl)oxycarbonyloxy]propyl butanoate (575 mg, 2.0 mmol) were reacted in the MTBE/acetone/water mixture (16 mL) to yield the title compound 29 (408 mg, 62% yield) as a white powder after work-up and mass-guided preparative HPLC purification. $^1H$ NMR (400 MHz, DMSO-$d^6$): δ=0.81-0.94 (br. m, 8H), 1.17-1.38 (br. m, 3H), 1.47-1.58 (m, 2H), 1.64-1.75 (m, 4H), 1.83-1.92 (br. m, 2H), 2.10 (tt, J=12.0, 3.6 Hz, 1H), 2.26 (t, J=7.2 Hz, 2H), 2.75-2.88 (m, 2H), 6.55 (t, J=5.2 Hz, 1H), 7.42 (t, J=5.6 Hz, 1H), 11.97 (br. s, 1H). MS (ESI) m/z 352.18 $(M+Na)^+$; 328.14 $(M-H)^-$.

Example 29 trans-4-{[1-(2-Methylpropanoyloxy)propoxycarbonyl]aminomethyl}-Cyclohexanecarboxylic Acid (30)

Following the general nucleophilic carbamoylation procedure, tranexamic acid (472 mg, 3.0 mmol) and 1-[(2,5-dioxopyrrolidinyl)oxycarbonyloxy]propyl 2-methylpropanoate (575 mg, 2.0 mmol) were reacted in the MTBE/acetone/water mixture (16 mL) to yield the title compound 30 (651 mg, 99% yield) as a white powder after work-up and mass-guided preparative HPLC purification. $^1H$ NMR (400 MHz, DMSO-$d^6$): δ=0.82-0.94 (br. m, 5H), 1.06 (d, J=6.8 Hz, 3H), 1.07 (d, J=6.8 Hz, 3H), 1.17-1.39 (br. m, 3H), 1.64-1.76 (br. m, 4H), 1.83-1.91 (br. m, 2H), 2.09 (tt, J=12.4, 3.6 Hz, 1H), 2.50 (hept., J=6.8 Hz, 1H), 2.77-2.84 (br. m, 2H), 6.52 (t, J=5.6 Hz, 1H), 7.43 (t, J=6.0 Hz, 1H), 11.98 (br. s, 1H). MS (ESI) m/z 352.06 $(M+Na)^+$; 328.02 $(M-H)^-$.

Example 30 trans-4-{[1-(2,2-Dimethylpropanoyloxy)propoxycarbonyl]aminomethyl}-Cyclohexanecarboxylic Acid (31)

Following the general nucleophilic carbamoylation procedure, tranexamic acid (472 mg, 3.0 mmol) and 1-[(2,5-dioxopyrrolidinyl)oxycarbonyloxy]propyl 2,2-dimethylpropanoate (290 mg, 0.96 mmol) were reacted in the MTBE/acetone/water mixture (16 mL) to yield the title compound 31 (147 mg, 45% yield) as a white powder after work-up and mass-guided preparative HPLC purification. $^1$H NMR (400 MHz, DMSO-d$^6$): δ=0.82-0.94 (br. m, 5H), 1.12 (s, 9H), 1.16-1.38 (m, 3H), 1.64-1.76 (m, 4H), 1.82-1.91 (br. m, 2H), 2.09 (tt, J=12.0, 3.2 Hz, 1H), 2.72-2.90 (m, 2H), 6.51 (t, J=5.6 Hz, 1H), 7.44 (t, J=6.0 Hz, 1H), 11.97 (br. s, 1H). MS (ESI) m/z 366.21 (M+Na)$^+$; 342.16 (M−H)$^-$.

Example 31 trans-4-{[1-(Benzoyloxy)propoxycarbonyl]aminomethyl}-Cyclohexanecarboxylic Acid (32)

Following the general nucleophilic carbamoylation procedure, tranexamic acid (472 mg, 3.0 mmol) and 1-[(2,5-dioxopyrrolidinyl)oxycarbonyloxy]propyl benzoate (602 mg, 2.0 nmol) were reacted in the MTBE/acetone/water mixture (16 mL) to yield the title compound 32 (679 mg, 93% yield) as a white powder after work-up and mass-guided preparative HPLC purification. $^1$H NMR (400 MHz, DMSO-d$^6$): δ=0.80-0.95 (br. m, 2H), 0.96 (t, J=7.6 Hz, 3H), 1.15-1.38 (br. m., 3H), 1.60-1.74 (m, 2H), 1.82-1.91 (m, 4H), 2.08 (tt, J=12.0, 3.2 Hz, 1H), 2.76-2.87 (br. m, 2H), 6.78 (t, J=5.6 Hz, 1H), 7.48-7.56 (br. m, 3H), 7.67 (tt, J=7.6, 1.2 Hz, 1H), 7.90-7.95 (m, 2H), 11.96 (br. s, 1H). MS (ESI) m/z 386.12 (M+Na)$^+$; 362.14 (M−H)$^-$.

Example 32 trans-4-{[1-(Acetoxy)butoxycarbonyl]aminomethyl}-Cyclohexanecarboxylic Acid (33)

Following the general nucleophilic carbamoylation procedure, tranexamic acid (472 mg, 3.0 mmol) and 1-[(2,5-dioxopyrrolidinyl)oxycarbonyloxy]butyl acetate (620 mg, 2.27 mmol) were reacted in the MTBE/acetone/water mixture (16 mL) to yield the title compound 33 (174 mg, 24% yield) as a waxy white solid after work-up and mass-guided preparative HPLC purification. $^1$H NMR (400 MHz, DMSO-d$^6$): δ=0.82-0.94 (br. m, 5H), 1.17-1.38 (br. m, 5H), 1.63-1.73 (br. m, 4H), 1.83-1.91 (br. m, 2H), 2.05 (s, 3H), 2.10 (tt, J=11.6, 3.6 Hz, 1H), 2.74-2.88 (m, 2H), 6.58 (t, J=5.6 Hz, 1H), 7.42 (t, J=6.0 Hz, 1H), 11.97 (br. s, 1H). MS (ESI) m/z 338.16 (M+Na)$^+$; 314.12 (M−H)$^-$.

Example 33 trans-4-{[1-(Propanoyloxy)butoxycarbonyl]aminomethyl}-Cyclohexanecarboxylic Acid (34)

Following the general nucleophilic carbamoylation procedure, tranexamic acid (472 mg, 3.0 mmol) and 1-[(2,5-dioxopyrrolidinyl)oxycarbonyloxy]butyl propanoate (686 mg, 2.38 mmol) were reacted in the MTBE/acetone/water mixture (16 mL) to yield the title compound 34 (144 mg, 18% yield) as a brittle off-white solid after work-up and mass-guided preparative HPLC purification. $^1$H NMR (400 MHz, DMSO-d$^6$): δ=0.82-0.94 (br. m, 5H), 1.01 (t, J=7.2 Hz, 3H), 1.17-1.38 (br. m, 5H), 1.63-1.73 (br. m, 4H), 1.84-1.92 (br. m, 2H), 2.10 (tt, J=12.0, 3.6 Hz, 1H), 2.22-2.38 (m, 2H), 2.75-2.87 (m, 2H), 6.60 (t, J=6.0 Hz, 1H), 7.42 (t, J=6.0 Hz, 1H), 11.97 (br. s, 1H). MS (ESI) m/z 352.18 (M+Na)$^+$; 328.14 (M−H)$^-$.

Example 34 trans-4-{[1-(Butanoyloxy)butoxycarbonyl]aminomethyl}-Cyclohexanecarboxylic Acid (35)

Following the general nucleophilic carbamoylation procedure, tranexamic acid (800 mg, 5 mmol) and 1-[(2,5-dioxopyrrolidinyl)oxycarbonyloxy]butyl butanoate (700 mg, 2.3 mmol) were reacted in the MTBE/acetone/water mixture (16 mL) to yield the title compound 35 (210 mg, 27% yield) as a white powder after work-up and mass-guided preparative HPLC purification. $^1$H NMR (400 MHz, DMSO-d$^6$): δ=0.87-0.95 (m, 8H), 1.22-1.41 (br. m, 5H), 1.56 (m, 2H), 1.68-1.73 (m, 4H), 1.89-1.92 (m, 2H), 2.13 (tt, J=12, 3.2 Hz, 1H), 2.30 (t, J=7.2 Hz, 2H), 6.65 (t, J=5.6 Hz, 1H), 7.45 (t, J=6.0 Hz, 1H), 12.04 (s, 1H). MS (ESI) m/z 366.21 (M+Na)$^+$; 342.16 (M−H)$^-$.

Example 35 trans-4-{[1-(2-Methylpropanoyloxy)butoxycarbonyl]aminomethyl}-Cyclohexanecarboxylic Acid (36)

Following the general nucleophilic carbamoylation procedure, tranexamic acid (800 mg, 5 mmol) and 1-[(2,5-dioxopyrrolidinyl)oxycarbonyloxy]butyl 2-methylpropanoate (700 mg, 2.3 mmol) were reacted in the MTBE/acetone/water mixture (16 mL) to yield the title compound 36 (100 mg, 13% yield) as a white powder after work-up and mass-guided preparative HPLC purification. $^1$H NMR (400 MHz, DMSO-d$^6$): δ=0.87-0.95 (m, 8H), 1.08 (d, J=4.0 Hz, 3H), 1.10 (d, J=4.0 Hz, 3H), 1.21-1.41 (br. m, 5H), 1.68-1.73 (m, 4H), 1.89-1.91 (m, 2H), 2.13 (tt, J=12, 3.2 Hz, 1H), 2.79-2.88 (m, 3H), 6.65 (t, J=5.6 Hz, 1H), 7.45 (t, J=6.0 Hz, 1H), 12.04 (s, 1H). MS (ESI) m/z 366.21 (M+Na)$^+$; 342.16 (M−H)$^-$.

Example 36 trans-4-{[1-(3-Methylbutanoyloxy)butoxycarbonyl]aminomethyl}-Cyclohexanecarboxylic Acid (37)

Following the general nucleophilic carbamoylation procedure, tranexamic acid (800 mg, 5.0 mmol) and 1-[(2,5-dioxopyrrolidinyl)oxycarbonyloxy]butyl 3-methylbutanoate (700 mg, 2.2 mmol) were reacted in the MTBE/acetone/water mixture (16 mL) to yield the title compound 37 (120 mg, 15% yield) as a white powder after work-up and mass-guided preparative HPLC purification. $^1$H NMR (400 MHz, DMSO-d$^6$): δ=0.87-0.95 (m, 11H), 1.21-1.41 (br. m, 5H), 1.68-1.73 (m, 4H), 1.89-2.02 (m, 3H), 2.10-2.22 (m, 3H), 2.80-2.89 (m, 2H), 6.65 (t, J=5.6 Hz, 1H), 7.45 (t, J=6.0 Hz, 1H), 12.04 (s, 1H). MS (ESI) m/z 380.23 (M+Na)$^+$; 356.18 (M−H)$^-$.

Example 37 trans-4-{[1-(2,2-Dimethylpropanoyloxy)butoxycarbonyl]aminomethyl}-Cyclohexanecarboxylic Acid (38)

Following the general nucleophilic carbamoylation procedure, tranexamic acid (800 mg, 5.0 mmol) and 1-[(2,5-dioxopyrrolidinyl)oxycarbonyloxy]butyl 2,2-dimethylpropanoate (700 mg, 2.2 mmol) were reacted in the MTBE/acetone/water mixture (16 mL) to yield the title compound 38

(90 mg, 12% yield) as a white powder after work-up and mass-guided preparative HPLC purification. $^1$H NMR (400 MHz, DMSO-d$^6$): δ=0.87-0.99 (m, 5H), 1.12-1.38 (br. m, 14H), 1.69-1.74 (m, 4H), 1.89-1.92 (m, 2H), 2.13 (tt, J=12, 3.2 Hz, 1H), 2.78-2.91 (m, 2H), 6.61 (t, J=5.6 Hz, 1H), 7.47 (t, J=6.0 Hz, 1H), 12.04 (s, 1H). MS (ESI) m/z 380.22 (M+Na)$^+$; 356.18 (M−H)$^-$.

Example 38 trans-4-{[1-(Benzoyloxy)butoxycarbonyl]aminomethyl}-Cyclohexanecarboxylic Acid (39)

Following the general nucleophilic carbamoylation procedure, tranexamic acid (800 mg, 5 mmol) and 1-[(2,5-dioxopyrrolidinyl)oxycarbonyloxy]butyl benzoate (700 mg, 2.1 mmol) were reacted in the MTBE/acetone/water mixture (16 mL) to yield the title compound 39 (150 mg, 19% yield) as a white powder after work-up and mass-guided preparative HPLC purification. $^1$H NMR (400 MHz, DMSO-d$^6$): δ=0.84-0.99 (m, 5H), 1.20-1.38 (br. m, 3H), 1.41-1.51 (m, 2H), 1.70-1.73 (m, 2H), 1.84-1.89 (m, 4H), 2.11 (tt, J=12, 3.2 Hz, 1H), 2.82-2.91 (m, 2H), 6.61 (t, J=5.6 Hz, 1H), 7.52-7.58 (m, 3H), 7.47 (t, J=6.0 Hz, 1H), 7.95-7.97 (m, 2H), 12.04 (s, 1H). MS (ESI) m/z 400.15 (M+Na)$^+$; 376.16 (M−H)$^-$.

Example 39 trans-4-{[1-(Acetoxy)-2-methylpropoxycarbonyl]aminomethyl}-Cyclohexanecarboxylic Acid (40)

Following the general nucleophilic carbamoylation procedure, tranexamic acid (472 mg, 3.0 mmol) and 1-[(2,5-dioxopyrrolidinyl)oxycarbonyloxy]-2-methylpropyl acetate (306 mg, 1.12 mmol) were reacted in the MTBE/acetone/water mixture (16 mL) to yield the title compound 40 (89 mg, 28% yield) as an oily solid after work-up and mass-guided preparative HPLC purification. $^1$H NMR (400 MHz, DMSO-d$^6$): δ=0.83-0.95 (br. m, 8H), 1.18-1.37 (m, 3H), 1.65-1.73 (br. m, 2H), 1.84-1.97 (br. m, 3H), 2.02 (s, 3H), 2.10 (tt, J=12.0, 3.6 Hz, 1H), 2.78-2.84 (m, 2H), 6.41 (d, J=5.2 Hz, 1H), 7.39 (t, J=6.0 Hz, 1H), 11.97 (br. s, 1H). MS (ESI) m/z 338.16 (M+Na)$^+$; 314.12 (M−H)$^-$.

Example 40 trans-4-{[1-(Propanoyloxy)-2-methylpropoxycarbonyl]aminomethyl}-Cyclohexanecarboxylic Acid (41)

Following the general nucleophilic carbamoylation procedure, tranexamic acid (250 mg, 1.6 mmol) and 1-[(2,5-dioxopyrrolidinyl)oxycarbonyloxy]-2-methylpropyl propanoate (230 mg, 0.80 mmol) were reacted in the MTBE/acetone/water mixture (16 mL) to yield the title compound 41 (70 mg, 21% yield) as a white powder after work-up and mass-guided preparative HPLC purification. $^1$H NMR (400 MHz, DMSO-d$^6$): δ=0.85-0.92 (m, 8H), 1.08 (t, J=7.2 Hz, 3H), 1.17-1.32 (br. m, 3H), 1.68 (d, J=12 Hz, 2H), 1.85-1.96 (br. m, 3H), 2.05-2.12 (m, 1H), 2.25-2.36 (br. m, 2H), 2.80 (t, J=6.4 Hz, 2H), 6.42 (d, J=5.2 Hz, 1H), 7.38 (t, J=6.0 Hz, 1H), 11.97 (br. s, 1H). MS (ESI) m/z 352.12 (M+Na)$^+$; 328.14 (M−H)$^-$.

Example 41 trans-4-{[1-(Pentanoyloxy)-2-methylpropoxycarbonyl]aminomethyl}-Cyclohexanecarboxylic Acid (42)

Following the general nucleophilic carbamoylation procedure, tranexamic acid (700 mg, 4.5 mmol) and 1-[(2,5-dioxopyrrolidinyl)oxycarbonyloxy]-2-methylpropyl pentanoate (500 mg, 1.6 mmol) were reacted in the MTBE/acetone/water mixture (16 mL) to yield the title compound 42 as a white powder after work-up and mass-guided preparative HPLC purification. $^1$H NMR (400 MHz, DMSO-d$^6$): δ=0.83-0.92 (br. m, 11H), 1.17-1.32 (br. m, 5H), 1.45-1.52 (m, 2H), 1.68 (d, J=12 Hz, 2H), 1.85-1.94 (br. m, 3H), 2.04-2.12 (m, 1H), 2.27-2.32 (br. m, 1H), 2.83 (td, J=7.2, 1.6 Hz, 2H), 2.78-2.82 (m, 2H), 6.42 (d, J=5.2 Hz, 1H), 7.38 (t, J=6.0 Hz, 1H), 11.97 (br. s, 1H). MS (ESI) m/z 380.16 (M+Na)$^+$; 356.17 (M−H)$^-$.

Example 42 trans-4-{[1-(Butanoyloxy)-2-methylpropoxycarbonyl]aminomethyl}-Cyclohexanecarboxylic Acid (43)

Following the general nucleophilic carbamoylation procedure, tranexamic acid (472 mg, 3.0 mmol) and 1-[(2,5-dioxopyrrolidinyl)oxycarbonyloxy]-2-methylpropyl butanoate (602 mg, 2.0 mmol) were reacted in the MTBE/acetone/water mixture (16 mL) to yield the title compound 43 (513 mg, 75% yield) as a white powder after work-up and mass-guided preparative HPLC purification. $^1$H NMR (400 MHz, DMSO-d$^6$): δ=0.83-0.95 (br. m, 11H), 1.17-1.38 (br. m, 3H), 1.48-1.58 (m, 2H), 1.65-1.73 (br. m, 2H), 1.83-1.98 (br. m, 3H), 2.10 (tt, J=12.0, 3.2 Hz, 1H), 2.21-2.32 (br. m, 2H), 2.75-2.87 (br. m, 2H), 6.44 (d, J=5.6 Hz, 1H), 7.40 (t, J=6.0 Hz), 11.97 (br. s, 1H). MS (ESI) m/z 366.21 (M+Na)$^+$; 342.16 (M−H)$^-$.

Example 43 trans-4-{[1-(2-Methylpropanoyloxy)-2-methylpropoxycarbonyl]aminomethyl}-Cyclohexanecarboxylic Acid (44)

Following the general nucleophilic carbamoylation procedure, tranexamic acid (472 mg, 3.0 mmol) and 1-[(2,5-dioxopyrrolidinyl)oxycarbonyloxy]-2-methylpropyl 2-methylpropanoate (603 mg, 2.0 mmol) were reacted in the MTBE/acetone/water mixture (16 mL) to yield the title compound 44 (486 mg, 71% yield) as a white powder after work-up and mass-guided preparative HPLC purification. $^1$H NMR (400 MHz, DMSO-d$^6$): δ=0.82-0.94 (br. m, 8H), 1.06 (d, J=6.8 Hz, 3H), 1.08 (d, J=7.2 Hz, 3H), 1.16-1.38 (br. m, 3H), 1.64-1.73 (br. m, 2H), 1.82-1.92 (br. m, 3H), 2.10 (tt, J=12.0, 3.6 Hz, 1H), 2.52 (hept., J=6.8 Hz, 1H), 2.74-2.87 (br. m, 2H), 6.42 (d, J=5.2 Hz, 1H), 7.40 (t, J=6.0 Hz, 1H), 11.97 (br. s, 1H). MS (ESI) m/z 366.08 (M+Na)$^+$; 342.04 (M−H)$^-$.

Example 44

Sodium trans-4-{[1-(2-Methylpropanoyloxy)-2-methylpropoxycarbonyl]aminomethyl}-Cyclohexanecarboxylate (45)

Following the general nucleophilic carbamoylation procedure for the formation of the corresponding sodium carboxylates of acyloxyalkyl carbamates of tranexamic acid, 3.434 g (10.0 mmol) of trans-4-{[1-(2-methylpropanoyloxy)-2-methylpropoxycarbonyl]aminomethyl}-cyclohexanecarboxylic acid 44 was reacted with 840.1 mg (10.0 mmol) of sodium bicarbonate (NaHCO$_3$) in 60 mL of a mixture of acetonitrile and water (1:2) to yield 3.654 g (quant.) of the title compound 45 as a colorless powder. $^1$H NMR (400 MHz, DMSO-d$^6$): δ=0.72-0.84 (m, 2H), 0.87-0.92 (m, 6H), 1.04-1.20 (m, 8H), 1.20-1.32 (m, 1H), 1.59-1.73 (m, 3H), 1.74-1.83 (m, 2H), 1.88-1.98 (m, 1H), 2.46-2.56 (m, 1H), 2.72-2.84 (br. m, 2H), 6.42 (d, J=5.6 Hz, 1H), 7.37 (t, J=5.6 Hz, 1H). MS (ESI) m/z 366.14 (M+Na)$^+$; 342.16 (M−H)$^-$.

Example 45 trans-4-{[1-(3-Methylbutanoyloxy)-2-methylpropoxycarbonyl]aminomethyl}-Cyclohexanecarboxylic Acid (46)

Following the general nucleophilic carbamoylation procedure, tranexamic acid (472 mg, 3.0 mmol) and 1-[(2,5-dioxopyrrolidinyl)oxycarbonyloxy]-2-methylpropyl 3-methylbutanoate (558 mg, 1.77 mmol) were reacted in the MTBE/acetone/water mixture (16 mL) to yield the title compound 46 (75 mg, 12% yield) as a white powder after work-up and mass-guided preparative HPLC purification. $^1$H NMR (400 MHz, DMSO-d$^6$): δ=0.82-0.94 (br. m, 14H), 1.17-1.37 (m, 3H), 1.65-1.73 (br. m, 2H), 1.83-2.01 (br. m, 4H), 2.09 (tt, J=12.4, 3.6 Hz, 1H), 2.17 (d, J=6.6 Hz, 2H), 2.74-2.87 (br. m, 2H), 6.45 (d, J=4.8 Hz, 1H), 7.40 (t, J=6.0 Hz, 1H), 11.97 (br. s, 1H). MS (ESI) m/z 380.23 (M+Na)$^+$; 356.18 (M−H)$^-$.

Example 46 trans-4-{[1-(2,2-Dimethylpropanoyloxy)-2-methylpropoxycarbonyl]aminomethyl}-Cyclohexanecarboxylic Acid (47)

Following the general nucleophilic carbamoylation procedure, tranexamic acid (472 mg, 3.0 mmol) and 1-[(2,5-dioxopyrrolidinyl)oxycarbonyloxy]-2-methylpropyl 2,2-dimethylpropanoate (631 mg, 2.0 mmol) were reacted in the MTBE/acetone/water mixture (16 mL) to yield the title compound 47 (23 mg, 3% yield) as an off-white powder after work-up and mass-guided preparative HPLC purification. $^1$H NMR (400 MHz, DMSO-d$^6$): δ=0.81-0.94 (br. m, 8H), 1.12 (s, 9H), 1.17-1.38 (m, 3H), 1.64-1.72 (br. m, 2H), 1.82-2.00 (br. m, 3H), 2.09 (tt, J=12.4, 3.2 Hz, 1H), 2.72-2.89 (br. m, 2H), 6.40 (d, J=4.8 Hz, 1H), 7.41 (t, J=5.6 Hz, 1H), 11.98 (br. s, 1H). MS (ESI) m/z 380.23 (M+Na)$^+$; 356.18 (M−H)$^-$.

Example 47 trans-4-{[1-(Cyclohexylcarbonyloxy)-2-methylpropoxycarbonyl]aminomethyl}-Cyclohexanecarboxylic Acid (48)

Following the general nucleophilic carbamoylation procedure, tranexamic acid (1.4 g, 8.0 mmol) and 1-[(2,5-dioxopyrrolidinyl)oxycarbonyloxy]-2-methylpropyl cyclohexanecarboxylate (1.0 g, 2.9 mmol) were reacted in the MTBE/acetone/water mixture (16 mL) to yield the title compound 48 (300 mg, 27% yield) as a white powder after work-up and mass-guided preparative HPLC purification. $^1$H NMR (400 MHz, DMSO-d$^6$): δ=0.83-0.92 (br. m, 8H), 1.15-1.35 (br. m, 8H), 1.54-1.95 (br. m, 10H), 2.08 (tt, J=12.0, 3.6 Hz, 1H), 2.27-2.32 (br. m, 1H), 2.74-2.83 (br. m, 2H), 6.41 (d, J=5.2 Hz, 1H), 7.39 (t, J=6.0 Hz, 1H), 11.97 (br. s, 1H). MS (ESI) m/z 406.14 (M+Na)$^+$; 382.17 (M−H)$^-$.

Example 48 trans-4-{[1-(Benzoyloxy)-2-methylpropoxycarbonyl]aminomethyl}-Cyclohexanecarboxylic Acid (49)

Following the general nucleophilic carbamoylation procedure, tranexamic acid (630 mg, 4.0 mmol) and 1-[(2,5-dioxopyrrolidinyl)oxycarbonyloxy]-2-methylpropyl benzoate (500 mg, 1.5 mmol) were reacted in the MTBE/acetone/water mixture (16 mL) to yield the title compound 49 (200 mg, 35% yield) as a white powder after work-up and mass-guided preparative HPLC purification. $^1$H NMR (400 MHz, DMSO-d$^6$): δ=0.84-0.91 (br. m, 2H), 0.99 (d, J=6.8 Hz, 6H), 1.16-1.31 (br. m, 3H), 1.66-1.68 (br. m, 2H), 1.82-1.85 (m, 2H), 2.03-2.12 (br. m, 2H), 2.80 (t, J=6.4 Hz, 2H), 6.11 (d, J=4.4 Hz, 1H), 7.51 (t, J=6.0 Hz, 1H), 7.57 (t, J=6.0 Hz, 2H), 7.71 (t, J=7.2 Hz, 1H), 7.96 (dd, J=8.4, 1.6 Hz, 2H), 11.97 (br. s, 1H). MS (ESI) m/z 400.08 (M+Na)$^+$; 376.10 (M−H)$^-$.

Example 49 trans-4-{[1-(Butanoyloxy)-1-cyclohexylmethoxycarbonyl]aminomethyl}-Cyclohexanecarboxylic Acid (50)

Following the general nucleophilic carbamoylation procedure, tranexamic acid (472 mg, 3.0 mmol) and 1-[(2,5-dioxopyrrolidinyl)oxycarbonyloxy]cyclohexylmethyl butanoate (683 mg, 2.0 mmol) were reacted in the MTBE/acetone/water mixture (16 mL) to yield the title compound 50 (329 mg, 43% yield) as a white powder after work-up and mass-guided preparative HPLC purification. $^1$H NMR (400 MHz, DMSO-d$^6$): δ=0.83-0.95 (br. m, 5H), 0.96-1.37 (br. m, 8H), 1.47-1.57 (m, 2H), 1.58-1.74 (br. m, 8H), 1.83-1.92 (br. m, 2H), 2.09 (tt, J=12.0, 3.6 Hz, 1H), 2.26 (td, J=7.6, 0.8 Hz, 2H), 2.74-2.86 (m, 2H), 6.44 (d, J=5.6 Hz, 1H), 7.39 (t, J=6.0 Hz, 1H), 11.97 (br. s, 1H). MS (ESI) m/z 406.24 (M+Na)$^+$; 382.23 (M−H)$^-$.

Example 50 trans-4-{[1-(2-Methylpropanoyloxy)-1-cyclohexylmethoxycarbonyl]aminomethyl}-Cyclohexanecarboxylic Acid (51)

Following the general nucleophilic carbamoylation procedure, tranexamic acid (472 mg, 3.0 mmol) and 1-[(2,5-dioxopyrrolidinyl)oxycarbonyloxy]cyclohexylmethyl 2-methylpropanoate (683 mg, 2.0 mmol) were reacted in the MTBE/acetone/water mixture (16 mL) to yield the title compound 51 (327 mg, 43% yield) as a white powder after work-up and mass-guided preparative HPLC purification. $^1$H NMR (400 MHz, DMSO-d$^6$): δ=0.81-0.94 (br. m, 2H), 1.00-1.36 (br. m, 14H), 1.58-1.74 (br. m, 8H), 1.83-1.91 (br. m, 2H), 2.09 (tt, J=12.0, 3.6 Hz, 1H), 2.51 (hept., J=6.8 Hz, 1H), 2.74-2.86 (m, 2H), 6.41 (d, J=5.2 Hz, 1H), 7.40 (br. t, J=5.6 Hz, 1H), 11.97 (br. s, 1H). MS (ESI) m/z 406.18 (M+Na)$^+$; 382.19 (M−H)$^-$.

Example 51

Standard Methods for Determination of Enzymatic Cleavage of Prodrugs in Vitro

The stabilities of prodrugs were evaluated in one or more in vitro systems using a variety of tissue preparations following methods known in the art. The chemical stability of prodrugs in aqueous buffers at a pH of 2.0, 7.4, and 8.0 were also measured. Tissues were obtained from commercial sources (e.g., Pel-Freez Biologicals, Rogers, A R, or GenTest Corporation, Woburn, Mass.). Experimental conditions used for the in vitro studies are described in Table 1. Each preparation was incubated with test compound at 37° C. for one hour. Aliquots (50 μL) were removed at 0, 30, and 60 min and quenched with 0.1% trifluoroacetic acid in acetonitrile. Samples were then centrifuged and analyzed by LC/MS/MS. Stability of prodrugs towards specific enzymes (e.g., peptidases, etc.) was also assessed in vitro by incubation with the purified enzyme.

Pancreatin Stability: Stability studies were conducted by incubating prodrug (5 μM) with 1% (w/v) pancreatin (Sigma, P-1625, from porcine pancreas) in 0.025 M Tris buffer containing 0.5 M NaCl (pH 7.5) at 37° C. for 60 min. The reaction was stopped by addition of 2 volumes of methanol. After centrifugation at 14,000 rpm for 10 min, the supernatant was removed and analyzed by LC/MS/MS.

Caco-2 Homogenate S9 Stability: Caco-2 cells were grown for 21 days prior to harvesting. Culture medium was removed and cell monolayers were rinsed and scraped off into ice-cold 10 mM sodium phosphate/0.15 M potassium chloride, pH 7.4. Cells were lysed by sonication at 4° C. using a probe sonicator. Lysed cells were then transferred into 1.5 mL centrifuge vials and centrifuged at 9,000 g for 20 min at 4° C. The resulting supernatant (Caco-2 cell homogenate S9 fraction) was aliquoted into 0.5 mL vials and stored at −80° C. until used.

TABLE 1

Standard Conditions for Prodrug In Vitro Metabolism Studies

| Preparation | Substrate Concentration | Cofactors |
|---|---|---|
| Rat Plasma | 2.0 µM | None |
| Human Plasma | 2.0 µM | None |
| Rat Liver S9 (0.5 mg/mL) | 2.0 µM | NADPH* |
| Human Liver S9 (0.5 mg/mL) | 2.0 µM | NADPH* |
| Human Intestine S9 (0.5 mg/mL) | 2.0 µM | NADPH* |
| CarboxypeptidaseA (10 units/mL) | 2.0 µM | None |
| Caco-2 Homogenate | 5.0 µM | None |
| Pancreatin | 5.0 µM | None |

*NADPH generating system, e.g., 1.3 mM NADP$^+$, 3.3 mM glucose-6-phosphate, 0.4 U/mL glucose-6-phosphate dehydrogenase, 3.3 mM magnesium chloride and 0.95 mg/mL potassium phosphate, pH 7.4.

For stability studies, prodrug (5 µM) was incubated in Caco-2 homogenate S9 fraction (0.5 mg protein per mL) for 60 min at 37° C. Concentrations of intact prodrug and released tranexamic acid were determined at zero time and 60 min using LC/MS/MS.

pH-Dependent Stability: The long-term pH-dependent stability of tranexamic acid prodrug at 37° C. was measured by LC/MS/MS at five different representative pH values from pH 2.0 to pH 8.0 was determined. The test concentration was 5 µM. The amount of remaining prodrug and the amount of tranexamic acid released from the prodrug was determined at 0 hour and after 24 hours.

Compounds 13, 15-19, 32-34, 44, 46, 48-49, and 51, for example, showed good stability from pH 2 to pH 8, are stable in the presence of pancreatin and colonic wash (>40% intact prodrug remaining after 60 min incubation) and are extensively hydrolyzed to liberate tranexamic acid in the presence of human liver S9(<15% prodrug remaining after 60 min incubation).

Example 52

In Vitro Determination of Caco-2 Cellular Permeability of Prodrugs

The passive permeability of the prodrugs of the present disclosure can be assessed in vitro using standard methods well known in the art (See, e.g., Stewart, et al., *Pharm. Res.*, 1995, 12, 693). For example, passive permeability can be evaluated by examining the flux of a prodrug across a cultured polarized cell monolayer (e.g., Caco-2 cells).

Caco-2 cells obtained from continuous culture (passage less than 28) were seeded at high density onto Transwell polycarbonate filters. Cells were maintained with DMEM/10% fetal bovine serum, 1 mM nonessential amino acids, and 6 mM L-Gln, 5% $CO_2$/95% $O_2$, at 37° C. until the day of the experiment. Permeability studies were conducted at pH 6.5 apically (in 50 mM MES buffer containing 1 mM $CaCl_2$, 1 mM $MgCl_2$, 150 mM NaCl, 3 mM KCl, 1 mM $NaH_2PO_4$, 5 mM glucose) and pH 7.4 basolaterally (in Hanks' balanced salt solution containing 10 mM HEPES) in the presence of efflux pump inhibitors (250 µM MK-571 and 250 µM Verapamil). Inserts were placed in 12 or 24 well plates containing buffer and incubated for 30 min at 37° C. Prodrug (200 µM) was added to the apical or basolateral compartment (donor) and concentrations of prodrug and/or released parent drug in the opposite compartment (receiver) were determined at intervals over 1 hour using LC/MS/MS. Values of apparent permeability ($P_{app}$) were calculated using the equation:

$$P_{app} = V_r(dC/dt)/(AC_o)$$

where $V_r$ is the volume of the receiver compartment in mL; dC/dt is the total flux of prodrug and parent drug (µM/sec), determined from the slope of the plot of concentration in the receiver compartment versus time; $C_0$ is the initial concentration of prodrug in µM; and A is the surface area of the membrane in cm$^2$. Prodrugs with significant transcellular permeability may demonstrate a value of $P_{app}$ of $\geq 1 \times 10^{-6}$ cm/sec, for example, a value of $P_{app}$ of $\geq 1 \times 10^{-5}$ cm/sec, or even a value of $P_{app}$ of $>5 \times 10^{-5}$ cm/sec. Typical values of $P_{app}$ obtained for prodrugs of the present disclosure are shown in Table 2.

TABLE 2

Caco-2 cellular permeability of acyloxyalkylcarbamate tranexamic acid prodrugs.

| Compound | $P_{app}$ (apical to basolateral) ($\times 10^{-5}$ cm/sec) | $P_{app}$ (basolateral to apical) ($\times 10^{-5}$ cm/sec) | Ratio A-B/B-A |
|---|---|---|---|
| 1 | 0.04 | 0.03 | 1.3 |
| 4 | 4.74 | 0.62 | 7.7 |
| 7 | 4.06 | 0.97 | 4.2 |
| 10 | 6.04 | 1.22 | 4.9 |
| 13 | 5.09 | 1.07 | 4.8 |
| 14 | 4.49 | 1.34 | 3.4 |
| 15 | 7.32 | 1.20 | 6.1 |
| 17 | 4.87 | 1.22 | 4.0 |
| 19 | 7.24 | 1.39 | 5.2 |
| 23 | 7.90 | 1.77 | 4.5 |
| 36 | 3.77 | 0.84 | 4.5 |
| 42 | 4.68 | 1.59 | 2.9 |
| 44 | 6.05 | 2.70 | 2.2 |
| 48 | 5.58 | 1.79 | 3.1 |
| 49 | 4.50 | 1.54 | 2.9 |

The data in Table 2 shows that the prodrugs disclosed herein have high cellular permeability and should be well absorbed from the intestine. The apical-to-basolateral permeabilities of these prodrugs exceed their basolateral-to-apical permeabilities. This suggests that these compounds are substrates for active transport mechanisms present in the apical membrane of Caco-2 cells (although some component of this transcellular permeability may also be mediated by passive diffusion).

Example 53

Pharmacokinetics of Tranexamic Acid Following Administration of Tranexamic Acid or Tranexamic Acid Prodrug to Rats Tranexamic acid or a tranexamic acid prodrug of the present disclosure was administered as an intravenous bolus injection (i.v.), by oral gavage (p.o.), or by intracolonic (i.c.)

administration via an indwelling catheter in the ascending colon to groups of four to six adult male Sprague-Dawley rats (weight approximately 250 g). Animals were fasted overnight before the study and for 4 hours post-dosing and were conscious at the time of the experiment. When administered intravenously, tranexamic acid was administered as a solution in water at a dose equivalent to 16 mg (0.1 mmol) of tranexamic acid per kg body weight. Prodrugs were orally or intracolonically administered as a suspension in 0.5% methyl cellulose in 0.1% Tween 80 at a dose equivalent to 16 mg (0.1 mmol) of tranexamic acid per kg body weight. Blood samples (300 μL) were obtained via a jugular vein cannula at intervals over 8 hours after oral dosing. Blood was quenched immediately using methanol and then was frozen at −80° C. until analyzed.

The following procedure was used to prepared blood samples for analysis:

1. Rat blood (100 μL) was collected at different times into K2EDTA tubes, 300 μL of methanol, and the mixture was vortexed to mix the ingredients.

2. Blank rat blood (90 μL) was quenched with 300 μL of methanol. Then ten μL of a standard stock solution (0.04, 0.2, 1, 5, 25, and 100 μg/mL) were added to the tube individually. Then 20 μL of p-chlorophenylalanine (5 μg/mL in 50% methanol) was added to each tube to make up a final calibration standard (0.004, 0.02, 0.1, 0.5, 2.5, and 10 μg/mL). The samples were vortexed and centrifuged at 14,000 rpm for 20 min.

3. To the quenched blood samples were added 20 μL of p-chlorophenylalanine (5 μg/mL in 50% methanol), the samples were vortexed and centrifuged at 14,000 rpm for 20 min.

4. The supernatant was analyzed by LC/MS/MS.

The following method was used for LC/MS/MS Analysis of the prepared blood samples. An API 4000 or 2000 LC/MS/MS spectrometer equipped with Agilent 1100 binary pumps and a CTC HTS-PAL autosampler were used in the analysis. A ThermoHypersil-BetaSil C18, 100×4.6 mm, 5 μm column was used during the analysis. The mobile phase for the analysis of tranexamic acid and prodrug was (A) 0.1% formic acid in water, and (B) 0.1% formic acid in acetonitrile. The gradient condition was: 2% eluent-B to 95% eluent-B for 2.5 min, then to 98% eluent-B to 4.0 min. At 4.1 min, it was returned to 2% eluent-B and maintained at 2% eluent-B till 6.0 min. The flow rate was 1 mL/min. An ESI source was used on the API 4000. The analysis of tranexamic acid was performed in positive ion mode for and negative ion mode was used for analysis of tranexamic acid prodrugs.

The MRM transition for each analyte was optimized using standard solutions. 20 μL of the sample was injected. Non-compartmental analysis was performed using WinNonlin (v.3.1 Professional Version, Pharsight Corporation, Mountain View, Calif.) on individual animal profiles. Summary statistics on major parameter estimates was performed for Cmax (peak observed concentration following dosing), Tmax (time to maximum concentration is the time at which the peak concentration was observed), $AUC_{(0-t)}$ (area under the serum concentration-time curve from time zero to last collection time, estimated using the log-linear trapezoidal method), $AUC_{(0-\infty)}$, (area under the serum concentration time curve from time zero to infinity, estimated using the log-linear trapezoidal method to the last collection time with extrapolation to infinity), and $t_{1/2}$ (terminal half-life).

Figure 2:
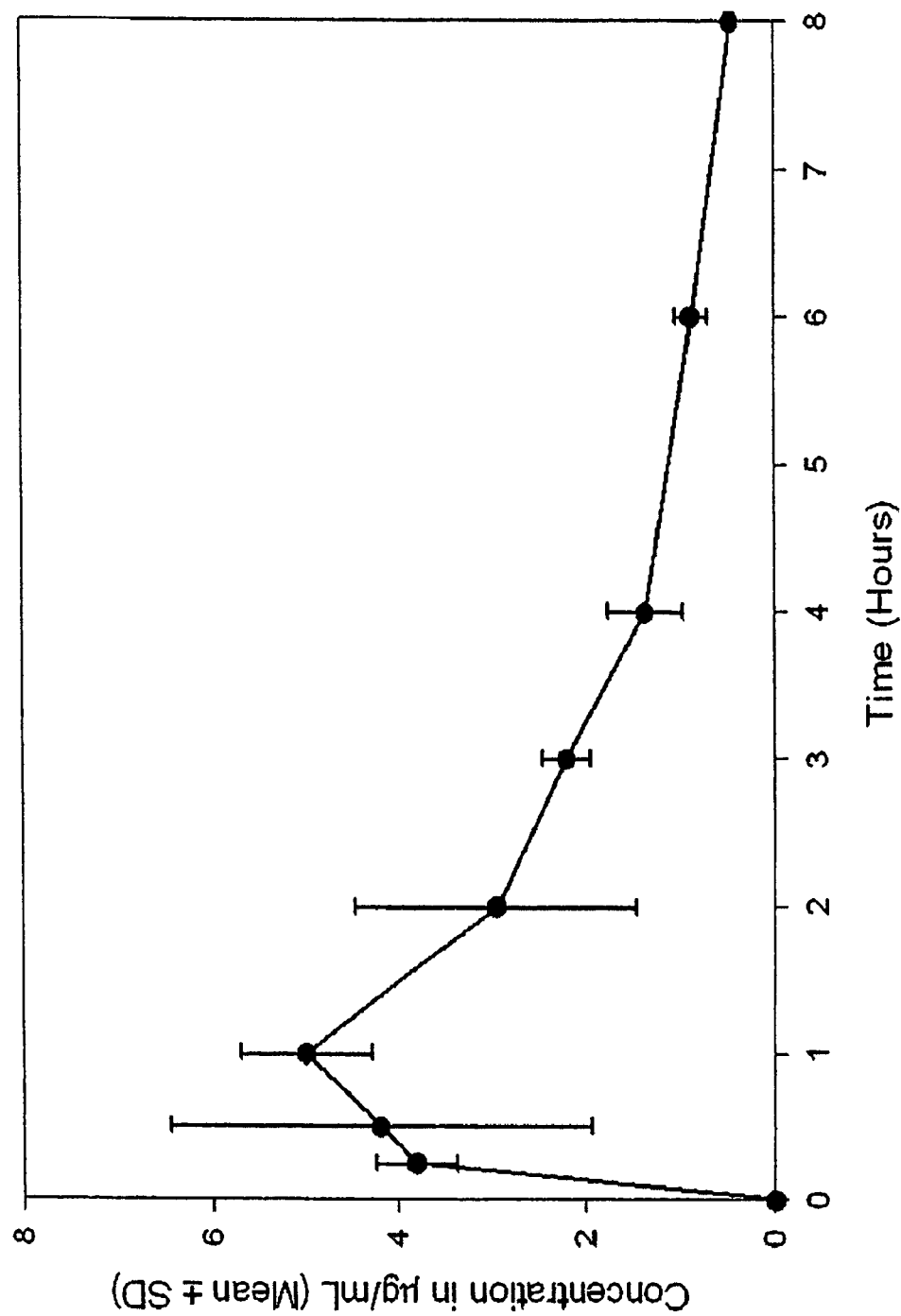
FIG. 2 shows the pharmacokinetics profile of tranexamic acid following oral administration of tranexamic acid prodrug 13. The levels of prodrug 13 following oral gavage administration were below the level of detection.

The oral or intracolonic bioavailability (F) of tranexamic acid was determined by comparing the area under the tranexamic acid concentration vs. time curve (AUC) following oral or intracolonic administration of tranexamic acid or prodrug with the AUC of the tranexamic acid concentration vs. time curve following intravenous administration of tranexamic acid on a dose normalized basis. An $AUC_{inf}$ of 22.2 hr·μg/mL for the intravenously administered tranexamic acid (dosed at 16 mg/kg) was used for the calculations of the bioavailability of tranexamic acid released from prodrugs post absorption. The results for tranexamic acid and tranexamic prodrug 13 are shown in Table 3, FIG. 1, and FIG. 2. In Table 3, the values represent the mean ±1SD. When administered intracolonically, each of compounds 13-20, 23-24, and 44-45, for example, showed greater than 8-fold higher bioavailability of tranexamic acid compared to the bioavailability of tranexamic acid when tranexamic acid itself was administered intracolonically.

TABLE 3

Pharmacokinetic parameters of tranexamic acid and a tranexamic acid prodrug.

|  | Tranexamic Acid | Tranexamic Acid | Compound 13 | Compound 13 |
|---|---|---|---|---|
| Route of Administration | p.o | i.c. | p.o | i.c. |
| $C_{max}$ (mg/mL) | 2.06 (0.45) | 0.22 (0.22) | 5.64 (0.58) | 7.82 (5.2) |
| $T_{max}$ (h) | 1.1 (0.5) | 3.1 (2.4) | 0.8 (0.3) | 0.5 (0.1) |
| $T_{1/2-\lambda}$ (h) | 1.9 (0.1) | 1.7 (1.6) | 2.2 (0.2) | 4.2 (0.8) |
| $AUC_t$ (hr · mg/mL) | 7.3 (1.8) | 0.6 (0.7) | 15.7 (2.0) | 21.5 (2.3) |
| $AUC_{inf}$ (hr · mg/mL) | 7.8 (1.9) | 0.8 (0.8) | 17.1 (2.0) | 21.8 |
| F* (%) | 37 (7) | 5 (4) | 73 (9) | 98 (10) |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not as a limitation on the scope of the claims.

What is claimed is:

1. A method of treating bleeding in a patient in need of such treatment, comprising administering to the patient a therapeutically effective amount of at least one compound of Formula (I):

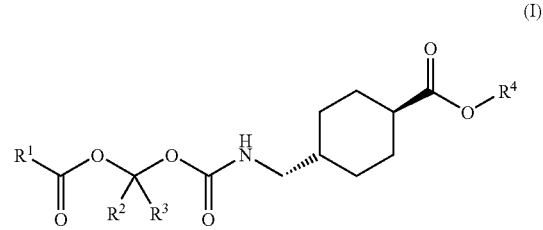

or a pharmaceutically acceptable salt thereof, wherein:
$R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;
$R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring; and
$R^4$ is selected from hydrogen, alkyl, substituted alkyl, aryl, substituted aryl, arylalkyl, substituted arylalkyl, aryldialkylsilyl, substituted aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, trialkylsilyl, and substituted trialkylsilyl.

2. The method of claim 1 wherein
$R^1$ is selected from $C_{1-4}$ alkyl, phenyl, o-tolyl, and cyclohexyl;
$R^2$ is hydrogen;
$R^3$ is selected from $C_{1-3}$ alkyl, phenyl, and cyclohexyl; and
$R^4$ is selected from hydrogen, $C_{1-4}$ alkyl, benzyl, 4-methoxybenzyl, diphenylmethyl, triphenylmethyl, trimethylsilyl, triethylsilyl, triisopropylsilyl, tert-butyldimethylsilyl, and phenyldimethylsilyl.

3. The method of claim 2, wherein:
$R^1$ is selected from isopropyl, isobutyl, and phenyl;
$R^3$ is selected from methyl and isopropyl; and
$R^4$ is hydrogen.

4. A method of treating bleeding in a patient in need of such treatment, comprising administering to the patient a therapeutically effective amount of at least one compound of Formula (I):

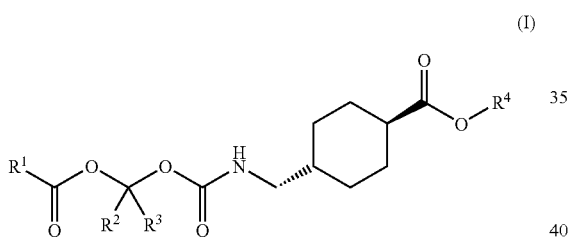

a stereoisomer thereof, or a pharmaceutically acceptable salt of any of the foregoing;
wherein $R^1$ is isopropyl; one of $R^2$ and $R^3$ is hydrogen and the other of $R^2$ and $R^3$ is methyl; and $R^4$ is hydrogen.

5. The method of claim 4, wherein the compound is selected from:
(+)-trans-4-({[(1S)-1-(2-methylpropanoyloxy)ethoxy]carbonylamino}methyl)-cyclohexanecarboxylic acid;
(−)-trans-4-({[(1R)-1-(2-methylpropanoyloxy)ethoxy]carbonylamino}methyl)-cyclohexanecarboxylic acid; and
mixtures thereof.

6. The method of claim 4, wherein the compound is selected from:
sodium trans-4-({[(1S)-1-(2-methylpropanoyloxy)ethoxy]carbonylamino}methyl)-cyclohexanecarboxylate;
sodium trans-4-({[(1R)-1-(2-methylpropanoyloxy)ethoxy]carbonylamino}methyl)-cyclohexanecarboxylate; and
mixtures thereof.

7. The method of any of claims 1 to 6, wherein the bleeding comprises excessive menstrual bleeding.

8. A method of treating a condition selected from wound healing, epidermal hyperplasia, skin roughening, unwanted skin pigmentation, or tumor metastasis in a patient in need of such treatment, comprising administering to the patient a therapeutically effective amount of at least one compound of Formula (I):

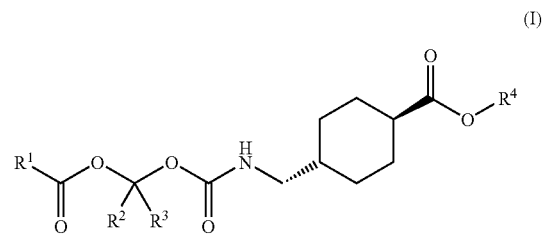

or a pharmaceutically acceptable salt thereof, wherein:
$R^1$ is selected from acyl, substituted acyl, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, and substituted heteroarylalkyl;
$R^2$ and $R^3$ are independently selected from hydrogen, alkyl, substituted alkyl, alkoxycarbonyl, substituted alkoxycarbonyl, aryl, substituted aryl, arylalkyl, substituted arylalkyl, carbamoyl, substituted carbamoyl, cycloalkyl, substituted cycloalkyl, heteroalkyl, substituted heteroalkyl, heteroaryl, substituted heteroaryl, heteroarylalkyl, and substituted heteroarylalkyl, or $R^2$ and $R^3$ together with the carbon atom to which they are bonded form a cycloalkyl, substituted cycloalkyl, cycloheteroalkyl, or substituted cycloheteroalkyl ring; and
$R^4$ is selected from hydrogen, alkyl, substituted alkyl, aryl, substituted aryl, arylalkyl, substituted arylalkyl, aryldialkylsilyl, substituted aryldialkylsilyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, trialkylsilyl, and substituted trialkylsilyl.

9. The method of claim 8, wherein
$R^1$ is selected from $C_{1-4}$ alkyl, phenyl, o-tolyl, and cyclohexyl;
$R^2$ is hydrogen;
$R^3$ is selected from $C_{1-3}$ alkyl, phenyl, and cyclohexyl; and
$R^4$ is selected from hydrogen, $C_{1-4}$ alkyl, benzyl, 4-methoxybenzyl, diphenylmethyl, triphenylmethyl, trimethylsilyl, triethylsilyl, triisopropylsilyl, tert-butyldimethylsilyl, and phenyldimethylsilyl.

10. The method of claim 9, wherein:
$R^1$ is selected from isopropyl, isobutyl, and phenyl;
$R^3$ is selected from methyl and isopropyl; and
$R^4$ is hydrogen.

11. A method of treating a condition selected from wound healing, epidermal hyperplasia, skin roughening, unwanted skin pigmentation, or tumor metastasis in a patient in need of such treatment, comprising administering to the patient a therapeutically effective amount of at least one compound of Formula (I):

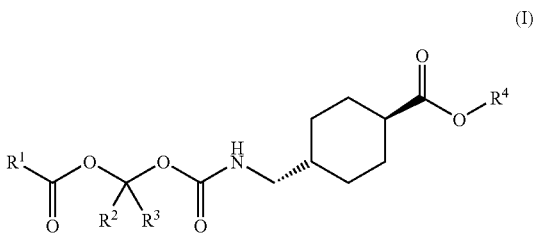
(I)

a stereoisomer thereof, or a pharmaceutically acceptable salt of any of the foregoing,
wherein $R^1$ is isopropyl; one of $R^2$ and $R^3$ is hydrogen and the other of $R^2$ and $R^3$ is methyl; and $R^4$ is hydrogen.

12. The method of claim 11, wherein the compound is selected from:
(+)-trans-4-({[(1S)-1-(2-methylpropanoyloxy)ethoxy]carbonylamino}methyl)-cyclohexanecarboxylic acid;
(−)-trans-4-({[(1R)-1-(2-methylpropanoyloxy)ethoxy]carbonylamino}methyl)-cyclohexanecarboxylic acid; and
mixtures thereof.

13. The method of claim 11, wherein the compound is selected from:
sodium trans-4-({[(1S)-1-(2-methylpropanoyloxy)ethoxy]carbonylamino}methyl)-cyclohexanecarboxylate;
sodium trans-4-({[(1R)-1-(2-methylpropanoyloxy)ethoxy]carbonylamino}methyl)-cyclohexanecarboxylate; and
mixtures thereof.

14. The method of claim 8, in the treatment of a tumor metastasis, comprising administering at least one cytotoxic agent to the patient.

15. The method of claim 1, wherein bleeding is associated with cardiac surgery, upper gastrointestinal hemorrhage, blood loss in patients with advanced cancer, bleeding that occurs during dental procedures in hemophiliacs, and heavy bleeding during menstruation.

16. The method of claim 15, wherein blood loss in patients with advanced cancer is associated with acute hemorrhagic events or low-volume chronic bleeding.

17. The method of claim 4, wherein bleeding is associated with cardiac surgery, upper gastrointestinal hemorrhage, blood loss in patients with advanced cancer, bleeding that occurs during dental procedures in hemophiliacs, and heavy bleeding during menstruation.

18. The method of claim 17, wherein blood loss in patients with advanced cancer is associated with acute hemorrhagic events or low-volume chronic bleeding.

19. The method of claim 1, wherein administering to the patient a therapeutically effective amount of at least one compound of Formula (I) comprises administering to the patient a pharmaceutical composition comprising a therapeutically effective amount of at least one compound of Formula (I).

20. The method of claim 19, wherein the pharmaceutical composition is an oral formulation.

21. The method of claim 20, wherein the oral formulation is a sustained release oral formulation.

22. The method of claim 19, wherein the pharmaceutical composition is a topical formulation.

23. The method of claim 22, wherein the topical formulation is a sustained release topical formulation.

24. The method of claim 4, wherein administering to the patient a therapeutically effective amount of at least one compound of Formula (I) comprises administering to the patient a pharmaceutical composition comprising a therapeutically effective amount of at least one compound of Formula (I).

25. The method of claim 24, wherein the pharmaceutical composition is an oral formulation.

26. The method of claim 25, wherein the. oral formulation is a sustained release oral formulation.

27. The method of claim 24, wherein the pharmaceutical composition is a topical formulation.

28. The method of claim 27, wherein the topical formulation is a sustained release topical formulation.

29. The method of claim 7, wherein administering to the patient a therapeutically effective amount of at least one compound of Formula (I) comprises administering to the patient a pharmaceutical composition comprising a therapeutically effective amount of at least one compound of Formula (I).

30. The method of claim 29, wherein the pharmaceutical composition is an oral formulation.

31. The method of claim 30, wherein the oral formulation is a sustained release oral formulation.

32. The method of claim 29, wherein the pharmaceutical composition is a topical formulation.

33. The method of claim 32, wherein the topical formulation is a sustained release topical formulation.

34. The method of claim 11, wherein administering to the patient a therapeutically effective amount of at least one compound of Formula (I) comprises administering to the patient a pharmaceutical composition comprising a therapeutically effective amount of at least one compound of Formula (I).

35. The method of claim 34, wherein the pharmaceutical composition is an oral formulation.

36. The method of claim 35, wherein the oral formulation is a sustained release oral formulation.

37. The method of claim 34, wherein the pharmaceutical composition is a topical formulation.

38. The method of claim 37, wherein the topical formulation is a sustained release topical formulation.

39. The method of claim 3, wherein:
$R^1$ is isopropyl;
$R^3$ is methyl; and
$R^4$ is hydrogen.

40. The method of claim 10, wherein:
$R^1$ is isopropyl;
$R^3$ is methyl; and
$R^4$ is hydrogen.

41. The method of claim 4, wherein the compound is trans-4-{[1-(2-methylpropanoyloxy)ethoxycarbonyl]-aminomethyl}-cyclohexanecarboxylic acid.

42. The method of claim 4, wherein the compound is sodium trans-4-{[1-(2-methylpropanoyloxy)ethoxycarbonyl]-aminomethyl}-cyclohexanecarboxylate.

43. The method of claim 11, wherein the compound is trans-4-{[1-(2-methylpropanoyloxy)ethoxycarbonyl]-aminomethyl}-cyclohexanecarboxylic acid.

44. The method of claim 11, wherein the compound is sodium trans-4-{[1-(2-methylpropanoyloxy)ethoxycarbonyl]-aminomethyl}-cyclohexanecarboxylate.

* * * * *